(12) United States Patent
Kalachikov et al.

(10) Patent No.: US 10,526,647 B2
(45) Date of Patent: Jan. 7, 2020

(54) NUCLEIC ACID SEQUENCES USING TAGS

(71) Applicants: Sergey Kalachikov, New York, NY (US); Jingyue Ju, New York, NY (US); Irina Morozova, New York, NY (US); Michael Dorwart, Mountain View, CA (US)

(72) Inventors: Sergey Kalachikov, New York, NY (US); Jingyue Ju, New York, NY (US); Irina Morozova, New York, NY (US); Michael Dorwart, Mountain View, CA (US)

(73) Assignees: THE TRUSTEES OF COLUMBIA UNIVERSITY IN THE CITY OF NEW YORK, New York, NY (US); ROCHE SEQUENCING SOLUTIONS, INC., Pleasanton, CA (US)

( * ) Notice: Subject to any disclaimer, the term of this patent is extended or adjusted under 35 U.S.C. 154(b) by 238 days.

(21) Appl. No.: 15/449,757

(22) Filed: Mar. 3, 2017

(65) Prior Publication Data

US 2017/0241948 A1    Aug. 24, 2017

Related U.S. Application Data

(62) Division of application No. 14/073,445, filed on Nov. 6, 2013, now Pat. No. 9,605,309.

(Continued)

(51) Int. Cl.
   *C12Q 1/68*      (2018.01)
   *C12Q 1/6869*    (2018.01)
   (Continued)

(52) U.S. Cl.
   CPC ..... *C12Q 1/6869* (2013.01); *G01N 27/44717* (2013.01); *G01N 27/44791* (2013.01); *G01N 33/48721* (2013.01)

(58) Field of Classification Search
   None
   See application file for complete search history.

(56) References Cited

U.S. PATENT DOCUMENTS

| 4,121,192 A | 10/1978 | Wilson |
| 4,859,945 A | 8/1989 | Stokar |

(Continued)

FOREIGN PATENT DOCUMENTS

| WO | WO 1991/006678 | 5/1991 |
| WO | WO 1993/021340 | 10/1993 |

(Continued)

OTHER PUBLICATIONS

Li. L. et al. (2001) "Ion-beam sculpting at nanometer length scales" Nature 412:166-169.

(Continued)

*Primary Examiner* — Samuel C Woolwine
(74) *Attorney, Agent, or Firm* — John P. White; Gary J. Gershik; Cooper & Dunham LLP

(57) ABSTRACT

This disclosure provides chips, systems and methods for sequencing a nucleic acid sample. Tagged nucleotides are provided into a reaction chamber comprising a nanopore in a membrane. An individual tagged nucleotide of the tagged nucleotides can contain a tag coupled to a nucleotide, which tag is detectable with the aid of the nanopore. Next, an individual tagged nucleotide of the tagged nucleotides can be incorporated into a growing strand complementary to a single stranded nucleic acid molecule derived from the nucleic acid sample. With the aid of the nanopore, a tag associated with the individual tagged nucleotide can be (Continued)

detected upon incorporation of the individual tagged nucleotide. The tag can be detected with the aid of the nanopore when the tag is released from the nucleotide.

19 Claims, 49 Drawing Sheets

Specification includes a Sequence Listing.

Related U.S. Application Data

(60) Provisional application No. 61/880,407, filed on Sep. 20, 2013, provisional application No. 61/737,621, filed on Dec. 14, 2012, provisional application No. 61/724,869, filed on Nov. 9, 2012.

(51) Int. Cl.
  G01N 27/447 (2006.01)
  G01N 33/487 (2006.01)

(56) References Cited

U.S. PATENT DOCUMENTS

| | | |
|---|---|---|
| 5,302,509 A | 4/1994 | Cheeseman |
| 5,308,539 A | 5/1994 | Koden et al. |
| 5,457,342 A | 10/1995 | Herbst, II |
| 5,569,950 A | 10/1996 | Lewis et al. |
| 5,576,204 A | 11/1996 | Blanco et al. |
| 5,756,355 A | 5/1998 | Lang et al. |
| 5,770,367 A | 6/1998 | Southern et al. |
| 5,795,782 A | 8/1998 | Church et al. |
| 5,804,386 A | 9/1998 | Ju |
| 5,814,454 A | 9/1998 | Ju |
| 5,869,244 A | 2/1999 | Martin et al. |
| 5,876,936 A | 3/1999 | Ju |
| 5,912,155 A | 6/1999 | Chatterjee et al. |
| 5,939,301 A | 8/1999 | Hughes, Jr. et al. |
| 5,952,180 A | 9/1999 | Ju |
| 5,981,733 A | 11/1999 | Gamble et al. |
| 6,012,291 A | 1/2000 | Ema |
| 6,014,213 A | 1/2000 | Waterhouse et al. |
| 6,015,714 A | 1/2000 | Baldarelli et al. |
| 6,046,005 A | 4/2000 | Ju et al. |
| 6,082,115 A | 7/2000 | Strnad |
| 6,210,896 B1 | 4/2001 | Chan |
| 6,217,731 B1 | 4/2001 | Kane et al. |
| 6,232,103 B1 | 5/2001 | Short |
| 6,255,083 B1 | 7/2001 | Williams |
| 6,261,797 B1 | 7/2001 | Sorge et al. |
| 6,265,193 B1 | 7/2001 | Brandis et al. |
| 6,321,101 B1 | 11/2001 | Holmstrom |
| 6,362,002 B1 | 3/2002 | Denison et al. |
| 6,383,749 B2 | 5/2002 | Bochkariov et al. |
| 6,399,320 B1 | 6/2002 | Markau et al. |
| 6,399,335 B1 | 6/2002 | Kao et al. |
| 6,413,792 B1 | 7/2002 | Sauer et al. |
| 6,485,703 B1 | 11/2002 | Cote et al. |
| 6,607,883 B1 | 8/2003 | Frey et al. |
| 6,616,895 B2 | 9/2003 | Dugas et al. |
| 6,627,748 B1 | 9/2003 | Ju et al. |
| 6,664,079 B2 | 12/2003 | Ju et al. |
| 6,673,615 B2 | 1/2004 | Denison et al. |
| 6,686,997 B1 | 2/2004 | Allen |
| 6,699,719 B2 | 3/2004 | Yamazaki et al. |
| 6,723,513 B2 | 4/2004 | Lexow |
| 6,746,594 B2 | 6/2004 | Akeson et al. |
| 6,762,048 B2 | 7/2004 | Williams |
| 6,800,933 B1 | 10/2004 | Mathews et al. |
| 6,824,659 B2 | 11/2004 | Bayley et al. |
| 6,880,346 B1 | 4/2005 | Tseng et al. |
| 6,891,278 B2 | 5/2005 | Muller et al. |
| 6,916,665 B2 | 7/2005 | Bayley et al. |
| 6,952,651 B2 | 10/2005 | Su |
| 7,033,762 B2 | 4/2006 | Nelson et al. |
| 7,041,812 B2 | 5/2006 | Kumar et al. |
| 7,052,839 B2 | 5/2006 | Nelson et al. |
| 7,057,026 B2 | 6/2006 | Barnes et al. |
| 7,074,597 B2 | 7/2006 | Ju |
| 7,153,672 B1 | 12/2006 | Eickbush et al. |
| 7,189,503 B2 | 3/2007 | Akeson et al. |
| 7,223,541 B2 | 5/2007 | Fuller et al. |
| 7,229,799 B2 | 6/2007 | Williams |
| 7,233,541 B2 | 6/2007 | Yamamoto et al. |
| 7,238,485 B2 | 7/2007 | Akeson et al. |
| 7,244,602 B2 | 7/2007 | Frey et al. |
| 7,279,337 B2 | 10/2007 | Zhu |
| 7,321,329 B2 | 1/2008 | Tooyama et al. |
| 7,345,159 B2 | 3/2008 | Ju et al. |
| 7,361,466 B2 | 4/2008 | Korlach et al. |
| 7,368,668 B2 | 5/2008 | Ren et al. |
| 7,405,281 B2 | 7/2008 | Xu et al. |
| 7,446,017 B2 | 11/2008 | Liu et al. |
| 7,452,698 B2 | 11/2008 | Sood et al. |
| 7,622,279 B2 | 11/2009 | Ju |
| 7,622,934 B2 | 11/2009 | Hibbs et al. |
| 7,625,701 B2 | 12/2009 | Williams et al. |
| 7,626,379 B2 | 12/2009 | Peters et al. |
| 7,635,578 B2 | 12/2009 | Ju et al. |
| 7,710,479 B2 | 5/2010 | Nitta et al. |
| 7,713,698 B2 | 5/2010 | Ju et al. |
| 7,727,722 B2 | 6/2010 | Nelson et al. |
| 7,745,116 B2 | 6/2010 | Williams |
| 7,777,013 B2 | 8/2010 | Xu et al. |
| 7,777,505 B2 | 8/2010 | White et al. |
| 7,790,869 B2 | 9/2010 | Ju et al. |
| 7,871,777 B2 | 1/2011 | Schneider et al. |
| 7,883,869 B2 | 2/2011 | Ju et al. |
| 7,897,738 B2 | 3/2011 | Brandis et al. |
| 7,906,371 B2 | 3/2011 | Kim et al. |
| 7,924,335 B2 | 4/2011 | Itakura et al. |
| 7,939,259 B2 | 5/2011 | Kokoris et al. |
| 7,939,270 B2 | 5/2011 | Holden et al. |
| 7,947,454 B2 | 5/2011 | Akeson et al. |
| 7,948,015 B2 | 5/2011 | Rothberg et al. |
| 7,973,146 B2 | 7/2011 | Shen et al. |
| 7,982,029 B2 | 7/2011 | Ju et al. |
| 7,989,928 B2 | 8/2011 | Liao et al. |
| 8,022,511 B2 | 9/2011 | Chiu et al. |
| 8,058,030 B2 | 11/2011 | Smith et al. |
| 8,058,031 B2 | 11/2011 | Xu et al. |
| 8,058,414 B2 | 11/2011 | Menchen et al. |
| 8,088,575 B2 | 1/2012 | Ju et al. |
| 8,133,672 B2 | 3/2012 | Bjornson et al. |
| 8,137,569 B2 | 3/2012 | Harnack et al. |
| 8,148,516 B2 | 4/2012 | Williams et al. |
| 8,252,911 B2 | 8/2012 | Bjornson et al. |
| 8,257,954 B2 | 9/2012 | Clark et al. |
| 8,298,792 B2 | 10/2012 | Ju et al. |
| 8,324,914 B2 | 12/2012 | Chen et al. |
| 8,461,854 B2 | 6/2013 | Chen et al. |
| 8,541,849 B2 | 9/2013 | Chen |
| 9,528,151 B2 | 12/2016 | Ju et al. |
| 9,624,539 B2 | 4/2017 | Ju et al. |
| 9,670,539 B2 | 6/2017 | Ju et al. |
| 9,708,358 B2 | 7/2017 | Ju et al. |
| 9,718,852 B2 | 8/2017 | Ju et al. |
| 9,719,139 B2 | 8/2017 | Ju et al. |
| 9,725,480 B2 | 8/2017 | Ju et al. |
| 9,868,985 B2 | 1/2018 | Ju et al. |
| 9,890,426 B2 | 2/2018 | Ju et al. |
| 10,000,801 B2 | 6/2018 | Ju et al. |
| 10,144,961 B2 | 12/2018 | Ju et al. |
| 10,240,195 B2 | 3/2019 | Fuller et al. |
| 10,246,479 B2 | 4/2019 | Ju et al. |
| 10,260,094 B2 | 4/2019 | Ju et al. |
| 2003/0027140 A1 | 2/2003 | Ju et al. |
| 2003/0054360 A1 | 3/2003 | Gold et al. |
| 2003/0101006 A1 | 5/2003 | Mansky et al. |
| 2003/0166282 A1 | 9/2003 | Brown et al. |
| 2003/0198982 A1 | 10/2003 | Seela et al. |
| 2004/0122335 A1 | 6/2004 | Sackellares et al. |
| 2004/0185466 A1 | 9/2004 | Ju et al. |
| 2005/0032081 A1 | 2/2005 | Ju et al. |

(56) References Cited

U.S. PATENT DOCUMENTS

| | | |
|---|---|---|
| 2005/0091989 A1 | 5/2005 | Leija et al. |
| 2005/0127035 A1 | 6/2005 | Ling |
| 2005/0186576 A1 | 8/2005 | Chan et al. |
| 2005/0208574 A1 | 9/2005 | Bayley et al. |
| 2005/0221351 A1 | 10/2005 | Ryu |
| 2005/0239194 A1 | 10/2005 | Takahashi et al. |
| 2006/0057565 A1 | 3/2006 | Ju et al. |
| 2006/0105461 A1 | 5/2006 | Tom-Moy et al. |
| 2006/0115951 A1 | 6/2006 | Mosley |
| 2006/0252038 A1 | 11/2006 | Ju |
| 2006/0278992 A1 | 12/2006 | Trezza et al. |
| 2007/0173731 A1 | 7/2007 | Meka et al. |
| 2007/0190542 A1 | 8/2007 | Ling et al. |
| 2007/0196846 A1 | 8/2007 | Hanzel et al. |
| 2007/0275387 A1 | 11/2007 | Ju |
| 2008/0101988 A1 | 5/2008 | Kang et al. |
| 2008/0108082 A1 | 5/2008 | Rank et al. |
| 2008/0199932 A1 | 8/2008 | Hanzel et al. |
| 2008/0218184 A1 | 9/2008 | White et al. |
| 2008/0221806 A1 | 9/2008 | Bryant et al. |
| 2008/0286768 A1 | 11/2008 | Lexow |
| 2008/0318245 A1 | 12/2008 | Smirnov |
| 2009/0029477 A1 | 1/2009 | Meller et al. |
| 2009/0066315 A1 | 3/2009 | Hu et al. |
| 2009/0073293 A1 | 3/2009 | Yaffe et al. |
| 2009/0087834 A1 | 4/2009 | Lexow et al. |
| 2009/0099786 A1 | 4/2009 | Oliver et al. |
| 2009/0102534 A1 | 4/2009 | Schmid et al. |
| 2009/0136958 A1 | 5/2009 | Gershow et al. |
| 2009/0167288 A1 | 7/2009 | Reid et al. |
| 2009/0215050 A1 | 8/2009 | Jenison |
| 2009/0263791 A1 | 10/2009 | Ju et al. |
| 2009/0269759 A1 | 10/2009 | Menchen, Jr. et al. |
| 2009/0298072 A1 | 12/2009 | Ju |
| 2009/0325154 A1 | 12/2009 | Ju et al. |
| 2010/0025238 A1 | 2/2010 | Gottlieb et al. |
| 2010/0025249 A1 | 2/2010 | Polonsky et al. |
| 2010/0035260 A1 | 2/2010 | Olasagasti et al. |
| 2010/0047802 A1 | 2/2010 | Bjorson et al. |
| 2010/0072080 A1 | 3/2010 | Karhanek et al. |
| 2010/0075328 A1 | 3/2010 | Bjornson et al. |
| 2010/0075332 A1 | 3/2010 | Patel et al. |
| 2010/0078777 A1 | 4/2010 | Barth et al. |
| 2010/0092952 A1 | 4/2010 | Ju et al. |
| 2010/0093555 A1 | 4/2010 | Bjornson et al. |
| 2010/0093992 A1 | 4/2010 | Cherkasov et al. |
| 2010/0109197 A1 | 5/2010 | Hansen et al. |
| 2010/0121582 A1 | 5/2010 | Pan et al. |
| 2010/0122907 A1 | 5/2010 | Stanford et al. |
| 2010/0129842 A1 | 5/2010 | Pappin et al. |
| 2010/0148126 A1 | 6/2010 | Guan et al. |
| 2010/0196203 A1 | 8/2010 | Sanghera et al. |
| 2010/0243449 A1 | 9/2010 | Oliver |
| 2010/0261247 A1 | 10/2010 | Hanzel et al. |
| 2010/0292101 A1 | 11/2010 | So |
| 2010/0297644 A1 | 11/2010 | Kokoris et al. |
| 2010/0301398 A1 | 12/2010 | Rothberg et al. |
| 2010/0304381 A1 | 12/2010 | Taing et al. |
| 2010/0320094 A1 | 12/2010 | White et al. |
| 2010/0331194 A1 | 12/2010 | Turner et al. |
| 2011/0005918 A1 | 1/2011 | Akeson et al. |
| 2011/0014601 A2 | 1/2011 | Carroll et al. |
| 2011/0014611 A1 | 1/2011 | Ju et al. |
| 2011/0039259 A1 | 2/2011 | Ju et al. |
| 2011/0053284 A1 | 3/2011 | Meller et al. |
| 2011/0059505 A1 | 3/2011 | Hanzel et al. |
| 2011/0160093 A1 | 6/2011 | Van Den Boom et al. |
| 2011/0165652 A1 | 7/2011 | Hardin et al. |
| 2011/0168968 A1 | 7/2011 | Yang et al. |
| 2011/0174625 A1 | 7/2011 | Akeson et al. |
| 2011/0189659 A1 | 8/2011 | Clark et al. |
| 2011/0192723 A1 | 8/2011 | Chen et al. |
| 2011/0193249 A1 | 8/2011 | Chen et al. |
| 2011/0193570 A1 | 8/2011 | Chen et al. |
| 2011/0218414 A1 | 9/2011 | Kamath et al. |
| 2011/0229877 A1* | 9/2011 | Jayasinghe ............ C12N 9/127 435/6.1 |
| 2011/0244447 A1 | 10/2011 | Korlach |
| 2011/0287414 A1 | 11/2011 | Chen et al. |
| 2012/0034602 A1 | 2/2012 | Emig et al. |
| 2012/0040869 A1 | 2/2012 | Meller et al. |
| 2012/0052188 A1 | 3/2012 | Chen et al. |
| 2012/0094278 A1 | 4/2012 | Akeson et al. |
| 2012/0094332 A1 | 4/2012 | Lee et al. |
| 2012/0115736 A1 | 5/2012 | Bjornson et al. |
| 2012/0142006 A1 | 6/2012 | Ju et al. |
| 2012/0149021 A1 | 6/2012 | Yung et al. |
| 2012/0156680 A1 | 6/2012 | Ju et al. |
| 2012/0160681 A1 | 6/2012 | Davis et al. |
| 2012/0160687 A1 | 6/2012 | Akeson et al. |
| 2012/0160688 A1 | 6/2012 | Davis et al. |
| 2012/0187963 A1 | 7/2012 | Chen |
| 2012/0188092 A1 | 7/2012 | Chen |
| 2012/0196759 A1 | 8/2012 | Chen |
| 2012/0261261 A1 | 10/2012 | Huber |
| 2013/0015068 A1 | 1/2013 | Chen et al. |
| 2013/0207205 A1 | 8/2013 | Chen |
| 2013/0237460 A1 | 9/2013 | Deierling et al. |
| 2013/0240359 A1 | 9/2013 | Turner et al. |
| 2013/0244340 A1 | 9/2013 | Davis et al. |
| 2013/0263946 A1 | 10/2013 | Afzali-Ardakani et al. |
| 2013/0264207 A1 | 10/2013 | Ju et al. |
| 2013/0280700 A1 | 10/2013 | Ju et al. |
| 2014/0014513 A1 | 1/2014 | Chen et al. |
| 2014/0034497 A1 | 2/2014 | Davis et al. |
| 2014/0093869 A1 | 4/2014 | Ju et al. |
| 2015/0197800 A1 | 7/2015 | Ju et al. |
| 2016/0076092 A1 | 3/2016 | Jayasinghe et al. |
| 2016/0264612 A1 | 9/2016 | Ju et al. |
| 2017/0058335 A1 | 3/2017 | Tao et al. |
| 2017/0283451 A1 | 10/2017 | Ju et al. |
| 2018/0030524 A1 | 2/2018 | Davis et al. |
| 2018/0073071 A1 | 3/2018 | Ju et al. |
| 2018/0112257 A1 | 4/2018 | Ju et al. |
| 2018/0201642 A1 | 7/2018 | Ju et al. |
| 2018/0274024 A1 | 9/2018 | Ju et al. |
| 2018/0327828 A1 | 11/2018 | Ju et al. |
| 2019/0031704 A1 | 1/2019 | Ju et al. |
| 2019/0031705 A1 | 1/2019 | Ju et al. |
| 2019/0031706 A1 | 1/2019 | Ju et al. |
| 2019/0085014 A1 | 3/2019 | Ju et al. |
| 2019/0085015 A1 | 3/2019 | Ju et al. |
| 2019/0085016 A1 | 3/2019 | Ju et al. |
| 2019/0085388 A1 | 3/2019 | Ju et al. |
| 2019/0092805 A1 | 3/2019 | Ju et al. |
| 2019/0092806 A1 | 3/2019 | Ju et al. |
| 2019/0112650 A1 | 4/2019 | Ju et al. |
| 2019/0135850 A1 | 5/2019 | Ju et al. |
| 2019/0135851 A1 | 5/2019 | Ju et al. |
| 2019/0136308 A1 | 5/2019 | Ju et al. |
| 2019/0153527 A1 | 5/2019 | Ju et al. |

FOREIGN PATENT DOCUMENTS

| | | |
|---|---|---|
| WO | WO 1997/032999 | 9/1997 |
| WO | WO 1997/046704 | 12/1997 |
| WO | WO 2001/048235 | 7/2001 |
| WO | WO 2002/022883 | 3/2002 |
| WO | WO 2002/029003 | 4/2002 |
| WO | WO 2002/079519 | 10/2002 |
| WO | WO 2003/020734 | 3/2003 |
| WO | WO 2004/007773 | 1/2004 |
| WO | WO 2004/055160 | 7/2004 |
| WO | WO 2004/071155 | 8/2004 |
| WO | WO 2004/072238 | 8/2004 |
| WO | WO 2004/090154 | 10/2004 |
| WO | WO 2005/084367 | 9/2005 |
| WO | WO 2006/020775 | 2/2006 |
| WO | WO 2007/053702 | 5/2007 |
| WO | WO 2007/053719 | 5/2007 |
| WO | WO 2007/127327 | 11/2007 |
| WO | WO 2007/146158 | 12/2007 |
| WO | WO 2008/034602 | 3/2008 |
| WO | WO 2008/069973 | 6/2008 |

(56) References Cited

FOREIGN PATENT DOCUMENTS

| WO | WO 2008/102120 | 8/2008 |
|---|---|---|
| WO | WO 2008/124107 | 10/2008 |
| WO | WO 2009/020682 | 2/2009 |
| WO | WO 2009/051807 | 4/2009 |
| WO | WO 2009/054922 | 4/2009 |
| WO | WO 2010/109197 | 9/2010 |
| WO | WO 2011/038241 | 3/2011 |
| WO | WO 2011/067559 | 6/2011 |
| WO | WO 2011/097028 | 8/2011 |
| WO | WO 2011/106459 | 9/2011 |
| WO | WO 2012/009578 | 1/2012 |
| WO | WO 2012/088339 | 6/2012 |
| WO | WO 2012/088341 | 6/2012 |
| WO | WO 2012/121756 | 9/2012 |
| WO | WO 2013/016486 | 1/2013 |
| WO | WO 2013/109970 | 7/2013 |
| WO | WO 2013/154999 | 10/2013 |
| WO | WO 2013/191793 | 12/2013 |
| WO | WO 2017/058953 | 4/2017 |
| WO | WO 2017/087887 | 5/2017 |
| WO | WO 2017/176677 | 10/2017 |
| WO | WO 2017/176679 | 10/2017 |
| WO | WO 2017/205336 | 11/2017 |
| WO | WO 2018/183538 | 10/2018 |

OTHER PUBLICATIONS

Li et al. (2003) "A photocleavable Fluorescent Nucleotide for DNA Sequencing and Analysis," PNAS 100 (2) :414-419.

Linear Technology, High Efficiency Thermoelectric Cooler Controller, 2001.

Low Noise, Dual Switched Integrator, Burr-Brown Corporation, Sep. 1994.

Lundquist, J.T. et al (2002) "A New Tri-Orthogonal Strategy for Peptide Cyclization" Org. Lett. 4 (19) :3219-3221.

Madampage, et al. Nanopore detection of antibody prion interactions. Anal Biochem. Jan. 1, 2010; 396(1) :36-41. Epub Aug. 21, 2009.

Mathe, J. et al. (2004) "Nanopore Unzipping of Individual Hairpin Molecules" Biophysical Journal 87:3205-3212.

Mathe, et al. Orientation discrimination of single-stranded DNA inside the alpha-hemolysin membrane channel. PNAS USA. Aug. 30, 2005;102 (35) :12377-82. Epub Aug. 19, 2005.

Mauer et al. Reconstitution of ion channels in agarose-supported silicon orifices. Biosens Bioelectron. May 15, 2007; 22 (11) :2577-84. Epub Nov. 13, 2006.

McGuigan, et al. "DNA fingerprinting by sampled sequencing." Methods in Enzymology. 1993;218:241-258.

McNally, et al. Optical recognition of converted DNA nucleotides for single-molecule DNA sequencing using nanopore arrays. Nano Lett. Jun. 9, 2010; 10 (6) 2237-44.

Meller, A. et al. (2000) "Rapid nanopore discrimination between single polynucleotide molecules." Proc. Natl. Acad. Sci. USA 97:1079-1084.

Meller, A. et al. (2002) "Single Molecule Measurements of DNA Transport Through a Nanopore" Electrophoresis 23:2583-2591.

Mohammad et al. Controlling a single protein in a nanopore through electrostatic traps. J Am Chem Soc. Mar. 26, 2008; 130 (12) :4081-8. Epub Mar. 6, 2008.

Movileanu, et al. Partitioning of polymer into a nanoscopic protein pore obeys a simple scaling law. PNAS USA Aug. 28, 2001;98 (18) :10137-41. Epub Aug. 14, 2001.

Movileanu, et al. Partitioning of individual flexible polymers into a nanoscopic protein pore. Biophys J. Aug. 2003;85 (2) :897-910.

Mulder et al. (2005) "Nucleotide modification at the γ-phosphate leads to the improved fidelity of HIV-1 reverse transcriptase", Nucleic Acids Research, 33 (15) :4865-4873.

Nakane et al. A Nanosensor for Transmembrane Capture and Identification of Single Nucleic Acid Molecules, Biophysical Journal, vol. 87, Issue 1, Jul. 2004, pp. 615-621, ISSN 0006-3495.

Park et al. DNA hybridization sensors based on electrochemical impedance spectroscopy as a detection tool. Sensors (Basel). 2009; 9 (12) :9513-32. Epub Nov. 26, 2009.

Perkins, T.T. et al. (1994) "Relaxation of a single DNA molecule observed by optical microscopy" Science 264:822-826.

Pourmand N. et al. (2002) "Multiplex Pyrosequencing" Nucleic Acids Research 30 (7) :1-5.

Purnell et al. Discrimination of single base substitutions in a DNA strand immobilized in a biological nanopore. ACS Nano. Sep. 22, 2009; 3 (9) :2533-8.

Reiner, et al. "Temperature sculpting in yoctoliter volumes." J Am Chem Soc. Feb. 27, 2013;135 (8) :3087-94. Doi:10/1021/ja309892e. Epub Feb. 14, 2013.

Reiner, et al. 37 Theory for polymer analysis using nanopore-based single-molecule mass spectrometry. PNAS USA. Jul. 6, 2010;107 (27) :12080-5. Doi:10/1073/PNAS.1002194107. Epub Jun. 21, 2010.

Reynolds et al. (2008) "Synthesis and Stability of Novel Terminal Phosphate-labeled Nucleotides", Nucleosides, Nucleotides, and Nucleic Acids, 27(1):18-30.

Rief M. (1999) "Sequence-dependent mechanics of single DNA molecules" Mat. Struct. Biol. 6:346-349.

Robertson et al., (2007) "Single-Molecule Mass Spectrometry in Solution Using a Solitary Nanopore" PNAS, 104(20):8207-8211.

Rosenblum, B.B. et al. (1997) "New dye-labeled terminators for improved DNA sequencing patterns," Nucleic Acids Res. 25:4500-4504.

Rosenstein, et al. Integrated nanopore sensing platform with sub-microsecond temporal resolution. Nat Methods. Mar. 18, 2012;9(5) :487-92. Doi: 10.1038/nmeth.1932.

Rostovstev, V.V. et al. (2002) "A stepwise huisgen cycloaddition process: copper(I)-catalyzed regioselective "ligation" of azides and terminal alkynes." Angew. Chem. Int. Ed. 41 (14) :2596-2599.

Rotem et al., Temperature Measurement in the Intel Core Duo Processor, 2007.

Saleh, et al. Direct detection of antibody-antigen binding using an on-chip artificial pore. PNAS USA. Feb. 4, 2003;100 (3) :820-4. Epub Jan. 27, 2003.

Sanchez-Magraner, et al. Membrane insertion of *Escherichia coli* alpha-hemolysin is independent from membrane lysis. J Biol Chem. Mar. 3, 2006; 281 (9) :5461-7. Epub Dec. 22, 2005.

Sauer-Budge, A.F. et al. (2003) "Unzipping Kinetics of Double Stranded DNA in a Nanopore" Physical Review Letters 90 (23) :238101-1-238101-4.

Schneider et al. "DNA sequencing with nanopores." Nat Biotechnol. Apr. 10, 2012;30(4):326-8. Doi10/1038/nbt/2181.

Seo et al., (2004) "Photocleavable Fluorescent Nucleotides for DNA Sequencing on a Chip Constructed by Site-Specific Coupling Chemistry," PNAS 101 (15) :5488-5493.

Shim et al., Encapsulating a single G-quadruplex aptamer in a protein nanocavity. J Phys Chem B. Jul. 17, 2008; 112 (28) :8354-60. Epub Jun. 19, 2008.

Simon et al., Formation and stability of a suspended biomimetic lipid bilayer on silicon submicrometer-sized pores. J Colloid Interface Sci. Apr. 15, 2007; 308 (2) :337-43. Epub Jan. 31, 2007.

Singer et al. Nanopore Based Sequence Specific Detection of Duplex DNA for Genomic Profiling, Jan. 8, 2010, published Jan. 20, 2010, pp. 738-742.

Singh et al. (2001) "Synthesis of natural flutimide and analogous fully substituted pyrazine-2,6-diones, endonuclease inhibitors of influenza virus" J. Org. Chem. 66 (16) :5504-5516.

Smith, S.B. et al. (1996) "Overstretching B-DNA: the elastic response of individual double-stranded and single-stranded DNA molecules." Science 271:795-799.

Sood et al. (2005) "Terminal phosphate-labeled nucleotides with improved substrate properties for homogenous nucleic acid assays", JACS, 127 (8) :2394-2395.

Stanford, et al. Using HMMs to Quantify Signals from DNA Driven Through a Nanometer-Scale Pore. IEEE Workshop on Genomic Signal Processing and Statistics. Raleigh, NC. Oct. 2002; 11-13.

Sterfureac et al. Transport of alpha-helical peptides through alpha-hemolysin and aerolysin pores. Biochemistry. Aug. 1, 2006; 45 (30) :9172-9.

(56) References Cited

OTHER PUBLICATIONS

Stefureac et al. Nanopore analysis of the interaction of metal ions with prion proteins and peptides. Biochem Cell Biol. Apr. 2010; 88 (2) :347-58.
Stoddart et al. Single-nucleotide discrimination in immobilized DNA oligonucleotides with a biological nanopore. Proc Natl Acad Sci U S A. May 12, 2009;106 (19) :7702-7. doi: 10.1073/pnas. 0901054106. Epub Apr. 20, 2009.
Stoddart et al. Nucleobase recognition in ssDNA at the central constriction of the alpha-hemolysin pore. Nano Lett. Sep. 8, 2010; 10 (9) :3633-7.
Storm, et al. "Translocation of double-stranded DNA through a silicon oxide nanopore." Phys Rev E Stat Nonlin Soft Matter Phys. May 2005;71 (5 Pt 1) :051903. Epub May 6, 2005.
Streater M et al., (Novel 3-hydroxy-2 (IH)-pyridinones. Synthesis, iron (III)-chelating properties, and biological activity. J. Medicinal Chem. (1990) 33 (6) :1749-1755.
Studer et al., Formation of individual protein channels in lipid bilayers suspended in nanopores. Colloids Surf B Biointerfaces., Oct. 15, 2009; 73 (2) :325-31. Epub Jun. 10, 2009.
Suzuki et al., Highly reproducible method of planar lipid bilayer reconstitution in polymethyl methacrylate microfluidic chip. , Feb. 2006, Langmuir. 22 (4) :1937-42.
Thomson et al., Preliminary nanopore cheminformatics analysis of aptamer-target binding strength, Nov. 2007, BMC Bioinformatics. 1; 8 Suppl 7:S11.
Venkatesan, et al. "Nanopore sensors for nucleic acid analysis." Nat Nanotechnology Sep. 18, 2011;6 (10) :615-24. Doi: 10/1038/nnano 2011.129.
Vercoutere W. et al., "Rapid discrimination among individual DNA hairpin molecules at single-nucleotide resolution using an ion channel.", 2001, Nat. Biotech 19:248-252.
Vercoutere W. et al., "Discrimination Among Individual Watson-Crick Bsae Pairs at the Termini of Single DNA Hairpin Molecules", 2003, Nucleic Acids Research 31 (4) :1311-1318.
Viasnoff et al., Probing DNA base pairing energy profiles using a nanopore. Eur Biophys J., Feb. 2009, 38(2):263-9. Epub Oct. 3, 2008.
Wang H. et al., (2004) "DNA heterogeneity and Phosphorylation unveiled by Single-Molecule Electrophoresis" Proc. Natl. Acad. Sci. USA 101 (37) :13472-13477.
Wanunu et al., DNA profiling using solid-state nanopores: detection of DNA-binding molecules. Nano Lett. Oct. 2009; 9 (10) :3498-502.
Weng et al., Fluid biomembranes supported on nanoporous aerogel/xerogel substrates. Langmuir. Aug. 17, 2004; 20 (17) :7232-9.
Wilson et al. Feedback control of a DNA molecule tethered in a nanopore to repeatedly probe DNA-binding enzymes. Conf Proc IEEE Eng Med Biol Soc. 2008; 2008:5745-8.
Winters-Hilt et al., Nanopore-based kinetics analysis of individual antibody-channel and antibody-antigen interactions. BMC Bioinformatics. Nov. 1, 2007; 8 Suppl 7:S20.
Woodside et al., Nanomechanical measurements of the sequence-dependent folding landscapes of single nucleic acid hairpins. Proc Natl Acad Sci U S A. Apr. 18, 2006; 103 (16) :6190-5. Epub Apr. 10, 2006.
Woodside et al., Direct measurement of the full, sequence-dependent folding landscape of a nucleic acid. Science. Nov. 10, 2006; 314 (5801) :1001-4.
Wu et al., Single-molecule detection of nitrogen mustards by covalent reaction within a protein nanopore. J Am Chem Soc. May 28, 2008; 130 (21) :6813-9. Epub Apr. 30, 2008.
Zeineldin et al., Using bicellular mixtures to form supported and suspended lipid bilayers on silicon chips. Langmuir. Sep. 12, 2006; 22 (19) :8163-8.
Zwolak, et al. Electronic signature of DNA nucleotides via transverse transport. Nano Lett. Mar. 2005; 5 (3) :421-4.
Akeson, M., Branton, D., Kasianowicz , J.J. , Brandin, E., and Deamer, D.W. (1999) "Microsecond time-scale discrimination between polycytidylic acid and polyadenylic acid segments wtihin single RNA molecules" Biophys. J. 77:3227-3233.
Askimentiev, A. et al. (2004) "Microscopic Kinetics of DNA Translocation through Synthetic Nanopores" Biophysical Journal 87:2086-2097.
Andersen, Sequencing and the single channel. Biophys J. Dec. 1999; 77 (6) :2899-901.
Ashkenasy et al. Recognizing a single base in an individual DNA strand: a step toward DNA sequencing in nanopores . Angew Chem Int Ed Engl. Feb. 18, 2005; 44 (9) :1401-4.
Atanasnov et al. Membrane on a chip: a functional tethered lipid bilayer membrane on silicon oxide surfaces. Biophys J. Sep. 2005; 89 (3) :1780-8.
Baaken et al. Planar microelectrode-cavity array for high-resolution and parallel electrical recording of membrane ionic currents. Lab Chip. Jun. 2008; 8 (6) : 938-44 . Epub Apr. 16, 2008.
Bai, X., Kim, S., Li, Z., Turro, N.J. and Ju, J. (2004) "Design and Synthesis of a Photocleavable Biotinylated Nucleotide for DNA Analysis by Mass Spectrometry," Nucleic Acids Research, 32 (2) :534-541.
Benner, et al. Sequence-specific detection of individual DNA polymerase complexes in real time using a nanopore. Nat Nanotechnol. Nov. 2007; 2 (11) :718-24 . Epub Oct. 28, 2007.
Bezrukov, et al., "Dynamic partitioning of neutral polymers moving through a single ion channel." Nature. Jul. 28, 1994; 370 (6687) :279-81.
Bezrukov, et al., "Dynamics and free energy of polymers partitioning into a nanoscale pore." Macromolecules. 1996; 29:8517-8522.
Bezrukov, S.M., and Kasianowicz, J.J. (2001) "Neutral Polymers in the nanopores of alamethicin and alpha-hemolysin." Biologicheskie Membrany 18:451-455.
Boireau et al. Unique supramolecular assembly of a redox protein with nucleic acids onto hybrid bilayer: towards a dynamic DNA chip. Biosens Bioelectron. Feb. 15, 2005; 20 (8) :1631-7.
Bokhari, S.H. et al. (2005) "A Parallel Graph Decomposition Algorithm for DNA Sequencing with Nanopores" Bioinformatics 21 (7) :889-896.
Buchmann, et al. Electrochemical release from gold-thiolate electrodes for controlled insertion of ion channels into bilayer membranes. Bioorg Med Chem. Mar. 15, 2004; 12 (6) :1315-24.
Butler, et al. Determination of RNA orientation during translocation through a biological nanopore. Biophys J. Jan. 1, 2006; 90 (1) :190-9. Epub Oct. 7, 2005.
Butler, et al. Ionic current blockades from DNA and RNA molecules in the alpha-hemolysin nanopore. Biophys J. Nov. 1, 2007; 93 (9) :3229-40. Epub Aug. 3, 2007.
Butler, et al. Single-molecule DNA detection with an engineered MspA protein nanopore. Proceedings of the National Academy of Science USA. Dec. 30, 2008;105 (52) :20647-52, Epub Dec. 19, 2008.
Chandler, E.L et al. (2004) "Membrane Surface Dynamics of DNA-Threaded Nanopores Revealed by Simultaneous Single-Molecule Optical and Ensemble Electrical Recording." Langmuir 20:898-905.
Churbanov, et al., "Duration learning for analysis of nanopore ionic current blockades." BMC Bioinformatics. Nov. 1, 2007;8 Suppl. 7:S14.
Clarke, et al. "Continuous base identification for single-molecule nanopore DNA sequencing" Nat Nanotechnol. Apr. 2009; 4 (4) :265-70. Epub Feb. 22, 2009.
Cockroft, et al. A single-molecule nanopore device detects DNA polymerase activity with single-nucleotide resolution. J Am Chem Soc. Jan. 23, 2008; 130 (3) :818-20. Epub Jan. 1, 2008.
Danleon, et al. Cell membranes suspended across nanoaperture arrays. Langmuir. Jan. 3, 2006; 22 (1) :22-5.
Deamer, D.W. et al (2002) "Characterization of nucleic acids by nanopore analysis." Acc. Chem. Res. 35 (10) :817-825.
Derrington, et al. Nanopore DNA sequencing with MspA. PNAS USA. Sep. 14, 2010;107 (37) :16060-5. Epub Aug. 26, 2010.
Eid et al. (2009) "Real-Time DNA Sequencing from Single Polymerase Molecules", Science, 23 (5910) :133-138.
Einstein. "Investigations on the theory of Brownian movement", Dover, New York. 1956.

(56) References Cited

OTHER PUBLICATIONS

Ervin, et al. Simultaneous alternating and direct current readout of protein ion channel blocking events using glass nanopore membranes. Anal Chem. Mar. 15, 2008; 80 (6) :2069-76. Epub Feb. 23, 2008.
Flusberg, et al. Direct detection of DNA methylation during single-molecule, real-time sequencing. Nat Methods. Jun. 2010; 7 (6) :461-5. Epub May 9, 2010.
Fologea, D. et al. (2005) "Slowing DNA Translocation in a Solid State Nanopore" Nano Letters 5 (9) , 1734-1737.
Fologea, D. et al. (2005) "Detecting Single Stranded DNA with a Solid State Nanopore" Nano Letters 5 (10) :1905-1909.
Gu, et al. Stochastic sensing of organic analytes by a pore-forming protein containing a molecular adapter. Nature. Apr. 22, 1999;398 (6729) :686-90.
Guo et al., "An Integrated System for DNA Sequencing by Synthesis Using Novel Nucleotide Analogues", Accounts of Chem. Res. vol. 43, No. 4, Apr. 20, 2010, pp. 551-563, XP55032473, ISSN: 0001-4842, DOI: 10.1021/ar900255c.
Guranowski et al., (2000) "Selective Degradation of 2'—Adenlyated Diadenosine Tri- and Tetraphosphates, Ap3A and Ap4A, by Two Specific Human Dinucleoside Polyphosphate Hydrolases", Archives of Biochemistry and Biophysics, 373 (1) :218-224.
Haas, et al. "Improvement of the quality of self assembled bilayer lipid membranes by using a negative potential." Biochemistry. Aug. 2001;54 (1) :1-10.
Halverson, et al. "Asymmetric blockade of anthrax protective antigen ion channel asymmetric blockade." J. Biol. Chem. Oct. 7, 2005;280 (40) :34056-62. Epub Aug. 8, 2005.
Harlepp, et al. Probing complex RNA structures by mechanical force. Eur Phys J E Soft Matter. Dec. 2003; 12 (4) :605-15.
Heins, et al. Detecting single porphyrin molecules in a conically shaped synthetic nanopore. Nano Lett. Sep. 2005;5 ( () :1824-9.
Heng, J.B. et al. (2005) "Stretching DNA Using the Electric Field in a Synthetic Nanopore" Nano Letters 5 (9) :1734-1737.
Heng, J.B. et al. (2006) "The Electromechanics of DNA in a synthetic nanopore" Biophysical Journal 90:1098-1106.
Henrickson, S.E. et al (2000) "Driven DNA Transport into an Asymmetric Nanometer-scale Pore" Physical Review Letters 85:3057-3060.
Henrickson, et al. "Probing single nanometer-scale pores with polymeric molecular rulers." J. Chem. Phys. Apr. 7, 2010;132 (13) :135101. Doi:10.1063/1.3328875.
Holden, et al. Direct introduction of single protein channels and pores into lipid bilayers. J Am Chem Soc. May 11, 2005; 127 (18) :6502-3.
Holden, et al. Direct transfer of membrane proteins from bacteria to planar bilayers for rapid screening by single- channel recording. Nat Chem Biol. Jun. 2006; 2 (6) :314-8. Epub May 7, 2008.
Hromada, et al. Single molecule measurements within individual membrane-bound ion channels using a polymer-based bilayer lipid membrane chip. Lab Chip. Apr. 2008; 8 (4) :602-8. Epub Feb. 29, 2008.
Ito, et al. Simultaneous determination of the size and surface charge of individual nanoparticles using a carbon nanotube-based Coulter counter. Anal Chem. May 15, 2003;75 (10) :2399-406.
Ju, J., Glazer, A.N., and Mathies, R.A. (1996) "Energy Transfer Primers: A new Fluorescence Labeling Paradigm for DNA Sequencing and Analysis," Nature Medicine 2:246-249.
Ju, J., Ruan C., Fuller, C.W., Glazer, A.N., and Mathies, R.A. (1995) "Fluorescence energy transfer dye-labeled primers for DNA sequencing and analysis," Proc. Natl. Acad. Sci. USA 92: 4347-4352.
Ju, J. et al. (1996) "Cassette Labeling for Facile Construction of Energy Transfer Fluorescent Primers," Nuc. Acids Res. 24 (6) :1144-1149.
Ju et al., "Four-color DNA Sequencing by Synthesis using Cleavable Fluorescent Nucleotide Reversible Terminators", PNAS, 103 (52) :19635-19640 (2006).
Jurak, et al. "wettability and topography of phospholipid DPPC multilayers deposited by spin-coating on glass, silicon, and mica slides." Langmuir. Sep. 25, 2007;23 (20) :10156-63. Epub Dec. 14, 2006.
Kang et al. A storable encapsulated bilayer chip containing a single protein nanopore. J Am Chem Soc. Apr. 18, 2007; 129 (15) :4701-5. Epub Mar. 22, 2007.
Kasianowicz J.J., Brandin, B., Branton, D. and Deamer, D.W. (1996) "Characterization of Individual Polynucleotide Molecules Using a Membrane Channel," Proc. Natl. Acad. Sci. USA 93:13770-13773.
Kasianowicz. Nanometer-scale pores: potential applications for analyte detection and DNA characterization. Dis. Markers. 2002;18 (4) 185-91.
Kasianowicz, J.J. (2003) "Nanonmeter-scale pores: potential applications for DNA characterization and analyte detection." Disease Markers 18:185-191.
Kasianowicz J.J. (2004) "Nanopore. Flossing with DNA" Nature Materials 3:355-356.
Kawano et al. Controlling the translocation of single-stranded DNA through alpha-hemolysin ion channels using viscosity. Langmuir. Jan. 20, 2009; 25 (2) :1233-7.
Krasilnikov, et al. "A simple method for the determination of the pore radius of ion channels in planar lipid bilayer membranes." FEMS Microbiol Immunol. Sep. 1992;5 (1-3) :93-100.
Krasilnikov, et al. "Single polymer molecules in a protein nanopore in the limit of a strong polymer-pore attraction." Phys Rev Lett. Jul. 7, 2006;97 (1) :018301. Epub Jul. 5, 2006.
Krasilnikov, et al. "Sizing channels with neutral polymers." In NATO Advanced Research Workshop: Structure and dynamics of confined polymers. Kluwer Press. 2002;97-116.
Kullman, et al. Transport of maltodextrins through maltoporin: a single-channel study. Biophys J. Feb. 2002; 82 (2) :803-12.
Kumar et al. (2005) "Terminal phosphate labeled nucleotides: Synthesis, applications, and linker effect on incorporation by DNA polymerases", Nucleosides, Nucleotides, and Nucleic Acids, 24 (5-7) :401-108.
Kumar et al. PEG-labeled nucleotides and nanopore detection for single molecule DNA sequencing by synthesis. Sci Rep. 2012; 2:684. Epub Sep. 21, 2012.
Kutik et al. Dissecting membrane insertion of mitochondrial beta-barrel proteins. Cell. Mar. 21, 2008; 132 (6) :1011-24.
Lee, S.E. et al. (2001) "Enhancing the catalytic repertoire of nucleic acids: a systematic study of linker length and rigidity." Nucleic Acids Research 29 (7) :1565-1573.
Search Report in corresponding Chinese pat. appl. No. CN201380058224.1; dated Jul. 1, 2016.
Supplementary Search Report in corresponding EP 13853114; dated May 1, 2016.
Supplementary European Search Report dated May 12, 2016 for European Application No. 13853114.0.
Allowed claims dated Apr. 30, 2008 in U.S. Appl. No. 12/084,457.
Chinese office action dated Apr. 9, 2013 for CN Application No. 200780028545.1. (with English translation).
European search report and opinion dated Apr. 16, 2014 for EP Application No. 11848220.7.
International search report and written opinion dated Oct. 25, 2013 for PCT Application No. US2013/035635.
Invitation to Pay Additional Fees dated Aug. 19, 2013 for PCT Application No. US2013/035635.
Office Action dated Mar. 27, 2014 in connection with Chinese Patent Application No. 201180063978.7 (with English translation of cover page only).
Pending claims dated Jul. 19, 2011 in U.S. Appl. No. 13/186,353.
Pending claims dated Dec. 14, 2007 in U.S. Appl. No. 11/922,385.
Pending claims in U.S. Appl. No. 13/959,660, filed Aug. 5, 2013, Ju et al.
International search report dated Feb. 7, 2014 for PCT Application No. US2013/068967.
International search report dated Sep. 24, 2013 for PCT Application No. US2013/035630.
Office action dated Mar. 28, 2014 for U.S. Appl. No. 13/333,932.
Office action dated Apr. 10, 2014 for U.S. Appl. No. 12/658,602.

(56) References Cited

OTHER PUBLICATIONS

Office action dated Apr. 10, 2014 for U.S. Appl. No. 13/759,701.
Office action dated Apr. 11, 2014 for U.S. Appl. No. 12/658,601.
Office action dated Apr. 15, 2014 for U.S. Appl. No. 12/658,591.
Chinese office action dated Jul. 2, 2012 for CN, Application No. 200780028545.1.
Chinese office action dated Oct. 12, 2013 for CN. Application No. 200780028545.1.
International Preliminary Report on Patentability dated Dec. 24, 2008 in connection with International Application No. PCT/US2007/013559.
International search report and written opinion dated Mar. 18, 2013 for PCT/US2012/063099.
International search report and written opinion dated May 3, 2012 for PCT/US2012/020827.
International search report and written opinion dated May 9, 2013 for PCT/US2013/028058.
International search report and written opinion dated May 16, 2013 for PCT Application No. US2013/026514.
International search report and written opinion dated May 16, 2013 for PCT Application No. US2013/022273.
International search report and written opinion dated Jul. 8, 2011 for PCT/US2011/064490.
International search report and written opinion dated Aug. 28, 2012 for PCT/US2011/066627.
International search report and written opinion dated Aug. 28, 2012 for PCT/US2011/066632.
International search report and written opinion dated Sep. 13, 2013 for PCT Application No. US2013/046012.
International search report and written opinion dated Oct. 29, 2007 for PCT/US2007/013559.
International search report and written opinion dated Nov. 5, 2012 for PCT/US2011/064490.
International search report dated Feb. 24, 2012 for PCT/US2011/065640.
International search report dated Feb. 26, 2013 for PCT Application No. US2012/069911.
Office action dated Jan. 17, 2014 for U.S. Appl. No. 13/276,200.
Office action dated Feb. 25, 2013 for U.S. Appl. No. 13/396,522.
Office action dated Apr. 11, 2013 for U.S. Appl. No. 12/658,603.
Office action dated Apr. 26, 2012 for U.S. Appl. No. 12/658,591.
Office action dated Apr. 26, 2012 for U.S. Appl. No. 12/658,601.
Office action dated Jun. 15, 2012 for U.S. Appl. No. 12/658,604.
Office action dated Jun. 28, 2012 for U.S. Appl. No. 12/308,091.
Office action dated Aug. 3, 2012 for U.S. Appl. No. 12/658,602.
Office action dated Oct. 2, 2012 for U.S. Appl. No. 12/658,603.
Office action dated Oct. 16, 2012 for U.S. Appl. No. 12/658,601.
Office action dated Oct. 25, 2012 for U.S. Appl. No. 12/658,591.
Office action dated Nov. 26, 2011 for U.S. Appl. No. 12/308,091.
Office action dated Dec. 17, 2012 for U.S. Appl. No. 13/620,973.
Oxford Nanopore Technologies, Sensor Array Chip, Jul. 14, 2011.
Fuller et al., "Real-time single-molecule electronic DNA sequencing by synthesis using polymer-tagged nucleotides on a nanopore array", PNAS, vol. 113, No. 19, pp. 5233-5238, published May 10, 2016; doi/10.1073.
Walker et al., "Key Residues for Membrane Binding, Oligomerization, and Pore Forming Activity of Staphylococcal alpha-hemolysin Identified by Cysteine Scanning Mutagenesis and Targeted Chemical Modification", J. Biol. Chem. 1995, doe: 10.1074/jbc.270.39.23065.

\* cited by examiner

SEQUENCE LISTING

```
<160> NUMBER OF SEQ ID NOS: 39

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aggtctaggt ctaggtctag gtctaggtct aggtctaggt ct                          42

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatcgggagg aggtgggagc ggag                                              24

<210> SEQ ID NO 3
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatcctccgc tcccacctcc tccc                                          24

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatcgggagg aggtgggagc ggaggaggtg ggagcggag                          39

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatcctccgc tcccacctcc tccgctccca cctcctccc                          39

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggaggaggtg ggagcggagg aggtgggagc ggaggaggtg ggagcggag               49

<210> SEQ ID NO 7
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatcctccgc tcccacctcc tccgctccca cctcctccgc tcccacctcc tccc         54

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggaggaggtg ggagcggagg aggtgggagc ggaggaggtg ggagcggagg aggtgggagc   60
ggag                                                                64

<210> SEQ ID NO 9
```

```
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tccgctccca cctcctccgc tcccacctcc tccgctccca cctcctccgc tcccacctcc      60
tccc                                                                   64

<210> SEQ ID NO 10
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatcgggagg aggtgggagc ggaggaggtg ggagcggagg aggtgggagc ggaggaggtg      60
ggagcggagg aggtgggagc ggag                                             84

<210> SEQ ID NO 11
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gatcctccgc tcccacctcc tccgctccca cctcctccgc tcccacctcc tccgctccca      60
cctcctccgc tcccacctcc tccc                                             84

<210> SEQ ID NO 12
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gatcgggagg aggtgggagc ggaggaggtg ggagcggagg aggtgggagc ggaggaggtg      60
ggagcggagg aggtgggagc ggaggaggag gtgggagcgg ag                        102

<210> SEQ ID NO 13
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gatcctccgc tcccacctcc tcctccgctc ccacctcctc cgctcccacc tcctccgctc      60
ccacctcctc cgctcccacc tcctccgctc ccacctcctc cc                        102

<210> SEQ ID NO 14
<211> LENGTH: 42
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 14
gatcgggaga agcggcagcg aaagaagcgg cagcgaaagg ag                          42

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gatcctcctt tcgctgccgc ttctttcgct gccgcttctc cc                          42

<210> SEQ ID NO 16
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gatcgggaga agcggcagcg aaagaagcgg cagcgaaaga agcggcagcg aaagaagcgg       60
cagcgaaagg ag                                                           72

<210> SEQ ID NO 17
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gatcctcctt tcgctgccgc ttctttcgct gccgcttctt tcgctgccgc ttctttcgct       60
gccgcttctc cc                                                           72

<210> SEQ ID NO 18
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gatcgggaga agcggcagcg aaagaagcgg cagcgaaagg aggagaagcg gcagcgaaag       60
aagcggcagc gaaaggag                                                     78

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gatcctcctt tcgctgccgc ttctttcgct gccgcttctc ctcctttcgc tgccgcttct       60
ttcgctgccg cttctccc                                                     78
```

<210> SEQ ID NO 20
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gatcgggaga agcggcagcg aaagaagcgg cagcgaaaga agcggcagcg aaagaagcgg      60
cagcgaaaga agcggcagcg aaagaagcgg cagcgaaagg ag                       102

<210> SEQ ID NO 21
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gatcctcctt tcgctgccgc ttctttcgct gccgcttctt tcgctgccgc ttctttcgct      60
gccgcttctt tcgctgccgc ttctttcgct gccgcttctc cc                       102

<210> SEQ ID NO 22
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gatcgggaga agcggcagcg aaagaagcgg cagcgaaagg aggagaagcg gcagcgaaag      60
aagcggcagc gaaaggagga gaagcggcag cgaaagaagc ggcagcgaaa ggag          114

<210> SEQ ID NO 23
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gatcctcctt tcgctgccgc ttctttcgct gccgcttctc ctcctttcgc tgccgcttct      60
ttcgctgccg cttctcctcc tttcgctgcc gcttctttcg ctgccgcttc tccc          114

<210> SEQ ID NO 24
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gatcgggaga agcggcagcg aaagaagcgg cagcgaaaga agcggcagcg aaagaagcgg      60
cagcgaaaga agcggcagcg aaagaagcgg cagcgaaaga agcggcagcg aaagaagcgg    120
cagcgaaagg ag                                                        132

```
<210> SEQ ID NO 25
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gatcctcctt tcgctgccgc ttctttcgct gccgcttctt tcgctgccgc ttctttcgct        60
gccgcttctt tcgctgccgc ttctttcgct gccgcttctt tcgctgccgc ttctttcgct       120
gccgcttctc cc                                                           132

<210> SEQ ID NO 26
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gatcgggaga agcggcagcg aaagaagcgg cagcgaaaga agcggcagcg aaagaagcgg        60
cagcgaaagg aggagaagcg gcagcgaaag aagcggcagc gaaagaagcg gcagcgaaag       120
aagcggcagc gaaaggag                                                     138

<210> SEQ ID NO 27
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gatcctcctt tcgctgccgc ttctttcgct gccgcttctt tcgctgccgc ttctttcgct        60
gccgcttctc ctcctttcgc tgccgcttct ttcgctgccg cttctttcgc tgccgcttct       120
ttcgctgccg cttctccc                                                     138

<210> SEQ ID NO 28
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gatcgggaga agcggcagcg aaagaagcgg cagcgaaaga agcggcagcg aaagaagcgg        60
cagcgaaaga agcggcagcg aaagaagcgg cagcgaaaga agcggcagcg aaagaagcgg       120
cagcgaaaga agcggcagcg aaagaagcgg cagcgaaagg ag                          162

<210> SEQ ID NO 29
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gatcctcctt tcgctgccgc ttctttcgct gccgcttctt tcgctgccgc ttctttcgct        60
```

```
gccgcttctt tcgctgccgc ttctttcgct gccgcttctt tcgctgccgc ttctttcgct    120
gccgcttctt tcgctgccgc ttctttcgct gccgcttctc cc                       162

<210> SEQ ID NO 30
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gatcgggaga agcggcagcg aaagaagcgg cagcgaaagg aggagaagcg gcagcgaaag    60
aagcggcagc gaaagaagcg gcagcgaaag aagcggcagc gaaagaagcg gcagcgaaag   120
aagcggcagc gaaaggagga gaagcggcag cgaaagaagc ggcagcgaaa ggag          174

<210> SEQ ID NO 31
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gatcctcctt tcgctgccgc ttctttcgct gccgcttctc ctcctttcgc tgccgcttct    60
ttcgctgccg cttctttcgc tgccgcttct ttcgctgccg cttctttcgc tgccgcttct   120
ttcgctgccg cttctcctcc tttcgctgcc gcttctttcg ctgccgcttc tccc          174

<210> SEQ ID NO 32
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gatcgggaga agcggcagcg aaagaagcgg cagcgaaaga agcggcagcg aaagaagcgg    60
cagcgaaaga agcggcagcg aaagaagcgg cagcgaaaga agcggcagcg aaagaagcgg   120
cagcgaaaga agcggcagcg aaagaagcgg cagcgaaaga agcggcagcg aaagaagcgg   180
cagcgaaagg ag                                                       192

<210> SEQ ID NO 33
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gatcctcctt tcgctgccgc ttctttcgct gccgcttctt tcgctgccgc ttctttcgct    60
gccgcttctt tcgctgccgc ttctttcgct gccgcttctt tcgctgccgc ttctttcgct   120
gccgcttctt tcgctgccgc ttctttcgct gccgcttctt tcgctgccgc ttctttcgct   180
gccgcttctc cc                                                       192

<210> SEQ ID NO 34
```

<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gatcgggaga agcggcagcg aaagaagcgg cagcgaaaga agcggcagcg aaagaagcgg    60
cagcgaaagg agaagcggca gcgaaagaag cggcagcgaa agaagcggca gcgaaagaag   120
cggcagcgaa aggagaagcg gcagcgaaag aagcggcagc gaaagaagcg gcagcgaaag   180
aagcggcagc gaaaggag                                                198

<210> SEQ ID NO 35
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gatcctcctt tcgctgccgc ttctttcgct gccgcttctt tcgctgccgc ttctttcgct    60
gccgcttctc ctttcgctgc cgcttctttc gctgccgctt ctttcgctgc cgcttctttc   120
gctgccgctt ctcctttcgc tgccgcttct ttcgctgccg cttctttcgc tgccgcttct   180
ttcgctgccg cttctccc                                                198

<210> SEQ ID NO 36
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36 agtcagtc                                                             8

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Gly Gly Ser
1               5

<210> SEQ ID NO 39

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Ala Ala Ala Lys
1               5
```

NUCLEIC ACID SEQUENCES USING TAGS

CROSS-REFERENCE

This application is a divisional of U.S. application Ser. No. 14/073,445, filed Nov. 6, 2013, now allowed, which claims the benefit of U.S. Provisional Application No. 61/880,407, filed Sep. 20, 2013, U.S. Provisional Application No. 61/737,621, filed Dec. 14, 2012, and U.S. Provisional Application No. 61/724,869, filed Nov. 9, 2012, each of which is incorporated herein by reference in its entirety.

This invention was made with government support under grant HG007415 awarded by the NIH. The government has certain rights in the invention.

REFERENCE TO SEQUENCE LISTING

This application incorporates-by-reference nucleotide and/or amino acid sequences which are present in the file named "170303_89295-Z_Sequence_Listing_RBR", which is 13 kilobytes in size, and which was created Mar. 3, 2017 in the IBM-PC machine format, having an operating system compatibility with MS-Windows, which is contained in the ASCII format file that was filed Mar. 3, 2017 as part of this application.

BACKGROUND

Nucleic acid sequencing is a process that may be used to provide sequence information for a nucleic acid sample. Such sequence information may be helpful in diagnosing and/or treating a subject. For example, the nucleic acid sequence of a subject may be used to identify, diagnose and potentially develop treatments for genetic diseases. As another example, research into pathogens may lead to treatment for contagious diseases.

There are methods available which may be used to sequence a nucleic acid. Such methods, however, are expensive and may not provide sequence information within a time period and at an accuracy that may be necessary to diagnose and/or treat a subject.

SUMMARY

Methods of nucleic acid sequencing that pass a single stranded nucleic acid molecule through a nanopore may have a sensitivity that may be insufficient or otherwise inadequate for providing date for diagnostic and/or treatment purposes. Nucleic acid bases comprising the nucleic acid molecule (e.g., adenine (A), cytosine (C), guanine (G), thymine (T) and/or uracil (U)) may not provide a sufficiently distinct signal from each other. In particular, the purines (i.e., A and G) are of a similar size, shape and charge to each other and provide an insufficiently distinct signal in some instances. Also, the pyrimidines (i.e., C, T and U) are of a similar size, shape and charge to each other and provide an insufficiently distinct signal in some instances. Recognized herein is the need for improved methods for nucleic acid molecule identification and nucleic acid sequencing.

In some embodiments, nucleotide incorporation events (e.g., incorporation of a nucleotide into a nucleic acid strand that is complementary to a template strand) present tags to a nanopore and/or release tags from the nucleotides which are detected by a nanopore. The incorporated base may be identified (i.e., A, C, G, T or U) because a unique tag is released and/or presented for each type of nucleotide (i.e., A, C, G, T or U).

In some embodiments, a tag is attributed to a successfully incorporated nucleotide based on the time period in which the tag is detected to interact with a nanopore. The time period can be longer than the time period associated with the free flow of the nucleotide tag through the nanopore. The detection time period of a successfully incorporated nucleotide tag can also be longer than the time period of a non-incorporated nucleotide (e.g., a nucleotide mismatched to the template strand).

In some instances, a polymerase is associated with the nanopore (e.g., covalently linked to the nanopore) and the polymerase performs nucleotide incorporation events. The tag can be detected by the nanopore when the tagged nucleotide is associated with the polymerase. In some cases, tagged nucleotides that are not incorporated pass through the nanopore. The method can distinguish between tags associated with un-incorporated nucleotides and tags associated with incorporated nucleotides based on the length of time the tagged nucleotide is detected by the nanopore. In one embodiment, an un-incorporated nucleotide is detected by the nanopore for less than about 1 millisecond and an incorporated nucleotide is detected by the nanopore for at least about 1 millisecond.

In some embodiments, the polymerase has a slow kinetic step where the tag is detectable by the nanopore for at least 1 millisecond with an average detection time of about 100 ms. The polymerase can be a mutated phi29 DNA polymerase.

The polymerase can be mutated to reduce the rate at which the polymerase incorporates a nucleotide into a nucleic acid strand (e.g., a growing nucleic acid strand). In some case, the rate at which a nucleotide is incorporated into a nucleic acid strand can be reduced by functionalizing the nucleotide and/or template strand to provide steric hindrance, such as, for example, through methylation of the template nucleic acid strand. In some instances, the rate is reduced by incorporating methylated nucleotides.

In an aspect, a method for sequencing a nucleic acid sample with the aid of a nanopore in a membrane adjacent to a sensing electrode comprises: (a) providing tagged nucleotides into a reaction chamber comprising the nanopore, wherein an individual tagged nucleotide of the tagged nucleotides contains a tag coupled to a nucleotide, which tag is detectable with the aid of the nanopore; (b) carrying out a polymerization reaction, with the aid of a polymerase, thereby incorporating an individual tagged nucleotide of the tagged nucleotides into a growing strand complementary to a single stranded nucleic acid molecule from the nucleic acid sample; and (c) detecting, with the aid of the nanopore, a tag associated with the individual tagged nucleotide during and/or upon incorporation of the individual tagged nucleotide, wherein the tag is detected with the aid of the nanopore when the nucleotide is associated with the polymerase.

In some embodiments, the tag is detected a plurality of times while associated with the polymerase.

In some embodiments, an electrode is re-charged between tag detection periods.

In some embodiments, the method distinguishes between an incorporated tagged nucleotide and a non-incorporated tag nucleotide based on the length of time the tagged nucleotide is detected by the nanopore.

In some embodiments, the ratio of the time an incorporated tagged nucleotide is detected by the nanopore to the time a non-incorporated tagged nucleotide is detected by the nanopore is at least about 1.5, 2, 3, 4, 5, 6, 7, 8, 9, 10, 20, 30, 40, 50, 100, 1000, or 10,000.

In some embodiments, the ratio of the time period in which a tag associated with an incorporated nucleotide interacts with (and is detected with the aid of) a nanopore to the time period in which a tag associated with an unincorporated nucleotide interacts with the nanopore at least about 1.5, 2, 3, 4, 5, 6, 7, 8, 9, 10, 20, 30, 40, 50, 100, 1000, or 10,000.

In some embodiments, the nucleotide is associated with the polymerase for an average (or mean) time period at least about 1 millisecond.

In some embodiments, the tagged nucleotide passes through the nanopore in less than 1 milliseconds (ms) when the nucleotide is not associated with the polymerase.

In some embodiments, the tag has a length that is selected to be detectable by the nanopore.

In some embodiments, the incorporation of a first tagged nucleotide does not interfere with nanopore detection of a tag associated with a second tagged nucleotide.

In some embodiments, nanopore detection of a tag associated with a first tagged nucleotide does not interfere with the incorporation of a second tagged nucleotide.

In some embodiments, nanopore is capable of distinguishing between an incorporated tagged nucleotide and a non-incorporated tag nucleotide with an accuracy of at least 95%.

In some embodiments, nanopore is capable of distinguishing between an incorporated tagged nucleotide and a non-incorporated tag nucleotide with an accuracy of at least 99%.

In some embodiments, the tag associated with the individual tagged nucleotide is detected when the tag is released from the individual tagged nucleotide.

In an aspect, a method for sequencing a nucleic acid sample with the aid of a nanopore in a membrane adjacent to a sensing electrode comprises: (a) providing tagged nucleotides into a reaction chamber comprising the nanopore, wherein an individual tagged nucleotide of the tagged nucleotides contains a tag coupled to a nucleotide, which tag is detectable with the aid of the nanopore; (b) incorporating, with the aid of an enzyme, an individual tagged nucleotide of the tagged nucleotides into a growing strand complementary to a single stranded nucleic acid molecule derived from the nucleic acid sample; and (c) during incorporation of the individual tagged nucleotide, differentiating, with the aid of the nanopore, a tag associated with the individual tagged nucleotide from one or more tags associated with one or more unincorporated individual tagged nucleotides.

In some embodiments, the enzyme is a nucleic acid polymerase or any enzyme which may extend a newly synthesized strand based upon a template polymer.

In some embodiments, the individual tagged nucleotide incorporated in (b) is differentiated from unincorporated individual tagged nucleotides based on the lengths of time and/or ratios of time that the individual tagged nucleotide incorporated in (b) and the unincorporated individual tagged nucleotides are detected with the aid of the nanopore.

In an aspect, a method for sequencing a nucleic acid with the aid of a nanopore in a membrane comprises: (a) providing tagged nucleotides into a reaction chamber comprising the nanopore, wherein an individual tagged nucleotide of the tagged nucleotides contains a tag that is detectable by the nanopore; (b) incorporating the tagged nucleotides into a growing nucleic acid chain, wherein the a tag associated with an individual tagged nucleotide of the tagged nucleotides resides in or in proximity to at least a portion of the nanopore during incorporation, wherein the ratio of the time an incorporated tagged nucleotide is detectable by the nanopore to the time a non-incorporated tag is detectable by the nanopore is at least 1.1, 1.2, 1.3, 1.4, 1.5, 2, 3, 4, 5, 6, 7, 8, 9, 10, 20, 30, 40, 50, 60, 70, 80, 90, 100, 1000, 10,000; and (c) detecting the tag with the aid of the nanopore.

In some embodiments, the ratio of the time an incorporated tagged nucleotide is detectable by the nanopore to the time a non-incorporated tag is detectable by the nanopore is at least about 1.1, 1.2, 1.3, 1.4, 1.5, 2, 3, 4, 5, 6, 7, 8, 9, 10, 20, 30, 40, 50, 60, 70, 80, 90, 100, 1000, or 10,000.

In some embodiments, the tag remains associated with an individual nucleotide upon incorporation of the nucleotide.

In some embodiments, the tag associated with an individual nucleotide is released upon incorporation of the nucleotide.

In some embodiments, the method further comprises expelling the tag from the nanopore.

In some embodiments, the tag is expelled in the reverse direction from which the tag entered the nanopore.

In some embodiments, the tag resides in the nanopore for at least about 100 ms.

In some embodiments, the tag resides in the nanopore for at least about 10 ms.

In some embodiments, the tag resides in the nanopore for at least about 1 ms.

In some embodiments, the tagged nucleotides are incorporated at a rate of at most about 1 nucleotide per second.

In some embodiments, the nanopore expels the tag molecule with a voltage pulse.

In some embodiments, the tag molecule is at least 99% likely to be expelled with the voltage pulse.

In some embodiments, the nanopore expels the tag molecule within a period of time such that two tag molecules are not present in the nanopore at the same time.

In some embodiments, the nanopore expels the tag molecule within a period of time such that the probability of two tag molecules being present in the nanopore at the same time is at most 1%.

In some embodiments, the tag has a diameter less than about 1.4 nm.

In some embodiments, each tag associated with an incorporated tagged nucleotide is detected with the aid of the nanopore while the tag is attached to the nucleotide.

In some embodiments, the tag associated with the individual tagged nucleotide is detected when the tag is released from the individual tagged nucleotide.

In an aspect, a chip for sequencing a nucleic acid sample comprises: a plurality of nanopores, a nanopore of the plurality having at least one nanopore in a membrane disposed adjacent or in proximity to an electrode, wherein each nanopore detects a tag associated with an individual tagged nucleotide during incorporation of the tagged nucleotide into a growing nucleic acid chain. In some embodiments, the nanopores are individually addressable.

In some embodiments, the individual nanopore detects the tag associated with the nucleotide during subsequent passage of the tag through or adjacent to the nanopore.

In some embodiments, the chip comprises at least 500 individually addressable electrodes per square millimeter. In some embodiments the chip comprises at least 50 individually addressable electrodes per square millimeter.

In some embodiments, the chip distinguishes between an incorporated tagged nucleotide and a non-incorporated tag nucleotide based at least in part on the length of time that the tagged nucleotide is detected by the nanopore.

In some embodiments, the ratio of the time an incorporated tagged nucleotide is detectable by the nanopore to the time a non-incorporated tag is detectable by the nanopore is at least about 1.5.

In some embodiments, the incorporation of a first tagged nucleotide does not interfere with nanopore detection of a tag associated with a second tagged nucleotide.

In some embodiments, nanopore detection of a tag associated with a first tagged nucleotide does not interfere with the incorporation of a second tagged nucleotide.

In some embodiments, the nanopore is capable of distinguishing between an incorporated tagged nucleotide and a non-incorporated tag nucleotide with an accuracy of at least 95%.

In some embodiments, the nanopore is capable of distinguishing between an incorporated tagged nucleotide and a non-incorporated tag nucleotide with an accuracy of at least 99%.

In some embodiments, the electrode is part of an integrated circuit.

In some embodiments, the electrode is coupled to an integrated circuit.

In some embodiments, each tag associated with an incorporated tagged nucleotide is detected with the aid of the nanopore while the tag is attached to the nucleotide.

In some embodiments, the tag associated with the individual tagged nucleotide is detected when the tag is released from the individual tagged nucleotide.

In an aspect, a chip for sequencing a nucleic acid sample comprises: a plurality of nanopores, wherein a nanopore of the plurality contains at least one nanopore in a membrane disposed adjacent to an electrode, wherein each nanopore is capable of detecting a tag species upon or during incorporation of a nucleic acid molecule comprising the tag species into a growing nucleic acid chain, wherein, the ratio of the time an incorporated tagged nucleotide is detectable by the nanopore to the time a non-incorporated tag is detectable by the nanopore is at least about 1.5. In some embodiments, the plurality of nanopores are individually addressable.

In some embodiments, the tag species does not pass through the nanopore upon incorporation.

In some embodiments, the chip is configured to expel the tag species from the nanopore.

In some embodiments, the nanopore expels the tag species with a voltage pulse.

In some embodiments, the electrode is part of an integrated circuit.

In some embodiments, the electrode is coupled to an integrated circuit.

In some embodiments, each tag associated with an incorporated tagged nucleotide is detected with the aid of the nanopore while the tag is attached to the nucleotide.

In some embodiments, the tag species of the nucleic acid molecule is detected without the tag species being released from the nucleic acid molecule.

In an aspect, a system for sequencing a nucleic acid sample comprises: (a) a chip comprising one or more nanopore devices, each of the one or more nanopore devices comprising a nanopore in a membrane that is adjacent to an electrode, wherein the nanopore device detects a tag associated with an individual tagged nucleotide during incorporation of the tagged nucleotide by a polymerase; and (b) a processor coupled to the chip, wherein the processor is programmed to aid in characterizing a nucleic acid sequence of the nucleic acid sample based on electrical signals received from the nanopore device.

In some embodiments, the nanopore device detects a tag associated with an individual tagged nucleotide during subsequent progression of the tag through or adjacent to the nanopore.

In some embodiments, the nanopore device comprises individually addressable nanopores.

In some embodiments, the chip comprises at least 500 individually addressable electrodes per square millimeter. In some embodiments, the chip comprises at least 50 individually addressable electrodes per square millimeter In some embodiments, the chip distinguishes between an incorporated tagged nucleotide and a non-incorporated tag nucleotide based at least in part on the length of time that the tagged nucleotide is detected by the nanopore.

In some embodiments, the ratio of the time an incorporated tagged nucleotide is detectable by the nanopore to the time a non-incorporated tag is detectable by the nanopore is at least about 1.5.

In some embodiments, the incorporation of a first tagged nucleotide does not interfere with nanopore detection of a tag associated with a second tagged nucleotide.

In some embodiments, nanopore detection of a tag associated with a first tagged nucleotide does not interfere with the incorporation of a second tagged nucleotide.

In some embodiments, the nanopore is capable of distinguishing between an incorporated tagged nucleotide and a non-incorporated tag nucleotide with an accuracy of at least 95%.

In some embodiments, the nanopore is capable of distinguishing between an incorporated tagged nucleotide and a non-incorporated tag nucleotide with an accuracy of at least 99%.

In some embodiments, the electrode is part of an integrated circuit.

In some embodiments, the electrode is coupled to an integrated circuit.

In some embodiments, each tag associated with an incorporated tagged nucleotide is detected with the aid of the nanopore while the tag is attached to the nucleotide.

In some embodiments, the tag associated with the individual tagged nucleotide is detected when the tag is released from the individual tagged nucleotide.

In some embodiments, a tag is directed into and through at least a portion of the nanopore using a given driving force, such as an electrical potential applied to the nanopore or membrane containing the nanopore (V+). The tag can be directed into the nanopore from an opening of the nanopore. The driving force can then be reversed (e.g., electrical potential of opposite polarity applied, or V−) to expel at least a portion of the tag from the nanopore through the opening. The driving force can then be applied again (e.g., V+) to drive at least a portion of the tag into the nanopore through the opening. Alternatively, a polarity of the tag can be reversed and a sequence of potentials including V−, V+, and V− may be used. This can increase the time period in which the tag can be detected with the aid of the nanopore.

In some embodiments, a nanopore and/or tag are configured to provide an energy landscape such that, in the nanopore, the tag associated with a nucleotide is more likely to move in one direction (e.g., into the pore) than another direction (e.g., out of the pore).

In some embodiments the detection of modified bases (e.g., methylated) in a template sample strand can be detected by the difference in the time that a tag of a tagged nucleotide is detected by a nanopore while associated with a polymerase during and/or upon the nucleotide portion of the nucleotide tag's incorporation into a newly synthesized strand. In some cases, the time of a nucleotide tag being associated with an enzyme is longer when the opposing nucleotide of the sample sequence is a methylated nucleotide as compared to a non-methylated nucleotide.

Examples of tagged nucleotides described herein can be any naturally occurring nucleotides modified with cleavable tags or synthetic, non-natural nucleotide analogs modified with cleavable tags. For example, universal bases modified with cleavable or uncleavable tags may be used to simply count the number of bases in a sample strand.

Examples of tagged nucleotides described herein can be dimer nucleotides or dimer nucleotide analogs that can be extended as dimer units and the tags report the combined dimer composition of the dimer nucleotide based upon time in association with the polymerase enzyme and the signal level detected by a nanopore device.

While the time a tag is associated with an enzyme can be used to differentiate between incorporated nucleotides and non-incorporated nucleotides, the unique current levels and/or electrical response of a tag in a nanopore to an applied potential or a varying applied potential, allows differentiation between tags associated with different nucleotides.

In an aspect, a method for sequencing a nucleic acid comprises applying an alternating current (AC) waveform to a circuit in proximity to a nanopore and sensing electrode, wherein a tag associated with a nucleotide being incorporated into a growing nucleic acid strand complimentary to a template nucleic acid strand is detected when the waveform has a first polarity and the electrode is re-charged when the waveform has a second polarity.

In another aspect, a method for sequencing a nucleic acid molecule comprises: (a) providing one or more tagged nucleotides to a nanopore in a membrane adjacent to an electrode; (b) incorporating an individual tagged nucleotide of said one or more tagged nucleotides into a strand complementary to said nucleic acid molecule; and (c) detecting a tag associated with said tagged nucleotide one or more times with the aid of an alternating current (AC) waveform applied to said electrode, wherein said tag is detected while said tag is attached to said individual tagged nucleotide incorporated into said strand.

In some embodiments, the waveform is such that the electrode is not depleted over a time period of at least about 1 second, 10 seconds, 30 seconds, 1 minute, 10 minutes, 20 minutes, 30 minutes, 1 hour, 2 hours, 3 hours, 4 hours, 5 hours, 6 hours, 12 hours, 24 hours, 1 day, 2 days, 3 days, 4 days, 5 days, 6 days, 1 week, 2 weeks, 3 weeks, or 1 month.

In some embodiments, the identity of the tag is determined by the relationship between the measured current and the voltage applied by the waveform at various voltages.

In some embodiments, the nucleotides comprise adenine (A), cytosine (C), thymine (T), guanine (G), uracil (U), or any derivatives thereof.

In some embodiments, methylation of a base of the template nucleic acid strand is determined by the tag being detected for a longer period of time when the base is methylated than when the base is not methylated.

In an aspect, a method for determining the length of a nucleic acid or segment thereof with the aid of a nanopore in a membrane adjacent to a sensing electrode comprises (a) providing tagged nucleotides into a reaction chamber comprising said nanopore, wherein nucleotides having at least two different bases contain the same tag coupled to a nucleotide, which tag is detectable with the aid of said nanopore; (b) carrying out a polymerization reaction with the aid of a polymerase, thereby incorporating an individual tagged nucleotide of said tagged nucleotides into a growing strand complementary to a single stranded nucleic acid molecule from said nucleic acid sample; and (c) detecting, with the aid of said nanopore, a tag associated with said individual tagged nucleotide during or subsequent to incorporation of said individual tagged nucleotide.

In an aspect, a method for determining the length of a nucleic acid or segment thereof with the aid of a nanopore in a membrane adjacent to a sensing electrode comprises (a) providing tagged nucleotides into a reaction chamber comprising said nanopore, wherein an individual tagged nucleotide of said tagged nucleotides contains a tag coupled to a nucleotide, which tag is capable of reducing the magnitude of current flowing through said nanopore relative to the current when the tag is not present; (b) carrying out a polymerization reaction with the aid of a polymerase, thereby incorporating an individual tagged nucleotide of said tagged nucleotides into a growing strand complementary to a single stranded nucleic acid molecule from said nucleic acid sample and reducing the magnitude of current flowing through said nanopore; and (c) detecting, with the aid of said nanopore, periods of time between incorporation of said individual tagged nucleotides. In some embodiments, the magnitude of current flowing through said nanopore returns to at least 80% of the maximum current during periods of time between incorporation of said individual tagged nucleotides.

In some embodiments, all nucleotides have the same tag coupled to the nucleotide. In some embodiments, at least some of the nucleotides have tags that identify the nucleotide. In some embodiments, at most 20% of the nucleotides have tags that identify the nucleotide. In some embodiments, all of the nucleotide is identified as being an adenine (A), cytosine (C), guanine (G), thymine (T) and/or uracil (U). In some embodiments, all of the nucleic acid or segment thereof is a Short Tandem Repeat (STR).

In an aspect, a method for assembling a protein having a plurality of subunits comprises (a) providing a plurality of first subunits; (b) providing a plurality of second subunits, wherein the second subunits are modified with respect to the first subunits; (c) contacting the first subunits with the second subunits in a first ratio to form a plurality of proteins having the first subunits and the second subunits, wherein the plurality of proteins have a plurality of ratios of the first subunits to the second subunits; and (d) fractionating the plurality of proteins to enrich proteins that have a second ratio of the first subunits to the second subunits, wherein the second ratio is one second subunit per (n−1) first subunits, wherein 'n' is the number of subunits comprising the protein.

In some embodiments, the protein is a nanopore.

In some embodiments, the nanopore is at least 80% homologous to alpha-hemolysin.

In some embodiments, the first subunits or the second subunits comprise a purification tag.

In some embodiments, the purification tag is a polyhistidine tag.

In some embodiments, the fractionation is performed using ion-exchange chromatography.

In some embodiments, the second ratio is 1 second subunit per 6 first subunits.

In some embodiments, the second ratio is 2 second subunits per 5 first subunits and a single polymerase is attached to each of the second subunits.

In some embodiments, the second subunits comprise a chemically reactive moiety and the method further comprises (e) performing a reaction to attach an entity to the chemically reactive moiety.

In some embodiments, the protein is a nanopore and the entity is a polymerase.

In some embodiments, the first subunits are wild-type.

In some embodiments, the first subunits and/or second subunits are recombinant.

In some embodiments, the first ratio is approximately equal to the second ratio.

In some embodiments, the first ratio is greater than the second ratio.

In some embodiments, the method further comprises inserting the proteins having the second ratio subunits into a bilayer.

In some embodiments, the method further comprises sequencing a nucleic acid molecule with the aid of the proteins having the second ratio subunits.

In another aspect, a nanopore comprises a plurality of subunits, wherein a polymerase is attached to one of the subunits and at least one and less than all of the subunits comprise a first purification tag.

In some embodiments, the nanopore is at least 80% homologous to alpha-hemolysin.

In some embodiments, all of the subunits comprise a first purification tag or a second purification tag.

In some embodiments, the first purification tag is a poly-histidine tag.

In some embodiments, the first purification tag is on the subunit having the polymerase attached.

In some embodiments, the first purification tag is on the subunits not having the polymerase attached.

In another aspect, a method for sequencing a nucleic acid sample with the aid of a nanopore in a membrane adjacent to a sensing electrode comprises: (a) providing tagged nucleotides into a reaction chamber comprising said nanopore, wherein an individual tagged nucleotide of said tagged nucleotides contains a tag coupled to a nucleotide, which tag is detectable with the aid of said nanopore; (b) carrying out a polymerization reaction with the aid of a polymerase, thereby incorporating an individual tagged nucleotide of said tagged nucleotides into a growing strand complementary to a single stranded nucleic acid molecule from said nucleic acid sample; (c) detecting, with the aid of said nanopore, a tag associated with said individual tagged nucleotide during incorporation of said individual tagged nucleotide, wherein said tag is detected with the aid of said nanopore when said nucleotide is associated with said polymerase, and wherein said detecting comprises (i) providing an applied voltage across said nanopore and (ii) measuring a current with said sensing electrode at said applied voltage; and (d) calibrating said applied voltage.

In some embodiments, said calibrating comprises (i) measuring a plurality of escape voltages for said tag molecule, (ii) computing a difference between the measured escape voltages and a reference point, and (iii) shifting the applied voltage by the computed difference.

In some embodiments, a distribution of expected escape voltages versus time are estimated.

In some embodiments, the reference point is the mean or median of the measured escape voltages.

In some embodiments, the method removes detected variations in expected escape voltage distribution.

In some embodiments, the method is performed on a plurality of independently addressable nanopores each adjacent to a sensing electrode.

In some embodiments, the applied voltage decreases over time.

In some embodiments, the presence of the tag in the nanopore reduces the current measured with the sensing electrode at the applied voltage.

In some embodiments, the tagged nucleotides comprise a plurality of different tags and the method detects each of the plurality of different tags.

In some embodiments, (d) increases the accuracy of the method when compared to performing steps (a)-(c).

In some embodiments, (d) compensates for changes in electrochemical conditions over time.

In some embodiments, (d) compensates for different nanopores having different electrochemical conditions in a device having a plurality of nanopores.

In some embodiments, (d) compensates for different electrochemical conditions for each performance of the method.

In some embodiments, the method further comprises (e) calibrating variations in a current gain and/or variations in a current offset.

In some embodiments, said tag is detected a plurality of times while associated with said polymerase.

In some embodiments, an electrode is re-charged between tag detection periods.

In some embodiments, the method distinguishes between an incorporated tagged nucleotide and a non-incorporated tag nucleotide based on the length of time said tagged nucleotide is detected by said nanopore.

In another aspect, a method for sequencing a nucleic acid sample with the aid of a nanopore in a membrane adjacent to a sensing electrode comprises: (a) removing a repetitive nucleic acid sequence from the nucleic acid sample to provide a single-stranded nucleic acid molecule for sequencing; (b) providing tagged nucleotides into a reaction chamber comprising said nanopore, wherein an individual tagged nucleotide of said tagged nucleotides contains a tag coupled to a nucleotide, which tag is detectable with the aid of said nanopore; (c) carrying out a polymerization reaction with the aid of a polymerase, thereby incorporating an individual tagged nucleotide of said tagged nucleotides into a growing strand complementary to the single-stranded nucleic acid molecule; and (d) detecting, with the aid of said nanopore, a tag associated with said individual tagged nucleotide during incorporation of said individual tagged nucleotide, wherein said tag is detected with the aid of said nanopore when said nucleotide is associated with said polymerase.

In some embodiments, the repetitive nucleic acid sequence comprises at least 20 consecutive nucleic acid bases.

In some embodiments, the repetitive nucleic acid sequence comprises at least 200 consecutive nucleic acid bases.

In some embodiments, the repetitive nucleic acid sequence comprises at least 20 consecutive repeated subunits of nucleic acid bases.

In some embodiments, the repetitive nucleic acid sequence comprises at least 200 consecutive repeated subunits of nucleic acid bases.

In some embodiments, the repetitive nucleic acid sequence is removed by hybridization with a nucleic acid sequence complimentary to the repetitive nucleic acid sequence.

In some embodiments, the nucleic acid sequence complimentary to the repetitive nucleic acid sequence is immobilized on a solid support.

In some embodiments, the solid support is a surface.

In some embodiments, the solid support is a bead.

In some embodiments, the nucleic acid sequence complimentary to the repetitive nucleic acid sequence comprises Cot-1 DNA.

In some embodiments, the Cot-1 DNA is enriched in repetitive nucleic acid sequences having a length of between about 50 and about 100 nucleic acid bases.

In another aspect, a method for sequencing a nucleic acid sample with the aid of a nanopore in a membrane adjacent to a sensing electrode comprises: (a) providing tagged nucleotides into a reaction chamber comprising said nanopore, wherein an individual tagged nucleotide of said tagged nucleotides contains a tag coupled to a nucleotide, which tag is detectable with the aid of said nanopore; (b) carrying out a polymerization reaction with the aid of a polymerase attached by a linker to the nanopore, thereby incorporating an individual tagged nucleotide of said tagged nucleotides into a growing strand complementary to a single stranded nucleic acid molecule from said nucleic acid sample; and (c) detecting, with the aid of said nanopore, a tag associated with said individual tagged nucleotide during incorporation of said individual tagged nucleotide, wherein said tag is detected with the aid of said nanopore when said nucleotide is associated with said polymerase.

In some embodiments, the linker is flexible.

In some embodiments, the linker is at least 5 nanometers long.

In some embodiments, the linker is a direct attachment.

In some embodiments, the linker comprises amino acids.

In some embodiments, the nanopore and the polymerase comprise a single polypeptide.

In some embodiments, the linker comprises nucleic acids or polyethylene glycol (PEG).

In some embodiments, the linker comprises a non-covalent bond.

In some embodiments, the linker comprises biotin and streptavidin.

In some embodiments, at least one of: (a) the C-terminus of the polymerase is attached to the N-terminus of the nanopore; (b) the C-terminus of the polymerase is attached to the C-terminus of the nanopore; (c) the N-terminus of the polymerase is attached to the N-terminus of the nanopore; (d) the N-terminus of the polymerase is attached to the C-terminus of the nanopore; and (e) the polymerase is attached to the nanopore where at least one of the polymerase and nanopore are not attached at a terminus.

In some embodiments, the linker orients the polymerase with respect to the nanopore such that the tag is detected with the aid of the nanopore.

In some embodiments, the polymerase is attached to the nanopore by two or more linkers.

In some embodiments, the linker comprises one or more of SEQ ID NOs 2-35, or a PCR product produced therefrom.

In some embodiments, the linker comprises the peptide encoded by one or more of SEQ ID NOs 1-35 or a PCR product produced therefrom.

In some embodiments, the nanopore is at least 80% homologous to alpha-hemolysin.

In some embodiments, the polymerase is at least 80% homologous to phi-29.

In another aspect, a tag molecule comprises (a) a first polymer chain comprising a first segment and a second segment, wherein the second segment is narrower than the first segment; and (b) a second polymer chain comprising two ends, wherein a first end is affixed to the first polymer chain adjacent to the second segment and a second end is not affixed to the first polymer chain, wherein the tag molecule is capable of being threaded through a nanopore in a first direction where the second polymer chain aligns adjacent to the second segment.

In some embodiments, the tag molecule is not capable of being threaded through the nanopore in a second direction where the second polymer chain does not align adjacent to the second segment.

In some embodiments, the second polymer chain base pairs with the first polymer chain when the second polymer chain does not align adjacent to the second segment.

In some embodiments, the first polymer chain is affixed to a nucleotide.

In some embodiments, the first polymer chain is released from the nucleotide when the nucleotide is incorporated into a growing nucleic acid strand.

In some embodiments, the first polymer chain is affixed to a terminal phosphate of the nucleotide.

In some embodiments, the first polymer chain comprises nucleotides.

In some embodiments, the second segment comprises a-basic nucleotides.

In some embodiments, the second segment comprises a carbon chain.

In another aspect, a method for sequencing a nucleic acid sample with the aid of a nanopore in a membrane adjacent to a sensing electrode comprises: (a) providing tagged nucleotides into a reaction chamber comprising said nanopore, wherein an individual tagged nucleotide of said tagged nucleotides contains a tag coupled to a nucleotide, which tag is detectable with the aid of said nanopore, wherein the tag comprises (i) a first polymer chain comprising a first segment and a second segment, wherein the second segment is narrower than the first segment and (ii) a second polymer chain comprising two ends, wherein a first end is affixed to the first polymer chain adjacent to the second segment and a second end is not affixed to the first polymer chain, wherein the tag molecule is capable of being threaded through a nanopore in a first direction where the second polymer chain aligns adjacent to the second segment; (b) carrying out a polymerization reaction with the aid of a polymerase, thereby incorporating an individual tagged nucleotide of said tagged nucleotides into a growing strand complementary to a single stranded nucleic acid molecule from said nucleic acid sample; and (c) detecting, with the aid of said nanopore, a tag associated with said individual tagged nucleotide during incorporation of said individual tagged nucleotide, wherein said tag is detected with the aid of said nanopore when said nucleotide is associated with said polymerase.

In some embodiments, the tag molecule is not capable of being threaded through the nanopore in a second direction where the second polymer chain does not align adjacent to the second segment.

In some embodiments, said tag is detected a plurality of times while associated with said polymerase.

In some embodiments, an electrode is re-charged between tag detection periods.

In some embodiments, the tag threads into the nanopore during incorporation of the individual tagged nucleotide, and wherein the tag does not thread out of the nanopore when the electrode is re-charged.

In some embodiments, the method distinguishes between an incorporated tagged nucleotide and a non-incorporated tag nucleotide based on the length of time said tagged nucleotide is detected by said nanopore.

In some embodiments, the ratio of the time an incorporated tagged nucleotide is detected by the nanopore to the time a non-incorporated tagged nucleotide is detected by the nanopore is at least 1.5.

In another aspect, a method for nucleic acid sequencing comprises: (a) providing a single stranded nucleic acid to be sequenced; (b) providing a plurality of probes, wherein the probes comprise (i) a hybridization moiety capable of hybridizing with the single stranded nucleic acid, (ii) a loop structure having two ends, wherein each end is attached to the hybridization moiety, and (iii) a cleavable group located in the hybridization moiety between the ends of the loop structure, wherein the loop structure comprises a gate that prevents the loop structure from threading through a nanopore in a reverse direction; (c) polymerizing the plurality of probes in an order determined by hybridization of the hybridization moieties with the single stranded nucleic acid to be sequenced;

cleaving the cleavable groups to provide an expanded thread to be sequenced; (d) threading the expanded thread through a nanopore, wherein the gates prevent the expanded thread from threading through the nanopore in the reverse direction; and (e) detecting, with the aid of the nanopore, the loop structures of the expanded thread in the order determined by hybridization of the hybridization moieties with the single stranded nucleic acid to be sequenced, thereby sequencing the single stranded nucleic acid to be sequenced.

In some embodiments, the loop structure comprises a narrow segment and the gate is a polymer comprising two ends, wherein a first end is affixed to the loop structure adjacent to the narrow segment and a second end is not affixed to the loop structure, wherein the loop structure is capable of being threaded through a nanopore in a first direction where the gate aligns adjacent to the narrow segment.

In some embodiments, the loop structure is not capable of being threaded through the nanopore in the reverse direction where the gate does not align adjacent to the narrow segment.

In some embodiments, the gate base pairs with the loop structure when the gate does not align adjacent to the narrow segment.

In some embodiments, the gate comprises nucleotides.

In some embodiments, the narrow segment comprises a-basic nucleotides.

In some embodiments, the narrow segment comprises a carbon chain.

In some embodiments, an electrode is re-charged between periods of detection.

In some embodiments, the expanded thread does not thread through the nanopore in the reverse direction when the electrode is re-charged.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
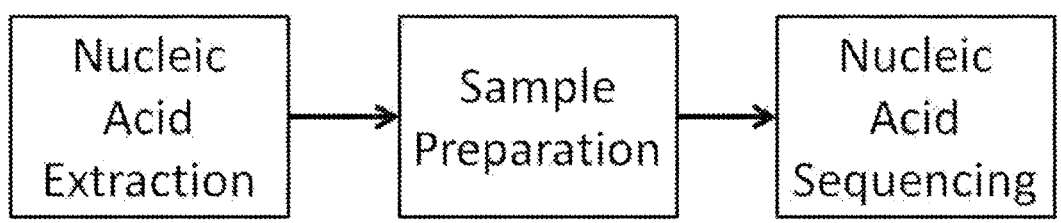
FIG. 1 schematically shows the steps of the method.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nanopore," as used herein, generally refers to a pore, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha hemolysin is an example of a protein nanopore.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double stranded.

The term "polymerase," as used herein, generally refers to any enzyme capable of catalyzing a polymerization reaction. Examples of polymerases include, without limitation, a nucleic acid polymerase, a transcriptase or a ligase. A polymerase can be a polymerization enzyme.

Methods and Systems for Sequencing Samples

Described herein are methods, devices and systems for sequencing nucleic acids using, or with the aid of, one or more nanopores. The one or more nanopores may be in a membrane (e.g., lipid bi-layer) that is disposed adjacent or in sensing proximity to an electrode that is part of, or coupled to, an integrated circuit.

In some examples, a nanopore device includes a single nanopore in a membrane that is adjacent or sensing proximity to an electrode. In other examples, a nanopore device includes at least 1, 2, 3, 4, 5, 6, 7, 8, 9, 10, 20, 30, 40, 50, 60, 70, 80, 90, 100, 1000, or 10,000 nanopores in proximity to a sensor circuit or sensing electrodes. The one or more nanopore may be associated with an individual electrode and sensing integrated circuit or a plurality of electrodes and sensing integrated circuits.

A system may include a reaction chamber that includes one or more nanopore devices. A nanopore device may be an individually addressable nanopore device (e.g., a device that is capable of detecting a signal and providing an output independent of other nanopore devices in the system). An individually addressable nanopore can be individually readable. In some cases, an individually addressable nanopore can be individually writable. As an alternative, an individually addressable nanopore can be individually readable and individually writable. The system can include one or more computer processors for facilitating sample preparation and various operations of the disclosure, such as nucleic acid sequencing. The processor can be coupled to nanopore device.

A nanopore device may include a plurality of individually addressable sensing electrodes. Each sensing electrode can include a membrane adjacent to the electrode, and one or more nanopores in the membrane.

Methods, devices and systems of the disclosure may accurately detect individual nucleotide incorporation events, such as upon the incorporation of a nucleotide into a growing strand that is complementary to a template. An enzyme (e.g., DNA polymerase, RNA polymerase, ligase) may incorporate nucleotides to a growing polynucleotide chain. Enzymes (e.g., polymerases) provided herein can generate polymer chains.

The added nucleotide can be complimentary to the corresponding template nucleic acid strand which is hybridized to the growing strand (e.g., polymerase chain reaction (PCR)). A nucleotide can include a tag (or tag species) that is coupled to any location of the nucleotide including, but not limited to a phosphate (e.g., gamma phosphate), sugar or nitrogenous base moiety of the nucleotide. In some cases, tags are detected while tags are associated with a polymerase during the incorporation of nucleotide tags. The tag may continue to be detected until the tag translocates through the nanopore after nucleotide incorporation and subsequent cleavage and/or release of the tag. In some cases, nucleotide incorporation events release tags from the nucleotides which pass through a nanopore and are detected. The tag can be released by the polymerase, or cleaved/released in any suitable manner including without limitation cleavage by an enzyme located near the polymerase. In this way, the incorporated base may be identified (i.e., A, C, G, T or U) because a unique tag is released from each type of nucleotide (i.e., adenine, cytosine, guanine, thymine or uracil). In some situations, nucleotide incorporation events do not release tags. In such a case, a tag coupled to an incorporated nucleotide is detected with the aid of a nanopore. In some examples, the tag can move through or in proximity to the nanopore and be detected with the aid of the nanopore.

Methods and systems of the disclosure can enable the detection of nucleic acid incorporation events, such as at a resolution of at least 1, 2, 3, 4, 5, 6, 7, 8, 9, 10, 20, 30, 40, 50, 100, 500, 1000, 5000, 10000, 50000, or 100000 nucleic acid bases ("bases") within a given time period. In some examples, a nanopore device is used to detect individual nucleic acid incorporation events, with each event being associated with an individual nucleic acid base. In other examples, a nanopore device is used to detect an event that is associated with a plurality of bases. For examples, a signal sensed by the nanopore device can be a combined signal from at least 2, 3, 4, or 5 bases.

In some instances, the tags do not pass through the nanopore. The tags can be detected by the nanopore and exit the nanopore without passing through the nanopore (e.g., exit from the inverse direction from which the tag entered the nanopore). The chip can be configured to actively expel the tags from the nanopore.

In some instances, the tags are not released upon nucleotide incorporation events. In some cases, nucleotide incorporation events "present" tags to the nanopore (i.e., without releasing the tags). The tags can be detected by the nanopore without being released. The tags may be attached to the nucleotides by a linker of sufficient length to present the tag to the nanopore for detection.

Nucleotide incorporation events may be detected in real-time (i.e., as they occur) and with the aid of a nanopore. In some instances, an enzyme (e.g., DNA polymerase) attached to or in proximity to the nanopore may facilitate the flow of a nucleic acid molecule through or adjacent to a nanopore. A nucleotide incorporation event, or the incorporation of a plurality of nucleotides, may release or present one or more tag species (also "tags" herein), which may be detected by a nanopore. Detection can occur as the tags flow through or adjacent to the nanopore, as the tags reside in the nanopore and/or as the tags are presented to the nanopore. In some cases, an enzyme attached to or in proximity to the nanopore may aid in detecting tags upon the incorporation of one or more nucleotides.

Tags of the disclosure may be atoms or molecules, or a collection of atoms or molecules. A tag may provide an optical, electrochemical, magnetic, or electrostatic (e.g., inductive, capacitive) signature, which signature may be detected with the aid of a nanopore.

Methods described herein may be single-molecule methods. That is, the signal that is detected is generated by a single molecule (i.e., single nucleotide incorporation) and is not generated from a plurality of clonal molecules. The method may not require DNA amplification.

Nucleotide incorporation events may occur from a mixture comprising a plurality of nucleotides (e.g., deoxyribonucleotide triphosphate (dNTP where N is adenosine (A), cytidine (C), thymidine (T), guanosine (G), or uridine (U)). Nucleotide incorporation events do not necessarily occur from a solution comprising a single type of nucleotide (e.g., dATP). Nucleotide incorporation events do not necessarily occur from alternating solutions of a plurality of nucleotides (e.g., dATP, followed by dCTP, followed by dGTP, followed by dTTP, followed by dATP). In some cases, a plurality of nucleotides (e.g., dimers of AA, AG, AC, AT, GA, GG, GG, GC, GT, CA, etc. . . . ) are incorporated by a ligase.

Methods for Nucleic Acid Identification and Sequencing

Methods for sequencing nucleic acids may include retrieving a biological sample having the nucleic acid to be sequenced, extracting or otherwise isolating the nucleic acid sample from the biological sample, and in some cases preparing the nucleic acid sample for sequencing.

FIG. 1 schematically illustrates a method for sequencing a nucleic acid sample. The method comprises isolating the nucleic acid molecule from a biological sample (e.g., tissue sample, fluid sample), and preparing the nucleic acid sample for sequencing. In some instances, the nucleic acid sample is extracted from a cell. Examples of techniques for extracting nucleic acids are using lysozyme, sonication, extraction, high pressures or any combination thereof. The nucleic acid is cell-free nucleic acid in some cases and does not require extraction from a cell.

In some cases, a nucleic acid sample may be prepared for sequencing by a process that involves removing proteins, cell wall debris and other components from the nucleic acid sample. There are many commercial products available for accomplishing this, such as, for example, spin columns. Ethanol precipitation and centrifugation may also be used.

The nucleic acid sample may be partitioned (or fractured) into a plurality of fragments, which may facilitate nucleic acid sequencing, such as with the aid of a device that includes a plurality of nanopores in an array. However, fracturing the nucleic acid molecule(s) to be sequenced may not be necessary.

In some instances, long sequences are determined (i.e., "shotgun sequencing" methods may not be required). Any suitable length of nucleic acid sequence may be determined. For instance, at least about 5, about 10, about 20, about 30, about 40, about 50, about 100, about 200, about 300, about 400, about 500, about 600, about 700, about 800, about 800, about 1000, about 1500, about 2000, about 2500, about 3000, about 3500, about 4000, about 4500, about 5000, about 6000, about 7000, about 8000, about 9000, about 10000, about 20000, about 40000, about 60000, about 80000, or about 100000, and the like bases may be sequenced. In some instances, at least 5, at least 10, at least 20, at least 30, at least 40, at least 50, at least 100, at least 200, at least 300, at least 400, at least 500, at least 600, at least 700, at least 800, at least 800, at least 1000, at least 1500, at least 2000, at least 2500, at least 3000, at least 3500, at least 4000, at least 4500, at least 5000, at least 6000, at least 7000, at least 8000, at least 9000, at least 10000, at least 20000, at least 40000, at least 60000, at least 80000, at least 100000, and the like bases are sequenced. In some instances the sequenced bases are contiguous. In some instances, the sequenced bases are not contiguous. For example, a given number of bases can be sequenced in a row. In another example, one or more sequenced bases may be separated by one or more blocks in which sequence information is not determined and/or available. In some embodiments, a template can be sequenced multiple times (e.g., using a circular nucleic acid template), in some cases generating redundant sequence information. In some cases, software is used to provide the sequence. In some cases, the nucleic acid sample may be partitioned prior to sequencing. In some instances the nucleic acid sample strand may be processed so that a given duplex DNA or RNA/DNA region is made circular such that the corresponding sense and antisense portions of the duplex DNA or RNA/DNA region are included in the circular DNA or circular DNA/RNA molecule. In such an instance, the sequenced bases from such a molecule may allow easier data assembly and checking of base position readings.

Nanopore Sequencing and Molecular Detection

Provided herein are systems and methods for sequencing a nucleic acid molecule with the aid of a nanopore. The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide).

In some cases, as a nucleic acid or tag flows through or adjacent to the nanopore, the sensing circuit detects an electrical signal associated with the nucleic acid or tag. The nucleic acid may be a subunit of a larger strand. The tag may be a byproduct of a nucleotide incorporation event or other interaction between a tagged nucleic acid and the nanopore or a species adjacent to the nanopore, such as an enzyme that cleaves a tag from a nucleic acid. The tag may remain attached to the nucleotide. A detected signal may be collected and stored in a memory location, and later used to construct a sequence of the nucleic acid. The collected signal may be processed to account for any abnormalities in the detected signal, such as errors.

Figure 2A:
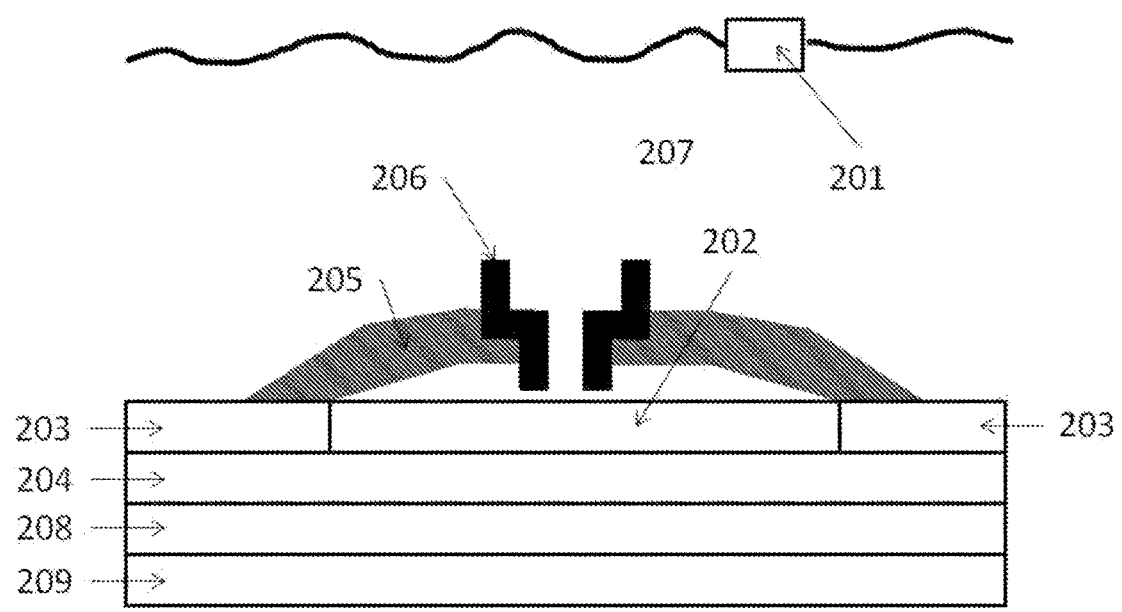
FIGS. 2A, 2B and 2C show examples of nanopore detectors, where FIG. 2A has the nanopore disposed upon the electrode, FIG. 2B has the nanopore inserted in a membrane over a well and FIG. 2C has the nanopore over a protruding electrode.

FIG. 2 shows an examples of a nanopore detector (or sensor) having temperature control, as may be prepared according to methods described in U.S. Patent Application Publication No. 2011/0193570, which is entirely incorporated herein by reference. With reference to FIG. 2A, the nanopore detector comprises a top electrode 201 in contact with a conductive solution (e.g., salt solution) 207. A bottom conductive electrode 202 is near, adjacent, or in proximity to a nanopore 206, which is inserted in a membrane 205. In some instances, the bottom conductive electrode 202 is embedded in a semiconductor 203 in which is embedded electrical circuitry in a semiconductor substrate 204. A surface of the semiconductor 203 may be treated to be hydrophobic. A sample being detected goes through the pore in the nanopore 206. The semiconductor chip sensor is placed in package 208 and this, in turn, is in the vicinity of a temperature control element 209. The temperature control element 209 may be a thermoelectric heating and/or cooling device (e.g., Peltier device). Multiple nanopore detectors may form a nanopore array.

Figure 2B:
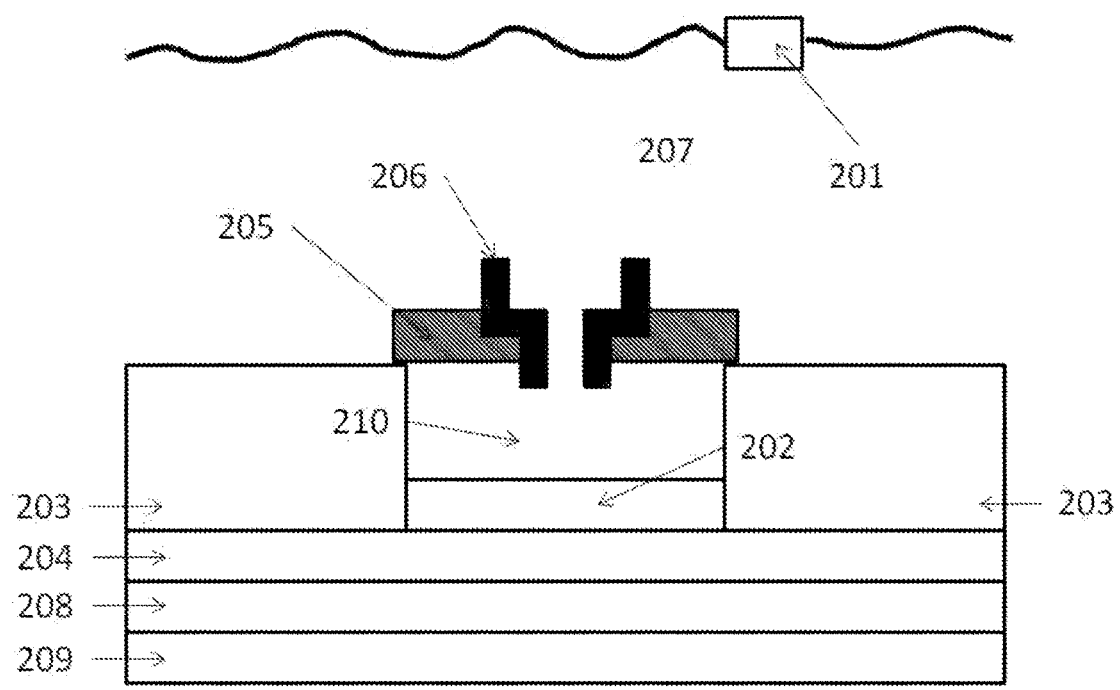
Figure 2C:
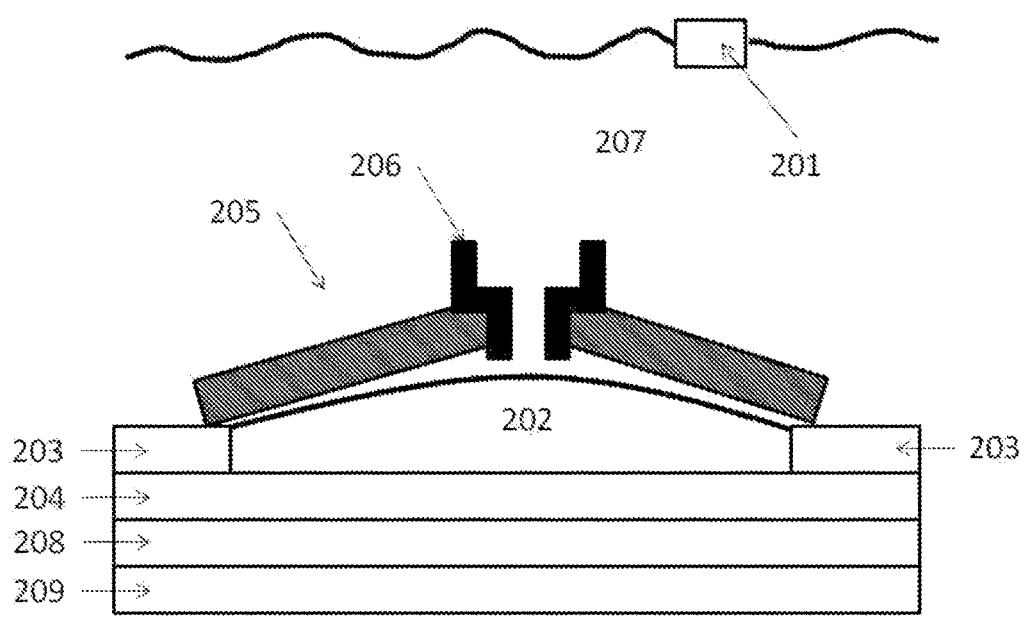

With reference to FIG. 2B, where like numerals represent like elements, the membrane 205 can be disposed over a well 210, where the sensor 202 forms part of the surface of the well. FIG. 2C shows an example in which the electrode 202 protrudes from the treated semiconductor surface 203.

In some examples, the membrane 205 forms on the bottom conductive electrode 202 and not on the semiconductor 203. The membrane 205 in such a case may form coupling interactions with the bottom conductive electrode 202. In some cases, however, the membrane 205 forms on the bottom conductive electrode 202 and the semiconductor 203. As an alternative, the membrane 205 can form on the semiconductor 203 and not on the bottom conductive electrode 202, but may extend over the bottom conductive electrode 202.

Nanopores may be used to sequence nucleic acid molecules indirectly, in some cases with electrical detection. Indirect sequencing may be any method where an incorporated nucleotide in a growing strand does not pass through the nanopore. The nucleic acid molecule may pass within any suitable distance from and/or proximity to the nanopore, in some cases within a distance such that tags released from nucleotide incorporation events are detected in the nanopore.

Byproducts of nucleotide incorporation events may be detected by the nanopore. "Nucleotide incorporation events" are the incorporation of a nucleotide into a growing polynucleotide chain. A byproduct may be correlated with the incorporation of a given type nucleotide. The nucleotide incorporation events are generally catalyzed by an enzyme, such as DNA polymerase, and use base pair interactions with a template molecule to choose amongst the available nucleotides for incorporation at each location.

A nucleic acid sample may be sequenced using tagged nucleotides or nucleotide analogs. In some examples, a method for sequencing a nucleic acid molecule comprises (a) incorporating (e.g., polymerizing) tagged nucleotides, wherein a tag associated with an individual nucleotide is released upon incorporation, and (b) detecting the released tag with the aid of a nanopore. In some instances, the method further comprises directing the tag attached to or released from an individual nucleotide through the nanopore. The released or attached tag may be directed by any suitable technique, in some cases with the aid of an enzyme (or molecular motor) and/or a voltage difference across the pore. Alternative, the released or attached tag may be directed through the nanopore without the use of an enzyme. For example, the tag may be directed by a voltage difference across the nanopore as described herein.

Sequencing with Pre-Loaded Tags

Tags that are released without being loaded into the nanopore can diffuse away from the nanopore and not be detected by the nanopore. This may cause errors in sequencing a nucleic acid molecule (e.g., missing a nucleic acid position or detecting tags in the wrong order). Provided herein are methods for sequencing a nucleic acid molecule where tag molecules are "pre-loaded" into the nanopore before the tag is released from a nucleotide. Pre-loaded tags can be much more likely to be detected by the nanopore than tags that are not pre-loaded (e.g., at least about 100 times more likely). Also, pre-loading tags provides an approach for determining whether or not a tagged nucleotide has been incorporated into a growing nucleic acid strand. Tags that are associated with an incorporated nucleotide can be associated with the nanopore for a longer period of time (e.g., an average of at least about 50 milliseconds (ms)) than tags that pass through (and are detected by) the nanopore without being incorporated (e.g., an average of less than about 1 ms). In some examples, the tag associated with an incorporated nucleotide can be associated with the nanopore or held or otherwise coupled to an enzyme (e.g., polymerase) adjacent to the nanopore for an average time period of at least about 1 millisecond (ms), 20 ms, 30 ms, 40 ms, 50 ms, 100 ms, 200 ms, or greater than 250 ms. In some examples, a tag signal associated with an incorporated nucleotide can have an average detection lifetime of at least about 1 millisecond (ms), 20 ms, 30 ms, 40 ms, 50 ms, 100 ms, 200 ms, or greater than 250 ms. The tag may be coupled to an incorporated nucleotide coupled. A tag signal having an average detection lifetime that is less than an average detection lifetime attributed to an incorporated nucleotide (e.g., less than about 1 ms) may be attributed to an unincorporated nucleotide coupled to the tag. In some cases, an average detection lifetime of at least 'x' can be attributed to an incorporated nucleotide, and an average detection lifetime less than 'x' can be attributed to an unincorporated nucleotide. In some examples, 'x' can be 0.1 ms, 1 ms, 20 ms, 30 ms, 40 ms, 50 ms, 100 ms, 1 second.

A tag may be detected with the aid of a nanopore device having at least one nanopore in a membrane. The tag may be associated with an individual tagged nucleotide during incorporation of the individual tagged nucleotide. Methods provided herein may involve differentiating, with the aid of the nanopore, a tag associated with the individual tagged nucleotide from one or more tags associated with one or more unincorporated individual tagged nucleotides. In some cases, the nanopore device detects a tag associated with an individual tagged nucleotide during incorporation. The tagged nucleotides (whether incorporated into a growing nucleic acid stand or unincorporated) are detected, determined, or differentiated for a given period of time by the nanopore device, in some cases with the aid of an electrode and/or nanopore of the nanopore device. The time period within which the nanopore device detects the tag may be shorter, in some cases substantially shorter, than the time period in which the tag and/or nucleotide coupled to the tag is held by an enzyme, such as an enzyme facilitating the incorporation of the nucleotide into a nucleic acid strand (e.g., a polymerase). In some examples, the tag can be detected by the electrode a plurality of times within the time period that the incorporated tagged nucleotide is associated with the enzyme. For instance, the tag can be detected by the electrode at least 1, 2, 3, 4, 5, 6, 7, 8, 9, 10, 20, 30, 40, 50, 60, 70, 80, 90, 100, 200, 300, 400, 500, 1000, 10,000, 100,000, or 1,000,000 times within the time period that the incorporated tagged nucleotide is associated with the enzyme.

Figure 18:
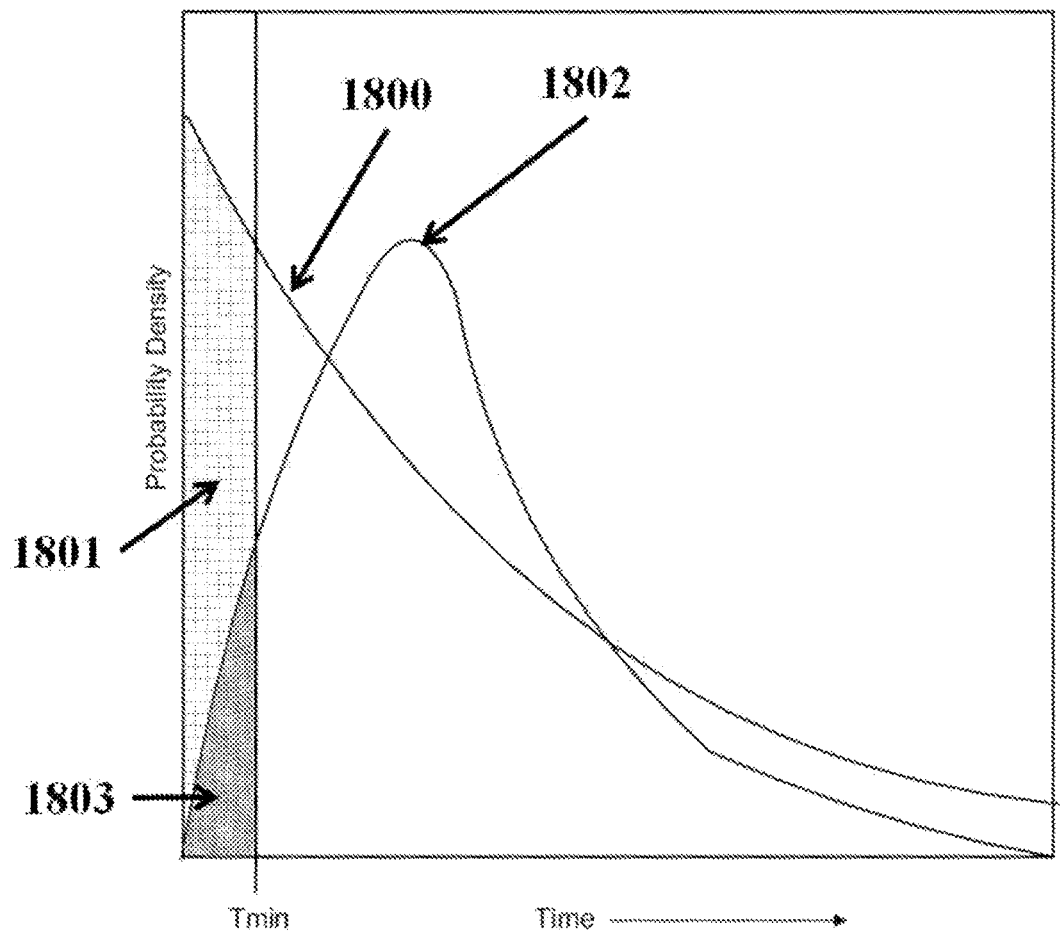
FIG. 18 shows the probability density for residence time of a polymerase exhibiting two limiting kinetic steps.

Any recitations of a time of detection or an average time of detection may allow for a proportion of detection times to fall above or below the stated time or average time. In some cases, the detection times when sequencing a plurality of nucleic acid bases are statistically distributed (e.g., an exponential distribution or a Gaussian distribution). An exponential distribution can have a relatively large percentage of detection times that fall below the average detection time, as seen in FIG. 18, for example.

In some examples, pre-loading a tag comprises directing at least a portion of the tag through at least a portion of a nanopore while the tag is attached to a nucleotide, which nucleotide has been incorporated into a nucleic acid strand (e.g., growing nucleic acid strand), is undergoing incorporation into the nucleic acid strand, or has not yet been incorporated into the nucleic acid strand but may undergo incorporation into the nucleic acid strand. In some examples, pre-loading the tag comprises directing at least a portion of the tag through at least a portion of the nanopore before the nucleotide has been incorporated into the nucleic acid strand or while the nucleotide is being incorporated into the nucleic acid strand. In some cases, pre-loading the tag can include directing at least a portion of the tag through at least a portion of the nanopore after the nucleotide has been incorporated into the nucleic acid strand.

Figure 3:
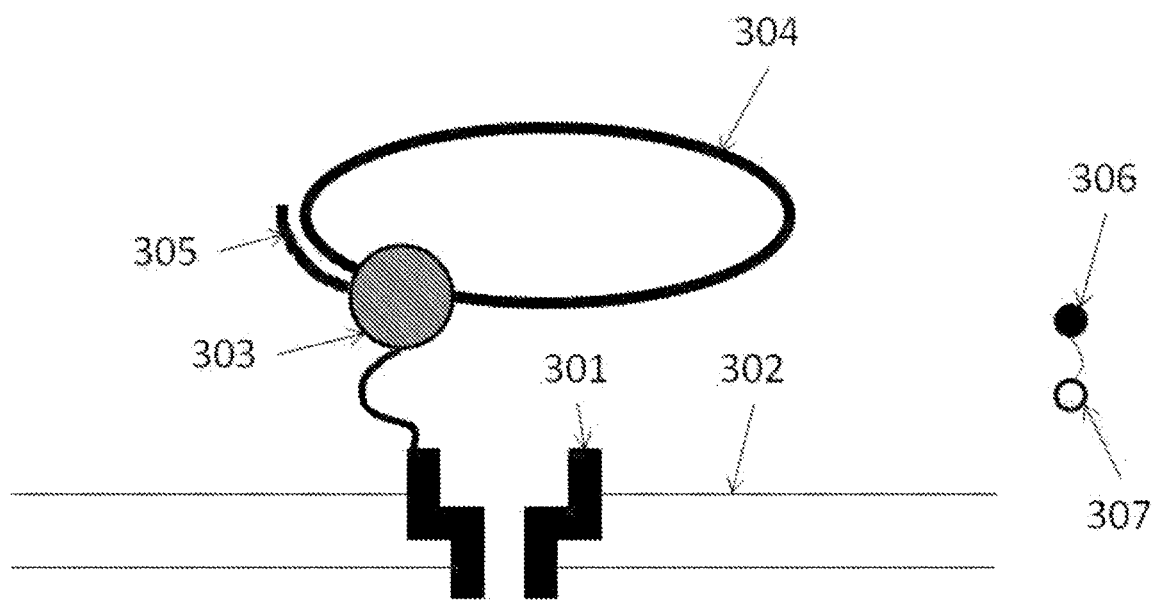
FIG. 3 illustrates components of the device and method.

FIG. 3 shows the principal components of the method. Here, a nanopore 301 is formed in a membrane 302. An enzyme 303 (e.g., a polymerase such as DNA polymerase) is associated with the nanopore. In some cases, the enzyme is covalently attached to the nanopore as described below. The polymerase is associated with a single stranded nucleic acid molecule 304 to be sequenced. The single stranded nucleic acid molecule is circular in some instances, but this is not required. In some cases, the nucleic acid molecule is linear. In some embodiments, a nucleic acid primer 305 is hybridized to a portion of the nucleic acid molecule. In some cases, the primer has a hairpin (e.g., to prevent threading the displaced newly created nucleic acid strand in to the nanopore after the first pass around a circular template). The polymerase catalyzes the incorporation of nucleotides onto the primer using the single stranded nucleic acid molecule as a template. The nucleotides 306 comprise tag species ("tags") 307 as described herein.

Figure 4:
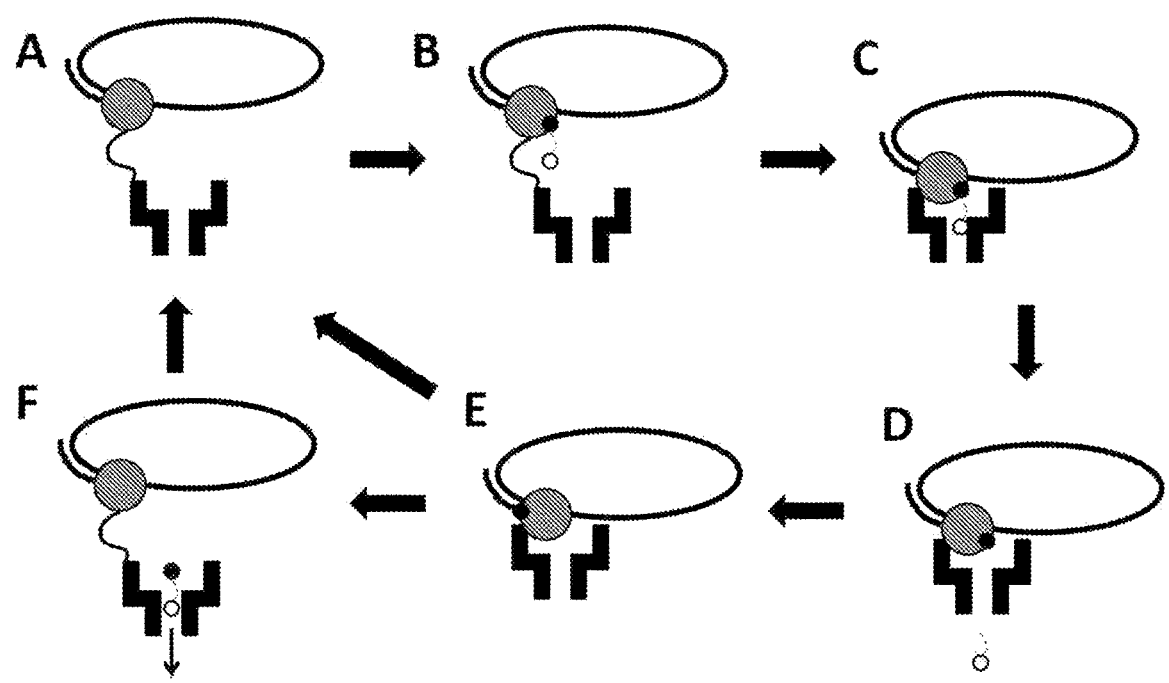
FIG. 4 illustrates a method for nucleic acid sequencing where released tags are detected by a nanopore while the tags are associated with a polymerase.

FIG. 4 schematically illustrates a method for nucleic acid sequencing with the aid of "pre-loaded" tags. Part A shows the principal components as described in FIG. 3. Part C shows the tag loaded into the nanopore. A "loaded" tag may be one that is positioned in and/or remains in or near the nanopore for an appreciable amount of time, such as, e.g., at least 0.1 millisecond (ms), at least 1 ms, at least 5 ms, at least 10 ms, at least 50 ms, at least 100 ms, or at least 500 ms, or at least 1000 ms. In some cases, a tag that is "pre-loaded" is loaded in the nanopore prior to being released from the nucleotide. In some instances, a tag is pre-loaded if the probability of the tag passing through (and/or being detected by) the nanopore after being released upon a nucleotide incorporation event is suitably high, such as, e.g., at least 90%, at least 95%, at least 99%, at least 99.5%, at least 99.9%, at least 99.99%, or at least 99.999%.

In the transition from part A to part B, a nucleotide has become associated with the polymerase. The associated nucleotide is base paired with the single stranded nucleic acid molecule (e.g., A with T and G with C). It is recognized that a number of nucleotides may become transiently associated with the polymerase that are not base paired with the single stranded nucleic acid molecule. Non-paired nucleotides may be rejected by the polymerase and generally only in the case where the nucleotides are base paired does incorporation of the nucleotide proceed. Non-paired nucleotides are generally rejected within a time scale that is shorter than the time scale for which correctly paired nucleotides remain associated with the polymerase. Non-paired nucleotides may be rejected within a time period (mean) of at least about 100 nanoseconds (ns), 1 ms, 10 ms, 100 ms, 1 second, while correctly paired nucleotides remain associated with the polymerase for a longer time period, such as a mean time period of at least about 1 milliseconds (ms), 10 ms, 100 ms, 1 second, or 10 seconds. The current passing through the nanopore during part A and B of FIG. 4 may be between 3 and 30 picoamps (pA) in some cases.

Figure 17:
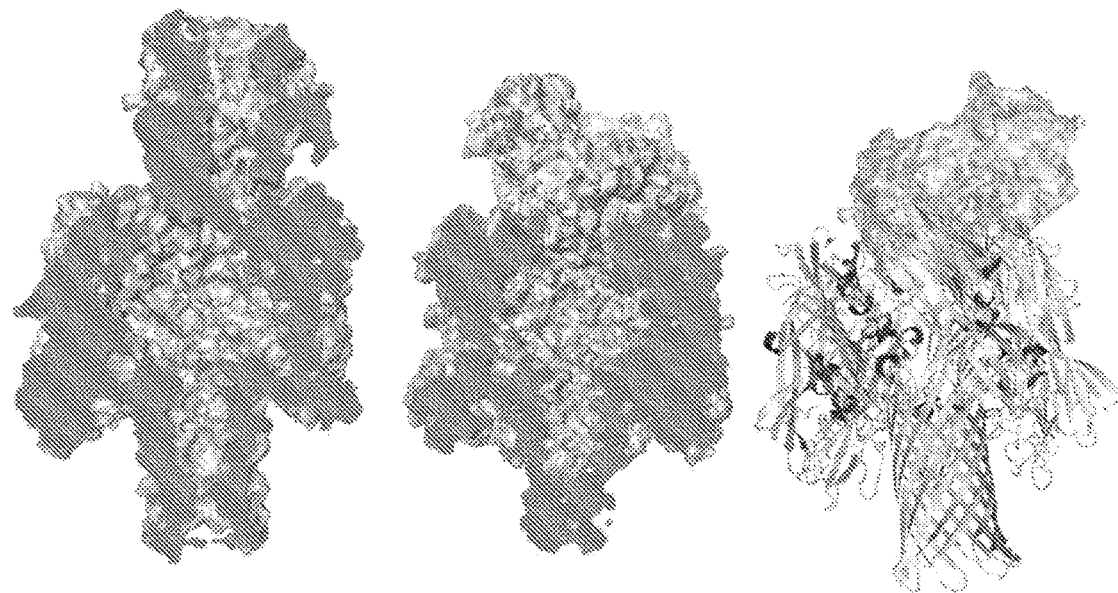
FIG. 17 shows docking of the phi29 polymerase to a hemolysin nanopore.

FIG. 4, part C depicts docking of the polymerase to the nanopore. The polymerase may be drawn to the nanopore with the aid of a voltage (e.g., DC or AC voltage) applied to a membrane in which the nanopore resides, or the nanopore. FIG. 17 also depicts docking of the polymerase to the nanopore, in this case phi29 DNA Polymerase (φ29 DNA Polymerase) with alpha-hemolysin nanopore. The tag can be pulled into the nanopore during docking by an electrical force, such as a force generated in the presence of an electric field generated by an applied voltage to the membrane and/or the nanopore. In some embodiments, the current flowing through the nanopore during part C of FIG. 4 is about 6 pA, about 8 pA, about 10 pA, about 15 pA, or about 30 pA. The polymerase undergoes an isomerization and a transphosphorylation reaction to incorporate the nucleotide into the growing nucleic acid molecule and release the tag molecule.

In part D, the tag is depicted passing through the nanopore. The tag is detected by the nanopore as described herein. Repeating the cycle (i.e., parts A through E or A through F) allows for sequencing the nucleic acid molecule.

In some cases, tagged nucleotides that are not incorporated into the growing nucleic acid molecule will also pass through the nanopore as seen in part F of FIG. 4. The un-incorporated nucleotide can be detected by the nanopore in some instances, but the method provides a means for distinguishing between an incorporated nucleotide and an un-incorporated nucleotide based at least in part on the time for which the nucleotide is detected in the nanopore. Tags bound to un-incorporated nucleotides pass through the nanopore quickly and are detected for a short period of time (e.g., less than 100 ms), while tags bound to incorporated nucleotides are loaded into the nanopore and detected for a long period of time (e.g., at least 100 ms).

In some embodiments, the method distinguishes between an incorporated (e.g., polymerized) tagged nucleotide and a non-incorporated tag nucleotide based on the length of time the tagged nucleotide is detected by the nanopore. The tag can remain in proximity to the nanopore for a longer time when being incorporated than when not being incorporated. In some instances, the polymerase is mutated to increase the time difference between incorporated tagged nucleotides and non-incorporated tagged nucleotides. The ratio of the time an incorporated tagged nucleotide is detected by the nanopore to the time a non-incorporated tag is detected by the nanopore can be any suitable value. In some embodiments, the ratio of the time an incorporated tagged nucleotide is detected by the nanopore to the time a non-incorporated tag is detected by the nanopore is about 1.5, about 2, about 3, about 4, about 5, about 6, about 7, about 8, about 9, about 10, about 12, about 14, about 16, about 18, about 20, about 25, about 30, about 40, about 50, about 100, about 200, about 300, about 400, about 500, or about 1000. In some embodiments, the ratio of the time an incorporated (e.g., polymerized) tagged nucleotide is detected by the nanopore to the time a non-incorporated tag is detected by the nanopore is at least about 1.5, at least about 2, at least about 3, at least about 4, at least about 5, at least about 6, at least about 7, at least about 8, at least about 9, at least about 10, at least about 12, at least about 14, at least about 16, at least about 18, at least about 20, at least about 25, at least about 30, at least about 40, at least about 50, at least about 100, at least about 200, at least about 300, at least about 400, at least about 500, or at least about 1000.

The time at which the tag is loaded into (and/or detected by) the nanopore is any suitable value. In some instances, the tag is detected by the nanopore for an average of about 10 milliseconds (ms), about 20 ms, about 30 ms, about 40 ms, about 50 ms, about 60 ms, about 80 ms, about 100 ms, about 120 ms, about 140 ms, about 160 ms, about 180 ms, about 200 ms, about 220 ms, about 240 ms, about 260 ms, about 280 ms, about 300 ms, about 400 ms, about 500 ms, about 600 ms, about 800 ms, or about 1000 ms. In some instances, the tag is detected by the nanopore for an average of at least about 10 milliseconds (ms), at least about 20 ms, at least about 30 ms, at least about 40 ms, at least about 50 ms, at least about 60 ms, at least about 80 ms, at least about 100 ms, at least about 120 ms, at least about 140 ms, at least about 160 ms, at least about 180 ms, at least about 200 ms, at least about 220 ms, at least about 240 ms, at least about 260 ms, at least about 280 ms, at least about 300 ms, at least about 400 ms, at least about 500 ms, at least about 600 ms, at least about 800 ms, or at least about 1000 ms.

In some examples, a tag generating a signal for a time period of at least about 1 ms, at least about 10 ms, at least about 50 ms, at least about 80 ms, at least about 100 ms, at least about 120 ms, at least about 140 ms, at least about 160 ms, at least about 180 ms, at least about 200 ms, at least about 220 ms, at least about 240 ms, or at least about 260 ms is attributed to a nucleotide that has been incorporated into a growing strand that is complementary to at least a portion of a template. In some cases, a tag generating a signal for a time period less than about 100 ms, less than about 80 ms, less than about 60 ms, less than about 40 ms, less than about 20 ms, less than about 10 ms, less than about 5 ms, or less than about 1 ms is attributed to a nucleotide that has not been incorporated into the growing strand.

Figure 5:
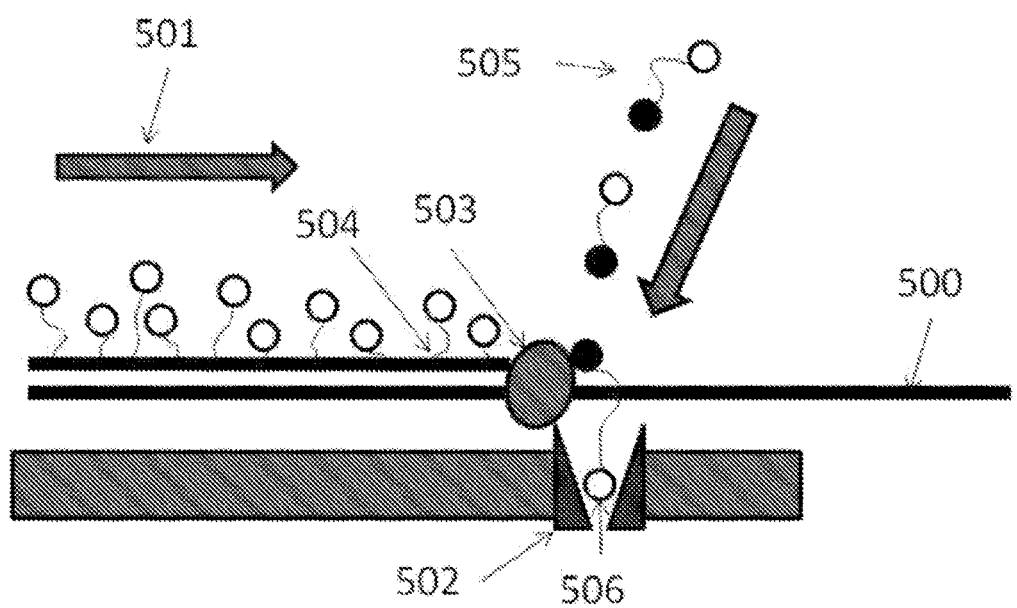
FIG. 5 illustrates a method for nucleic acid sequencing where tags are not released upon nucleotide incorporation events and are detected by a nanopore.

The nucleic acid molecule can be linear (as seen in FIG. 5). In some cases, as seen in FIG. 3, the nucleic acid molecule 304 is circular (e.g., circular DNA, circular RNA). The circularized (e.g., single stranded) nucleic acid can be sequenced a plurality of times (e.g., as the polymerase 303 progresses completely around the circle it starts re-sequencing portions of the template). The circular DNA may be sense and antisense strands for the same genomic positions ligated together (in some cases allowing more robust and accurate reads to occur). The circular nucleic acid can be sequenced until a suitable accuracy is achieved (e.g., at least 95%, at least 99%, at least 99.9%, or at least 99.99% accuracy). In some cases, the nucleic acid is sequenced at least 2, at least 3, at least 4, at least 5, at least 6, at least 7, at least 8, at least 9, at least 10, at least 12, at least 15, at least 20 times, at least 40 times, at least 50 times, at least 100 times, or at least 1000 times.

In an aspect, the method and devices described herein distinguish between incorporated nucleotides and non-incorporated nucleotides based in part on incorporated nucleotides being detected and/or detectable by the nanopore for a longer period of time than non-incorporated nucleotides. In some instances, displacement of a second nucleic acid strand hybridized to the nucleic acid strand being sequenced (double stranded nucleic acid) increases the time difference between detection of incorporated and un-incorporated nucleotides. With reference to FIG. 3, after the first sequencing, the polymerase may encounter double stranded nucleic acid (e.g., starting from when it encounters the primer 305) and the second nucleic acid strand may need to be displaced from the template to continue sequencing. This displacement can slow down the polymerase and/or rate of nucleotide incorporation events compared to when the template is single stranded.

Figure 25:
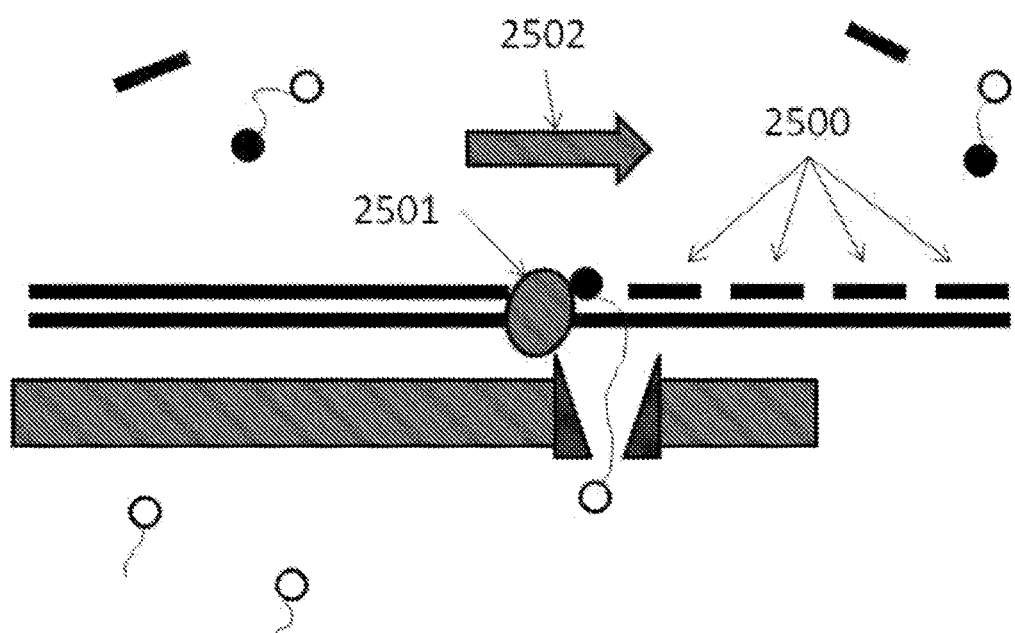
FIG. 25 shows the use of oligonucleotide speed-bumps to slow down the progression of a nucleic acid polymerase.

In some instances, the template nucleic acid molecule is double stranded from hybridizations of oligonucleotides to the single stranded template. FIG. 25 shows an example in which a plurality of oligonucleotides 2500 are hybridized. Progression of the polymerase 2501 in the direction indicated 2502 displaces the oligonucleotides from the template. The polymerase can progress more slowly than if the oligonucleotides were not present. In some cases, use of the oligonucleotides as described herein improves the resolution between incorporated nucleotides and non-incorporated nucleotides based in part on incorporated nucleotides being detected and/or detectable by the nanopore for a longer period of time than non-incorporated nucleotides. The oligonucleotides can be any suitable length (e.g., about 4, about 5, about 6, about 7, about 8, about 9, about 10, about 12, about 14, about 16, about 18, or about 20 bases long). The oligonucleotides can comprise natural bases (e.g., adenine (A), cytosine (C), guanine (G), thymine (T) and/or uracil (U)), universal bases, (e.g., 5-nitroindole, 3-nitropyrrole, 3-methyl 7-propynyl isocarbostyril (PIM), 3-methyl isocarbostyril (MICS), and/or 5-methyl isocarbostyril (5MICS)), or any combination thereof in any proportion.

In some cases, nucleic acid polymerases proceed more slowly with methylated nucleic acid templates than with non-methylated nucleic acid templates. In an aspect, the method and/or devices described herein use methylated nucleic acids and/or methylate the nucleic acid molecule. In some cases, a methyl group is present on and/or added to the 5 position of the cytosine pyrimidine ring and/or the number 6 nitrogen of the adenine purine ring. The nucleic acid to be sequenced may be isolated from an organism that methylates the nucleic acid. In some cases, the nucleic acid can be methylated in-vitro (e.g., by using a DNA methyltransferase enzyme). Time may be used to differentiate methylated bases from non-methylated bases. This may enable epi genetics studies.

In some cases, methylated bases are distinguishable from non-methylated bases based on a characteristic current or a characteristic shape of a current/time plot. For example, a tagged nucleotide can result in a different blockage current depending on whether the nucleic acid template has a methylated base at a given position (e.g., due to conformational differences in the polymerase). In some cases, C and/or A bases are methylated and incorporation of the corresponding G and/or T tagged nucleotides shifts the electrical current.

Enzymes for Nucleic Acid Sequencing

The method can use an enzyme (e.g., a polymerase, transciptase or a ligase) to sequence a nucleic acid molecule with the nanopore and tagged nucleotides as described herein. In some cases, the method involves incorporating (e.g., polymerizing) tagged nucleotides with the aid of a polymerase (e.g., DNA polymerase). In some cases, the polymerase has been mutated to allow it to accept tagged nucleotides. The polymerase can also be mutated to increase the time for which the tag is detected by the nanopore (e.g., the time of part C of FIG. 4).

In some embodiments, the enzyme is any enzyme that creates a nucleic acid strand by phosphate linkage of nucleotides. In some cases, the DNA polymerase is 9° N polymerase or a variant thereof, E. Coli DNA polymerase I, Bacteriophage T4 DNA polymerase, Sequenase, Taq DNA polymerase, 9° N polymerase (exo-)A485L/Y409V, phi29 DNA Polymerase ( 29 DNA Polymerase), Bet polymerase, or variants, mutants, or homologues thereof. A homologue can have any suitable percentage homology, including without limitation at least about 30%, at least about 40%, at least about 50%, at least about 60%, at least about 70%, at least about 80%, at least about 90%, or at least about 95% sequence identity.

With reference to FIG. 3, the enzyme 303 may be attached to the nanopore 301. Suitable methods for attaching the enzyme to the nanopore include cross-linking such as the formation of intra-molecular disulfide bonds. The nanopore and the enzyme may also be a fusion protein (i.e., encoded by a single polypeptide chain). Methods for producing fusion proteins may include fusing the coding sequence for the enzyme in frame and adjacent to the coding sequence for the nanopore (without a stop codon in between) and expressing this fusion sequence from a single promoter. In some examples, the enzyme 303 may be attached or otherwise coupled to the nanopore 301 using molecular staples or protein fingers. In some cases, the enzyme is attached through an intermediate molecule, such as for example biotin conjugated to both the enzyme and the nanopore with streptavidin tetramers linked to both biotins. The enzyme can also be attached to the nanopore with an antibody. In some cases, proteins that form a covalent bond between each other (e.g., the SpyTag™/SpyCatcher™ system) are used to attach the polymerase to the nanopore. In some cases, phosphatase enzymes or an enzyme that cleaves the tag from the nucleotide are also attached to the nanopore.

The DNA polymerase is phi29 DNA Polymerase in some instances. The polymerase can be mutated to facilitate and/or improve the efficiency of the mutated polymerase for incorporation of tagged nucleotides into a growing nucleic acid molecule relative to the non-mutated polymerase. The polymerase can be mutated to improve entry of the nucleotide analogue (e.g., tagged nucleotide) into the active site region of the polymerase and/or mutated for coordinating with the nucleotide analogues in the active region.

In some embodiments, the polymerase has an active region that has an amino acid sequence that is homologous (e.g., at least 70%, at least 80%, or at least 90% amino acid positions identical) to the active region of a polymerase that accepts nucleotide analogs (e.g., VentA 488L).

Suitable mutations of phi29 DNA polymerase include, but are not limited to a deletion of residues 505-525, a deletion within residues 505-525, a K135A mutation, an E375H mutation, an E375S mutation, an E375K mutation, an E375R mutation, an E375A mutation, an E375Q mutation, an E375 W mutation, an E375Y mutation, an E375F mutation, an E486A mutation, an E486D mutation, a K512A mutation, and combinations thereof. In some cases, the DNA polymerase further comprises an L384R mutation. Suitable DNA polymerases are described in U.S. Patent Publication No. 2011/0059505, which is entirely incorporated herein by reference. In some embodiments, the polymerase is a phi29 DNA polymerase having the mutations N62D, L253A, E375Y, A484E and/or K512Y.

Suitable mutations to the phi29 polymerase are not limited to mutations that confer improved incorporation of tagged nucleotides. Other mutations (e.g., amino acid substitutions, insertions, deletions, and/or exogenous features) can confer, without limitation, enhanced metal ion coordination, reduced exonuclease activity, reduced reaction rates at one or more steps of the polymerase kinetic cycle, decreased branching fraction, altered cofactor selectivity, increased yield, increased thermostability, increased accuracy, increased speed, increased readlength, increased salt tolerance and the like relative to the non-mutated (wild type) phi29 DNA polymerase.

Suitable mutations of phi29 DNA polymerase include, but are not limited to a mutation at position E375, a mutation at position K512, and a mutation at one or more positions selected from the group consisting of L253, A484, V250, E239, Y224, Y148, E508, and T368.

In some embodiments, the mutation at position E375 comprises an amino acid substitution selected from the group consisting of E375Y, E375F, E375R, E375Q, E375H, E375L, E375A, E375K, E375S, E375T, E375C, E375G, and E375N. In some instances, the mutation at position K512 comprises an amino acid substitution selected from the group consisting of K512Y, K512F, K512I, K512M, K512C, K512E, K512G, K512H, K512N, K512Q, K512R, K512V, and K512H. In one embodiment, the mutation at position E375 comprises an E375Y substitution and the mutation at position K512 comprises a K512Y substitution.

In some cases, the mutated phi29 polymerase comprises one or more amino acid substitutions selected from the group consisting of L253A, L253C, L253S, A484E, A484Q, A484N, A484D, A484K, V250I, V250Q, V250L, V250M, V250C, V250F, V250N, V250R, V250T, V250Y, E239G, Y224K, Y224Q, Y224R, Y148I, Y148A, Y148K, Y148F, Y148C, Y148D, Y148E, Y148G, Y148H, Y148K, Y148L, Y148M, Y148N, Y148P, Y148Q, Y148R, Y148S, Y148T, Y148V, Y148W, E508R, and E508K.

In some instances, the phi29 DNA polymerase comprises a mutation at one or more positions selected from the group consisting of D510, E515, and F526. The mutations may comprise one or more amino acid substitutions selected from the group consisting of D510K, D510Y, D510R, D510H, D510C, E515Q, E515K, E515D, E515H, E515Y, E515C, E515M, E515N, E515P, E515R, E515S, E515T, E515V, E515A, F526L, F526Q, F526V, F526K, F526I, F526A, F526T, F526H, F526M, F526V, and F526Y. Examples of DNA polymerases that may be used with methods of the disclosure are described in U.S. Patent Pub. No. 2012/0034602, which is entirely incorporated herein by reference.

The polymerase can have kinetic rate profile that is suitable for detection of the tags by the nanopore. The rate profile can refer to the overall rate of nucleotide incorporation and/or a rate of any step of nucleotide incorporation such as nucleotide addition, enzymatic isomerization such as to or from a closed state, cofactor binding or release, product release, incorporation of nucleic acid into the growing nucleic acid, or translocation.

Systems of the disclosure can permit the detection of one or more events associated with sequencing. The events may be kinetically observable and/or non-kinetically observable (e.g., a nucleotide migrating through a nanopore without coming in contact with a polymerase).

A polymerase can be adapted to permit the detection of sequencing events. In some embodiments, the rate profile of a polymerase can be such that a tag is loaded into (and/or detected by) the nanopore for an average of about 0.1 milliseconds (ms), about 1 ms, about 5 ms about 10 ms, about 20 ms, about 30 ms, about 40 ms, about 50 ms, about 60 ms, about 80 ms, about 100 ms, about 120 ms, about 140 ms, about 160 ms, about 180 ms, about 200 ms, about 220 ms, about 240 ms, about 260 ms, about 280 ms, about 300 ms, about 400 ms, about 500 ms, about 600 ms, about 800 ms, or about 1000 ms. In some embodiments, the rate profile of a polymerase can be such that a tag is loaded into (and/or detected by) the nanopore for an average of at least about 5 milliseconds (ms), at least about 10 ms, at least about 20 ms, at least about 30 ms, at least about 40 ms, at least about 50 ms, at least about 60 ms, at least about 80 ms, at least about 100 ms, at least about 120 ms, at least about 140 ms, at least about 160 ms, at least about 180 ms, at least about 200 ms, at least about 220 ms, at least about 240 ms, at least about 260 ms, at least about 280 ms, at least about 300 ms, at least about 400 ms, at least about 500 ms, at least about 600 ms, at least about 800 ms, or at least about 1000 ms. In some instances, the tag is detected by the nanopore for an average between about 80 ms and 260 ms, between about 100 ms and 200 ms, or between about 100 ms and 150 ms.

In some cases, the polymerase reaction exhibits two kinetic steps which proceed from an intermediate in which a nucleotide or a polyphosphate product is bound to the polymerase enzyme, and two kinetic steps which proceed from an intermediate in which the nucleotide and the polyphosphate product are not bound to the polymerase enzyme. The two kinetic steps can include enzyme isomerization, nucleotide incorporation, and product release. In some cases, the two kinetic steps are template translocation and nucleotide binding.

FIG. 18 illustrates that where one kinetic step is present, there can be an exponentially decreasing probability of a given residence time of the tag in the nanopore as the residence time increases 1800, providing a distribution in which there is a relatively high probability that the residence time of the tag in the nanopore will be short 1801 (and therefore potentially not detected by the nanopore). FIG. 18 also illustrates that for the case in which there are two or more kinetic steps (e.g., observable or "slow" steps) 1802, the probability of very fast residence times of the tag in the nanopore is relatively low 1803 as compared to the case having one slow step 1801. Stated another way, the addition of two exponential functions can result in a Gaussian function or distribution 1802. In addition, the probability distribution for two slow steps exhibits a peak in the plot of probability density versus residence time 1802. This type of residence time distribution can be advantageous for nucleic acid sequencing as described herein (e.g., where it is desired to detect a high proportion of incorporated tags). Relatively more nucleotide incorporation events load the tag into the nanopore for a period of time greater than a minimum time ($T_{min}$, which can be greater than 100 ms in some instances).

In some cases, the phi29 DNA polymerase is mutated relative to the wild type enzyme to provide two kinetically slow steps and/or to provide a rate profile that is suitable for detecting of tags by the nanopore. In some cases, the phi29 DNA polymerase has at least one amino acid substitution or combination of substitutions selected from position 484, position 198, and position 381. In some embodiments, the amino acid substitutions are selected from E375Y, K512Y, T368F, A484E, A484Y, N387L, T372Q, T372L, K478Y, I370W, F198W, L381A, and any combination thereof. Suitable DNA polymerases are described in U.S. Pat. No. 8,133,672, which is entirely incorporated herein by reference.

The kinetics of the enzyme can also be affected and/or controlled by manipulating the content of the solution in contact with the enzyme. For example, non-catalytic divalent ions (e.g., ions that do not promote polymerase function such as strontium ($Sr^{2+}$)) can be mixed with catalytic divalent ions (e.g., ions that promote polymerase function such as magnesium ($Mg^{2+}$) and/or manganese ($Mn^{2-}$)) with to slow the polymerase down. The ratio of catalytic to non-catalytic ions can be any suitable value, including about 20, about 15, about 10, about 9, about 8, about 7, about 6, about 5, about 4, about 3, about 2, about 1, about 0.5, about 0.2, or about 0.1. In some cases, the ratio depends on the concentration of mono-valent salt (e.g., potassium chloride (KCl)), temperature and/or pH. In one example, the solution comprises 1 micro-molar $Mg^{2+}$ and 0.25 micro-molar $Sr^{2-}$. In another example, the solution comprises 3 micro-molar $Mg^{2+}$ and 0.7 micro-molar $Sr^{2+}$. The concentration of magnesium ($Mg^{2+}$) and manganese ($Mn^{2+}$) can be any suitable value, and can be varied to affect the kinetics of the enzyme. In one example, the solution comprises 1 micro-molar $Mg^{2+}$ and 0.25 micro-molar $Mn^{2+}$. In another example, the solution comprises 3 micro-molar $Mg^{2+}$ and 0.7 micro-molar $Mn^{2+}$.

Nanopore Sequencing of Pre-Loaded Tag Molecules

Tags can be detected without being released from incorporated nucleotides during synthesis of a nucleic acid strand that is complementary to a target strand. The tags can be attached to the nucleotides with a linker such that the tag is presented to the nanopore (e.g., the tag hangs down into or otherwise extend through at least a portion of the nanopore). The length of the linker may be sufficiently long so as to permit the tag to extend to or through at least a portion of the nanopore. In some instances, the tag is presented to (i.e., moved into) the nanopore by a voltage difference. Other ways to present the tag into the pore may also be suitable (e.g., use of enzymes, magnets, electric fields, pressure differential). In some instances, no active force is applied to the tag (i.e., the tag diffuses into the nanopore).

An aspect of the invention provides a method for sequencing a nucleic acid. The method comprises incorporating (e.g., polymerizing) tagged nucleotides. A tag associated with an individual nucleotide can be detected by a nanopore without being released from the nucleotide upon incorporation.

A chip for sequencing a nucleic acid sample can comprise a plurality of individually addressable nanopores. An individually addressable nanopore of the plurality can contain at least one nanopore formed in a membrane disposed adjacent to an integrated circuit. Each individually addressable nanopore can be capable of detecting a tag associated with an individual nucleotide. The nucleotide can be incorporated (e.g., polymerized) and the tag may not released from the nucleotide upon incorporation.

An example of the method is depicted in FIG. 5. Here, the nucleic acid strand 500 passes across or in proximity to (but not through as indicated by the arrow at 501) the nanopore 502. An enzyme 503 (e.g., DNA polymerase) extends a growing nucleic acid strand 504 by incorporating one nucleotide at a time using a first nucleic acid molecule as a template 500 (i.e., the enzyme catalyzes nucleotide incorporation events). Tags are detected by the nanopore 502. The tags may reside in the nanopore for a period of time.

The enzyme 503 may be attached to the nanopore 502. Suitable methods for attaching the enzyme to the nanopore include cross-linking such as the formation of intra-molecular disulfide bonds and/or creation of a fusion protein as described above. In some cases, phosphatase enzymes are also attached to the nanopore. These enzymes may further bind to the remaining phosphates on a cleaved tag and produce clearer signals by further increasing the dwell time in the nanopore. Suitable DNA polymerases include Phi29 DNA Polymerase (φ29 DNA Polymerase) and further including, but not limited to those described above.

With continued reference to FIG. 5, the enzyme draws from a pool of nucleotides (filled circles at indication 505) attached to tag molecules (open circles at indication 505). Each type of nucleotide is attached to a different tag molecule so that when the tags reside in the nanopore 502, they may be differentiated from each other based on the signal that is generated in or associated with the nanopore.

In some cases, the tags are presented to the nanopore upon nucleotide incorporation events and are released from the nucleotide. In some cases, the released tags go through the nanopore. The tags do not pass through the nanopore in some instances. In some instances, a tag that has been released upon a nucleotide incorporation event is distinguished from a tag that may flow through the nanopore, but has not been released upon a nucleotide incorporation event at least in part by the dwell time in the nanopore. In some cases, tags that dwell in the nanopore for at least about 100 milliseconds (ms) are released upon nucleotide incorporation events and tags that dwell in the nanopore for less than 100 ms are not released upon nucleotide incorporation events. In some cases, the tags may be captured and/or guided through the nanopore by a second enzyme or protein (e.g., a nucleic acid binding protein). The second enzyme may cleave a tag upon (e.g., during or after) nucleotide incorporation. A linker between the tag and the nucleotide may be cleaved.

Figure 26:
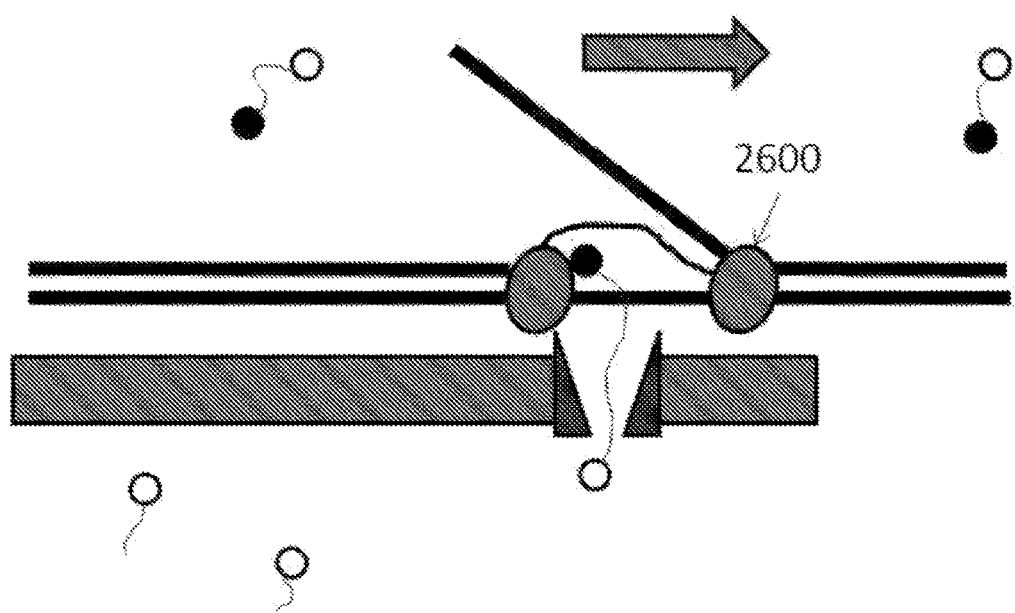
FIG. 26 shows the use of a second enzyme or protein such as a helicase or nucleic acid binding protein in addition to a polymerase.

As seen in FIG. 26, the second enzyme or protein 2600 can be attached to the polymerase. In some embodiments, the second enzyme or protein is a nucleic acid helicase that facilitates the dissociation of double stranded template to single stranded template. In some cases, the second enzyme or protein is not attached to the polymerase. The second enzyme or protein can be a nucleic acid binding protein that binds to single stranded nucleic acid template to help keep the template single stranded. The nucleic acid binding proteins can slide along the single stranded nucleic acid molecule.

Incorporated nucleotides may be differentiated from unincorporated nucleotides based on the length of time in which a tag associated with a nucleotide is detected with the aid of the nanopore. In some examples, a tag associated with a nucleotide that has been incorporated into a nucleic acid strand ("incorporated nucleotide") is detected by, or with the aid of, the nanopore for an average time period of at least about 5 milliseconds (ms), 10 ms, 20 ms, 30 ms, 40 ms, 50 ms, 60 ms, 70 ms, 80 ms, 90 ms, 100 ms, 200 ms, 300 ms, 400 ms, or 500 ms. A tag associated with an unincorporated (e.g., free-flowing) nucleotide is detected by the nanopore for a time period on average less than about 500 ms, 400 ms, 300 ms, 200 ms, 100 ms, 90 ms, 80 ms, 70 ms, 60 ms, 50 ms, 40 ms, 30 ms, 20 ms, 10 ms, 5 ms, or 1 ms. In some situations, a tag associated with an incorporated nucleotide is detected by the nanopore for a time period of on average at least about 100 ms, and a tag associated with an unincorporated nucleotide is detected by the nanopore for a time period that is on average less than 100 ms.

In some examples, a tag that is coupled to an incorporated nucleotide is distinguished from a tag associated with a nucleotide that has not been incorporated into a growing complementary strand based on the residence time of the tag in the nanopore or a signal detected from the unincorporated nucleotide with the aid of the nanopore. An unincorporated nucleotide may generate a signal (e.g., voltage difference, current) that is detectable for a time period between about 1 nanosecond (ns) and 100 ms, or between about 1 ns and 50 ms, whereas an incorporated nucleotide may generate a signal with a lifetime between about 50 ms and 500 ms, or 100 ms and 200 ms. In some examples, an unincorporated nucleotide may generate a signal that is detectable for a time period between about 1 ns and 10 ms, or 1 ns and 1 ms. In some cases, an unincorporated tag is detectable by a nanopore for a time period (average) that is longer than the time period in which an incorporated tag is detectable by the nanopore.

In some cases, incorporated nucleotides are detected by and/or are detectable by the nanopore for a shorter period of time than an un-incorporated nucleotide. The difference and/or ratio between these times can be used to determine whether a nucleotide detected by the nanopore is incorporated or not, as described herein.

The detection period can be based on the free-flow of the nucleotide through the nanopore; an unincorporated nucleotide may dwell at or in proximity to the nanopore for a time period between about 1 nanosecond (ns) and 100 ms, or between about 1 ns and 50 ms, whereas an incorporated nucleotide may dwell at or in proximity to the nanopore for a time between about 50 ms and 500 ms, or 100 ms and 200 ms. The time periods can vary based on processing conditions; however, an incorporated nucleotide may have a dwell time that is greater than that of an unincorporated nucleotide.

Polymerization (e.g., incorporation) and detection can both proceed without interference with each other. In some embodiments, the polymerization of a first tagged nucleotide does not appreciably interfere with nanopore detection of a tag associated with a second tagged nucleotide. In some embodiments, nanopore detection of a tag associated with a first tagged nucleotide does not interfere with the polymerization of a second tagged nucleotide. In some cases, the tag is sufficiently long to be detected by the nanopore and/or to be detected without preventing nucleotide incorporation events.

A tag (or tag species) can include a detectable atom or molecule, or a plurality of detectable atoms or molecules. In some cases, a tag includes a one or more adenine, guanine, cytosine, thymine, uracil, or a derivative thereof linked to any position including a phosphate group, sugar or a nitrogenous base of a nucleic acid molecule. In some examples, a tag includes one or more adenine, guanine, cytosine, thymine, uracil, or a derivative thereof covalently linked to a phosphate group of a nucleic acid base.

A tag can have a length of at least about 0.1 nanometers (nm), 1 nm, 2 nm, 3 nm, 4, nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, or 1000 nm.

A tag may include a tail of repeating subunits, such as a plurality of adenine, guanine, cytosine, thymine, uracil, or a derivative thereof. For example, a tag can include a tail portion having at least 2, 3, 4, 5, 6, 7, 8, 9, 10, 20, 30, 40, 50, 60, 70, 80, 90, 100, 1000, 10,000, or 100,000 subunits of adenine, guanine, cytosine, thymine, uracil, or a derivative thereof. The subunits can be linked to one another, and at a terminal end linked to a phosphate group of the nucleic acid. Other examples of tag portions include any polymeric material, such as polyethylene glycol (PEG), polysulfonates, amino acids, or any completely or partially positively charged, negatively charged, or un-charged polymer.

A tag species can have an electronic signature that is unique to the type of nucleic acid molecule being incorporated during incorporation. For example, a nucleic acid base that is adenine, guanine, cytosine, thymine, or uracil may have a tag species that has one or more species that are unique to adenine, guanine, cytosine, thymine, or uracil, respectively.

Figure 6:
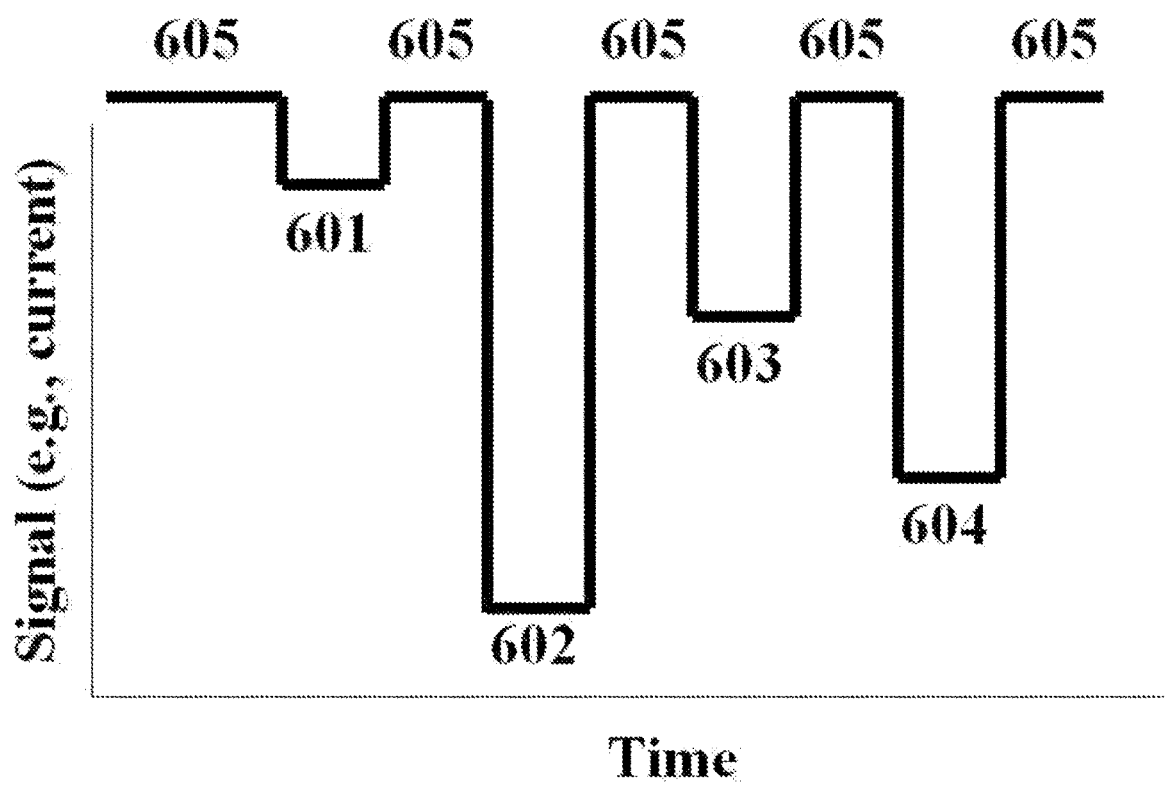
FIG. 6 shows an example of a signal generated by tags dwelling briefly in a nanopore.

FIG. 6 shows an example of different signals being generated by different tags as they are detected by the nanopore. Four different signal intensities (601, 602, 603 and 604) are detected. These may correspond to four different tags. For example, the tag presented to the nanopore and/or released by incorporation of adenosine (A) may generate a signal with an amplitude 601. A tag presented to the nanopore and/or released by incorporation of cytosine (C) may generate a signal with a higher amplitude 603; a tag presented to the nanopore and/or released by incorporation of guanine (C) may generate a signal with an even higher amplitude 604; and a tag presented to the nanopore and/or released by incorporation of thymine (T) may generate a signal with a yet higher amplitude 602. FIG. 6 also shows an example of the detection of tag molecules that have been released from the nucleotide and/or are presented to the nanopore upon nucleotide incorporation events. The methods described herein may be able to distinguish between a tag inserted into a nanopore and subsequently cleaved (see, e.g., FIG. 4, D) and a free-floating, non-cleaved tag (see, e.g., FIG. 4, F).

Methods provided herein may be capable of distinguishing between a released (or cleaved) tag and a non-released (or uncleaved) tag with an accuracy of at least about 50%, at least about 60%, at least about 70%, at least about 80%, at least about 85%, at least about 90%, at least about 95%, at least about 99%, at least about 99.5%, at least about 99.9%, at least about 99.95% or at least about 99.99%, or at least about 99.999%, or at least about 99.9999%.

With reference to FIG. 6, the magnitude of the current can be reduced by any suitable amount by the tag, including about 5%, about 10%, about 15%, about 20%, about 25%, about 30%, about 40%, about 50%, about 60%, about 70%, about 80%, about 90%, about 95%, or about 99%. In some embodiments, the magnitude of the current is reduced by at least 5%, at least 10%, at least 15%, at least 20%, at least 25%, at least 30%, at least 40%, at least 50%, at least 60%, at least 70%, at least 80%, at least 90%, at least 95%, or at least 99%. In some embodiments, the magnitude of the current is reduced by at most 5%, at most 10%, at most 15%, at most 20%, at most 25%, at most 30%, at most 40%, at most 50%, at most 60%, at most 70%, at most 80%, at most 90%, at most 95%, or at most 99%.

The method can further comprise detecting, periods of time between incorporation of the individual tagged nucleotides (e.g., periods 605 in FIG. 6). The periods of time between incorporation of the individual tagged nucleotides can have a high magnitude of current. In some embodiments, the magnitude of current flowing through the nanopore between nucleotide incorporation events is (e.g., returns to) about 50%, about 60%, about 70%, about 80%, about 90%, about 95%, or about 99% of the maximum current (e.g., when no tag is present). In some embodiments, the magnitude of current flowing through the nanopore between nucleotide incorporation events is at least 50%, at least 60%, at least 70%, at least 80%, at least 90%, at least 95%, or at least 99% of the maximum current. Detecting and/or observing the current during periods of time between incorporation of the individual tagged nucleotides can improve sequencing accuracy in some instances (e.g., when sequencing repeating stretches of a nucleic acid such as 3 or more of the same base in a row). The periods between nucleotide incorporation events can be used as a clock signal that gives the length of the nucleic acid molecule or segment thereof being sequenced.

Methods described herein may be able to distinguish between an incorporated (e.g., polymerized) tagged nucleotide and a non-polymerized tag nucleotide (e.g., 506 and 505 in FIG. 5). In some examples, an incorporated tagged nucleotide can be distinguished from a non-incorporated tag nucleotide with an accuracy of at least about 50%, at least about 60%, at least about 70%, at least about 80%, at least about 85%, at least about 90%, at least about 95%, at least about 99%, at least about 99.5%, at least about 99.9%, at least about 99.95% or at least about 99.99%, or at least about 99.999%, or at least about 99.9999%.

Associations Between Tags and Nanopores

In an aspect, the method and devices described herein distinguishes between tagged nucleotides that are incorporated into a nucleic acid molecule and non-incorporated tagged nucleotides based in part upon the amount of time (or ratio of times) that the tag is associated with and/or detectable by the nanopore. In some instances, the interaction between the nucleotide and the polymerase increases the amount of time that the tag is associated with and/or detectable by the nanopore. In some cases, the tag interacts with and/or associates with the nanopore.

The tag can be relatively easier to insert into the nanopore than to remove from the nanopore. In some instances, the tag enters the nanopore more rapidly and/or with less force compared to the tag exiting the nanopore. Once associated with the nanopore, the tag can pass through the nanopore more rapidly and/or with less force compared to the tag exiting the nanopore from the direction in which it entered the nanopore.

The association between the tag and the nanopore can be any suitable force or interaction, such as a non-covalent bond, a covalent bond that may be reversible, electrostatic or electrodynamic forces, or any combination thereof. In some cases, the tag is designed to interact with the nanopore, the nanopore is mutated or designed to interact with the tag, or both the tag and nanopore are designed or selected to form an association with each other.

The association between the tag and the nanopore can be any suitable strength. In some cases, the association is sufficiently strong such that the electrodes can be re-charged without ejecting the tag from the nanopore. The voltage polarity across the nanopore can be reversed to re-charge the electrode and reversed again to detect the tag without the tag leaving the nanopore in some instances.

Figure 19:
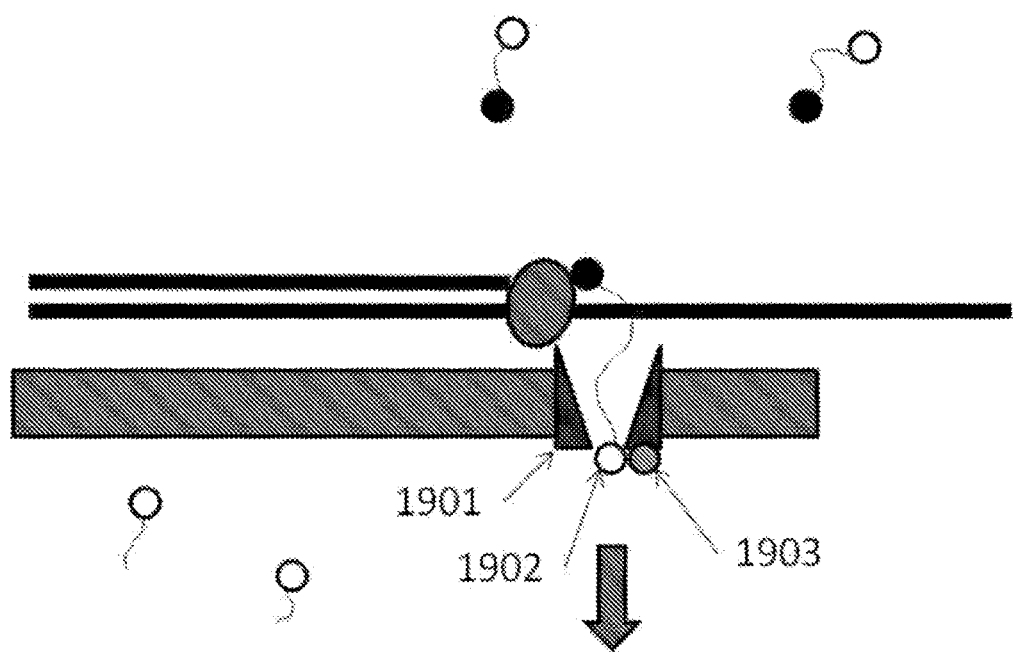
FIG. 19 shows a tag associating with a binding partner on the side of the nanopore nearer the detection circuitry.

FIG. 19 shows an example in which a tag portion of a tagged nucleotide 1902 binds to and/or interacts with an affinity partner (e.g., affinity molecule) or binding partner 1903 on the side of the nanopore 1901 opposite the polymerase. The affinity molecule or binding partner 1903 can be separate from the nanopore 1901 but linked to the nanopore or, as an alternative, can be part of the nanopore 1901. The binding partner can be attached to any suitable surface such as the nanopore or the membrane. In some examples, any suitable combination of tag molecule and binding partner can be used. In some instances, the tag molecule and binding partner comprise nucleic acid molecules that hybridize to each other. In some instances, the tag molecule and binding partner comprise streptavidin and biotin that bind to each other. As an alternative, the binding partner 1903 can be part of the nanopore 1901.

Figure 20:
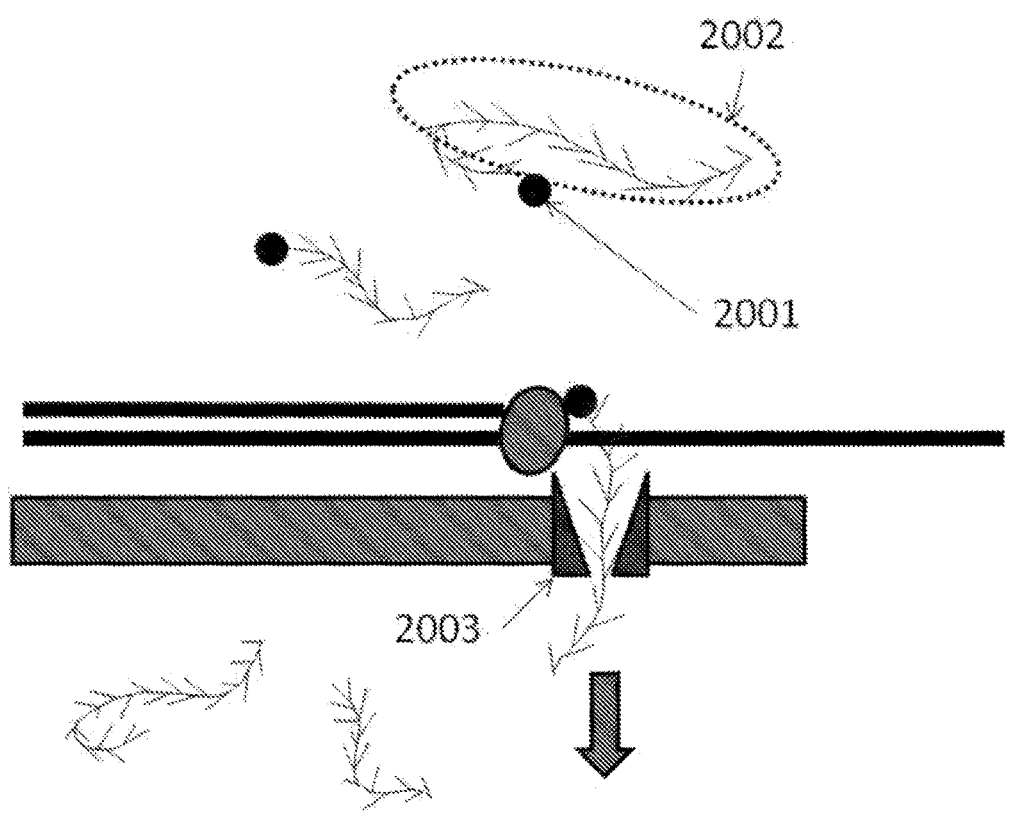
FIG. 20 shows a barbed tag that flows through the nanopore more easily than flowing out of the nanopore.

FIG. 20 shows an example in which the tagged nucleotide comprises a nucleotide portion 2001 and a tag portion 2002 where the tag portion is barbed. The tag portion is shaped (e.g., barbed) in such a way that the tag flows through the nanopore 2003 easier (e.g., more rapidly and/or with less force) than back out of the nanopore in the direction in which it entered the nanopore. In one embodiment, the tag portion comprises a single stranded nucleic acid and the bases (e.g., A, C, T, G) are connected to the backbone of the nucleic acid tag at an angle that points toward the nucleotide portion 2001 of the tagged nucleotide (i.e., is barbed). As an alternative, the nanopore can include a flap or other obstruction that permits the flow of a tag portion along a first direction (e.g., out of the nanopore) and prevents the flow of the tag portion along a second direction (e.g., a direction opposite to the second direction). The flap may be any hinged obstruction.

The tag may be designed or selected (e.g., using directed evolution) to bind and/or associate with the nanopore (e.g., in the pore portion of the nanopore). In some embodiments, the tag is a peptide having an arrangement of hydrophilic, hydrophobic, positively charged, and negatively charged amino acid residues that bind to the nanopore. In some embodiments, the tag is a nucleic acid having an arrangement of bases that bind to the nanopore.

The nanopore may be mutated to associate with the tag molecule. For example, the nanopore can be designed or selected (e.g., using directed evolution) to have an arrangement of hydrophilic, hydrophobic, positively charged, and negatively charged amino acid residues that bind to the tag molecule. The amino acid residues can be in the vestibule and/or pore of the nanopore.

Expelling of Tags from a Nanopore

This disclosure provides methods in which a tag molecule is expelled from a nanopore. For instance, a chip can be adapted to expel a tag molecule in cases where the tag resides in the nanopore or is presented to the nanopore upon nucleotide incorporation events, such as, for example, during sequencing. The tag may be expelled in the opposite direction from which it entered the nanopore (e.g., without the tag passing through the nanopore)—e.g., the tag may be directed into the nanopore from a first opening and be expelled from the nanopore from a second opening that is different than the first opening. Alternatively, the tag may be expelled from the opening in which it entered the nanopore—e.g., the tag may be directed into the nanopore from a first opening and be expelled from the nanopore from the first opening.

An aspect of the invention provides a chip for sequencing a nucleic acid sample, the chip comprising a plurality of individually addressable nanopores, an individually addressable nanopore of the plurality having at least one nanopore formed in a membrane disposed adjacent to an integrated circuit, each individually addressable nanopore adapted to expel a tag molecule from the nanopore. In some embodiments, the chip is adapted to expel (or the method expels) the tag in the direction from which the tag entered the nanopore. In some cases, the nanopore expels the tag molecule with a voltage pulse or a series of voltage pulses. A voltage pulse may have a duration of about 1 nanosecond to 1 minute, or 10 nanoseconds to 1 second.

The nanopore may be adapted to expel (or the method expels) the tag molecule within a period of time such that two tag molecules are not present in the nanopore at the same time. The probability of two molecules being present in the nanopore at the same time is at most 1%, at most 0.5%, at most 0.1%, at most 0.05% or at most 0.01% in some embodiments.

In some instances, the nanopore is adapted to expel the tag molecule within (in a time period less than) about 0.1 ms, 0.5 ms, 1 ms, 5 ms, 10 ms or 50 ms of when the tag entered the nanopore.

A tag can be expelled from a nanopore using an electrical potential (or voltage). The voltage can, in some cases, be of a polarity that is opposite from that used to draw the tag into the nanopore. The voltage can be applied with the aid of an alternating current (AC) waveform having a cycle of at least about 1 nanosecond, 10 nanoseconds, 100 nanoseconds, 500 nanoseconds, 1 microsecond, 100 microseconds, 1 millisecond (ms), 5 ms, 10 ms, 20 ms, 30 ms, 40 ms, 50 ms, 100 ms, 200 ms, 300 ms, 400 ms, 500 ms, 600 ms, 700 ms, 800 ms, 900 ms, 1 second, 2 seconds, 3 seconds, 4 seconds, 5 seconds, 6 seconds, 7 seconds, 8 seconds, 9 seconds, 10 seconds, 100 seconds, 200 seconds, 300 seconds, 400 seconds, 500 seconds, or 1000 seconds.

Alternating Current (AC) Waveforms

Sequencing a nucleic acid molecule by passing the nucleic acid strand through a nanopore can require applying a direct current (e.g., so that the direction at which the molecule moves through the nanopore is not reversed). However, operating a nanopore sensor for long periods of time using a direct current can change the composition of the electrode, unbalance the ion concentrations across the nanopore and have other undesirable effects. Applying an alternating current (AC) waveform can avoid these undesirable effects and have certain advantages as described below. The nucleic acid sequencing methods described herein that utilized tagged nucleotides are fully compatible with AC applied voltages and can therefore be used to achieve said advantages.

The ability to re-charge the electrode during the detection cycle can be advantageous when using sacrificial electrodes or electrodes that change molecular character in the current-carrying reactions (e.g., electrodes comprising silver), or electrodes that change molecular character in current-carrying reactions. An electrode may deplete during a detection cycle, though in some cases the electrode may not deplete during the detection cycle. The re-charge can prevent the electrode from reaching a given depletion limit, such as becoming fully depleted, which can be a problem when the electrodes are small (e.g., when the electrodes are small enough to provide an array of electrodes having at least 500 electrodes per square millimeter). Electrode lifetime in some cases scales and is at least partly dependent on the width of the electrode.

In some instances, the electrode is porous and/or "spongy". A porous electrode can have an enhanced capacitance of the double layer to the bulk liquid compared to a non-porous electrode. The porous electrode can be formed by electroplating a metal (e.g., a noble metal) onto a surface in the presence of detergent. The metal that is electroplated can be any suitable metal. The metal can be a noble metal (e.g., palladium, silver, osmium, iridium, platinum, silver, or gold). In some cases the surface is a metal surface (e.g., palladium, silver, osmium, iridium, platinum, silver, or gold). In some cases, the surface is about 5 microns in diameter and smooth. The detergent can create nanometer-scale interstitial spaces in the surface, making it porous or "spongy". Another method to produce a porous and/or spongy electrode is to deposit metal oxide (e.g., platinum oxide) and expose it to a reducing agent (e.g., 4% $H_2$). The reducing agent can reduce the metal oxide (e.g., platinum oxide) back to metal (e.g., platinum), and in doing so provide a spongy and/or porous electrode. The (e.g., palladium) sponge can soak up electrolyte and create a large effective surface area (e.g., 33 pico-farads per square micron of the electrode top-down area). Increasing the surface area of the electrode by making it porous as described herein can create an electrode having a capacitance that does not become fully depleted.

In some instances, the need to maintain a voltage difference of conserved polarity across the nanopore during detection for long periods of time (e.g., when sequencing a nucleic acid by passing the nucleic acid through the nanopore) depletes the electrodes and can limit the duration of detection and/or size of the electrodes. The devices and methods described herein allow for longer (e.g., infinite) detection times and/or electrodes that can be scaled down to an arbitrarily small size (e.g., as limited by considerations other than electrode depletion during detection). As described herein, the tag may be detected for only a portion of the time that it is associated with the polymerase. Switching the polarity and/or magnitude of the voltage across the nanopore (e.g., applying an AC waveform) in between detection periods allows for re-charging the electrodes. In some cases, the tag is detected a plurality of times (e.g., 2, 3, 4, 5, 6, 7, 8, 9, 10, 20, 30, 40, 50, 100, 1000, 10,000, 100,000, 1,000,000 or more times in a 100 millisecond period).

In some instances, the polarity of the voltage across the nanopore is reversed periodically. The polarity of the voltage can be reversed after detection periods lasting any suitable amount of time (e.g., about 1 ms, about 5 ms, about 10 ms, about 15 ms, about 20 ms, about 25 ms, about 30 ms, about 40 ms, about 50 ms, about 60 ms, about 80 ms, about 100 ms, about 125 ms, about 150 ms, about 200 ms, and the like). The period of time and strength of the electrical field during periods of recharging the electrodes (i.e., when the polarity of the voltage is opposite that of the voltage for tag detection) is such that the electrode is restored to its state prior to detection (e.g., mass of electrode). The net voltage across the nanopore is zero in some instances (e.g., periods of positive voltage cancel periods of negative voltage over a suitably long time scale such as 1 second, 1 minute or 5 minutes). In some cases, the voltage applied to a nanopore is balanced such that there is net zero current detected by a sensing electrode adjacent to or in proximity to the nanopore.

In some examples, an alternating current (AC) waveform is applied to a nanopore in a membrane or an electrode adjacent to the membrane to draw a tag through or in proximity to the nanopore and to release the tag. The AC waveform can have a frequency on the order of at least 10 microseconds, 1 millisecond (ms), 5 ms, 10 ms, 20 ms, 100 ms, 200 ms, 300 ms, 400 ms, 500 ms. The waveform may aid in alternately and sequentially capturing the tag and releasing the tag, or otherwise moving the tag in multiple directions (e.g., opposing directions), which may increase the overall time period in which the tag is associated with the nanopore. This balancing of charging and discharging can permit the generation of a longer signal from a nanopore electrode and/or a given tag.

In some examples, an AC waveform is applied to repeatedly direct at least a portion of a tag associated with a tagged nucleotide (e.g., incorporated tagged nucleotide) into a nanopore and direct at least a portion of the tag out of the nanopore. The tag or nucleotide coupled to the tag may be held by an enzyme (e.g., polymerase). This repetitive loading and expulsion of a single tag held by the enzyme may advantageously provide more opportunities to detect the tag. For instance, if the tag is held by the enzyme for 40 milliseconds (ms) and the AC waveform is applied high for 5 ms (to direct the tag into the nanopore) and applied low for 5 ms (to direct the tag out of the nanopore), the nanopore may be used to read the tag approximately 4 times. Multiple reads may enable correction for errors, such as errors associated with tags threading into and/or out of a nanopore.

Figure 21:
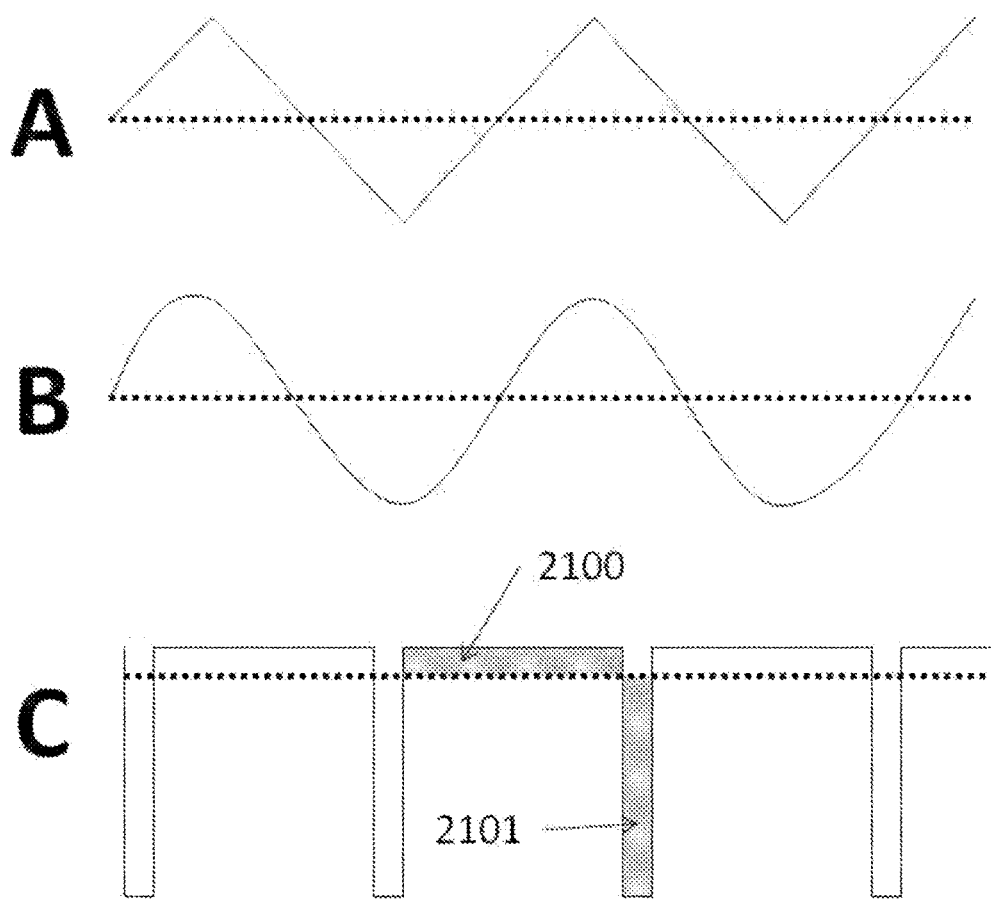
FIG. 21 shows examples of waveforms.

The waveform can have any suitable shape including either regular shapes (e.g., that repeat over a period of time) and irregular shapes (e.g., that do not repeat over any suitably long period of time such as 1 hour, 1 day or 1 week). FIG. 21 shows some suitable (regular) waveforms. Examples of waveforms include triangular waves, (panel A) sine waves (panel B), sawtooth waves, square waves, and the like.

Reversal of the polarity (i.e., positive to negative or negative to positive) of the voltage across the nanopore, such as upon the application of an alternating current (AC)

waveform, can be performed for any reason, including, but not limited to (a) recharging the electrode (e.g., changing the chemical composition of the metal electrode), (b) rebalancing the ion concentrations on the cis and trans side of the membrane, (c) re-establishing a non-zero applied voltage across the nanopore and/or (d) altering the double layer capacitance (e.g., re-setting the voltage or charge that exists at the metal electrode and analyte interface to a desired level, e.g., zero).

FIG. 21C shows a horizontal dashed line at zero potential difference across the nanopore with positive voltage extending upward in proportion to magnitude and negative voltage extending downward in proportion to magnitude. No matter the shape of the waveform, the "duty cycle" compares the combined area under the curve of a voltage versus time plot in the positive direction 2100 with the combined area under the curve in the negative direction 2101. In some cases, the positive area 2100 is equal to the negative area 2101 (i.e., the net duty cycle is zero), however the AC waveform can have any duty cycle. In some instances, judicial use of an AC waveform having an optimized duty cycle can be used to achieve any one or more of (a) the electrode is electrochemically balanced (e.g., neither charged nor depleted), (b) the ion concentration between the cis and trans side of the membrane is balanced, (c) the voltage applied across the nanopore is known (e.g., because the capacitive double layer on the electrode is periodically re-set and the capacitor discharges to the same extent with each flip in polarity), (d) the tag molecule is identified in the nanopore a plurality of times (e.g., by expelling and re-capturing the tag with each flip of polarity), (e) additional information is captured from each reading of the tag molecule (e.g., because the measured current can be a different function of applied voltage for each tag molecule), (f) a high density of nanopore sensors is achieved (e.g., because the metal electrode composition is not changing, one is not constrained by the amount of metal comprising the electrode), and/or (g) a low power consumption of the chip is achieved. These benefits can allow for continuous extended operation of the device (e.g., at least 1 hour, at least 1 day, at least 1 week).

In some situations, upon the application of a positive potential across a nanopore, a first current is measured, and upon the application of a negative potential (e.g., of equal absolute magnitude to the positive potential) across the nanopore, a second current is measured. The first current may be equal to the second current, though in some cases the first current and the second current may be different. For example, the first current may be less than the second current. In some instances, only one of a positive current and a negative current is measured.

In some cases, the nanopore detects tagged nucleotides for relatively long periods of time at a relatively low magnitude voltage (e.g., FIG. 21, indication 2100) and re-charges the electrode for relatively short periods of time at a relatively large magnitude voltage (e.g., FIG. 21, indication 2101). In some cases, the time period for detection is at least 2, at least 3, at least 4, at least 5, at least 6, at least 8, at least 10, at least 15, at least 20, or at least 50 times longer than the time period for electrode recharge.

In some instances, the waveform is altered in response to an input. In some cases, the input is the level of depletion of the electrode. In some cases, the polarity and/or magnitude of the voltage is varied at least in part based on the depletion of the electrode or depletion of current carrying ions and the waveform is irregular.

The ability to repeatedly detect and re-charge the electrodes over short time periods (e.g., over periods less than about 5 seconds, less than about 1 second, less than about 500 ms, less than about 100 ms, less than about 50 ms, less than about 10 ms, or less than about 1 ms) allows for the use of smaller electrodes relative to electrodes that may maintain a constant direct current (DC) potential and DC current and are used to sequence polynucleotides that are threaded through the nanopore. Smaller electrodes can allow for a high number of detection sites (e.g., comprising an electrode, a sensing circuit, a nanopore and a polymerase) on a surface.

The surface comprises any suitable density of discrete sites (e.g., a density suitable for sequencing a nucleic acid sample in a given amount of time or for a given cost). In an embodiment, the surface has a density of discrete sites greater than or equal to about 500 sites per 1 $mm^2$. In some embodiments, the surface has a density of discrete sites of about 100, about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 sites per 1 $mm^2$. In some embodiments, the surface has a density of discrete sites of at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 20000, at least about 40000, at least about 60000, at least about 80000, at least about 100000, or at least about 500000 sites per 1 $mm^2$.

The electrode can be re-charged prior to, between or during, or after nucleotide incorporation events. In some cases, the electrode is re-charged in about 20 milliseconds (ms), about 40 ms, about 60 ms, about 80 ms, about 100 ms, about 120 ms, about 140 ms, about 160 ms, about 180 ms, or about 200 ms. In some cases, the electrode is re-charged in less than about 20 milliseconds (ms), less than about 40 ms, less than about 60 ms, less than about 80 ms, less than about 100 ms, less than about 120 ms, less than about 140 ms, less than about 160 ms, less than about 180 ms, about 200 ms, less than about 500 ms, or less than about 1 second.

Chips Able to Distinguish Between Cleaved and Un-Cleaved Tags

Another aspect provides chips for sequencing a nucleic acid sample. In an example, a chip comprises a plurality of individually addressable nanopores. An individually addressable nanopore of the plurality can have at least one nanopore formed in a membrane disposed adjacent to an integrated circuit. Each individually addressable nanopore can be adapted to determine whether a tag molecule is bound to a nucleotide or not bound to a nucleotide or to read the change between different tags.

In some cases, a chip can comprise a plurality of individually addressable nanopores. An individually addressable nanopore of the plurality can have at least one nanopore formed in a membrane disposed adjacent to an integrated circuit. Each individually addressable nanopore can be adapted to determine whether a tag molecule is bound to an incorporated (e.g., polymerized) nucleotide or a non-incorporated nucleotide.

The chips described herein may be able to distinguish between a released tag and a non-released tag (e.g., D versus F in FIG. 4). In some embodiments, the chip is capable of distinguishing between a released tag and a non-released tag with an accuracy of at least about 80%, at least about 85%, at least about 90%, at least about 95%, at least about 97%, at least about 99%, at least about 99.5%, at least about 99.9%, at least about 99.95% or at least about 99.99%. The level of accuracy can be achieved when detecting groups of about 5, 4, 3, or 2 consecutive nucleotides. In some cases, the accuracy is achieved for single base resolution (i.e., 1 consecutive nucleotide).

The chips described herein may be able to distinguish between an incorporated tagged nucleotide and a non-incorporated tag nucleotide (e.g., 506 and 505 in FIG. 5). In some embodiments, the chip is capable of distinguishing between an incorporated tagged nucleotide and a non-incorporated tag nucleotide with an accuracy of at least about 80%, at least about 85%, at least about 90%, at least about 95%, at least about 97%, at least about 99%, at least about 99.5%, at least about 99.9%, at least about 99.95% or at least about 99.99%. The level of accuracy can be achieved when detecting groups of about 5, 4, 3, or 2 consecutive nucleotides. In some cases, the accuracy is achieved for single base resolution (i.e., 1 consecutive nucleotide).

The nanopore may aid in determining whether a tag molecule is bound to a nucleotide or not bound to a nucleotide based at least in part on differences in an electrical signal. In some cases, the nanopore may aid in determining whether a tag molecule is bound to a nucleotide or not bound to a nucleotide based at least in part on dwell time in the nanopore. The nanopore may aid in determining whether a tag molecule is bound or not bound to a nucleotide based at least in part on the fall-out voltage, which is the voltage at which the tag or tagged nucleotide exits the nanopore.

Chips Able to Capture a High Proportion of Cleaved Tags

Another aspect provides chips for sequencing a nucleic acid sample. In an example, a chip comprises a plurality of individually addressable nanopores. An individually addressable nanopore of the plurality can include at least one nanopore formed in a membrane disposed adjacent to an integrated circuit. Each individually addressable nanopore can be adapted to capture most of the tag molecules released upon incorporation (e.g., polymerization) of tagged nucleotides.

The chip can be configured to capture any suitably high percentage of tags (e.g., so as to determine the nucleic acid sequence with a suitably high accuracy). In some embodiments, the chip captures at least 90%, at least 99%, at least 99.9% or at least 99.99% of the tag molecules.

In some embodiments, the nanopore captures a plurality of different tag molecules (e.g., four distinct tag molecules released upon incorporation of the four nucleotides) at a single current level. The chip can be adapted to capture tag molecules in the same sequence in which the tag molecules are released.

Device Setup

Figure 8:
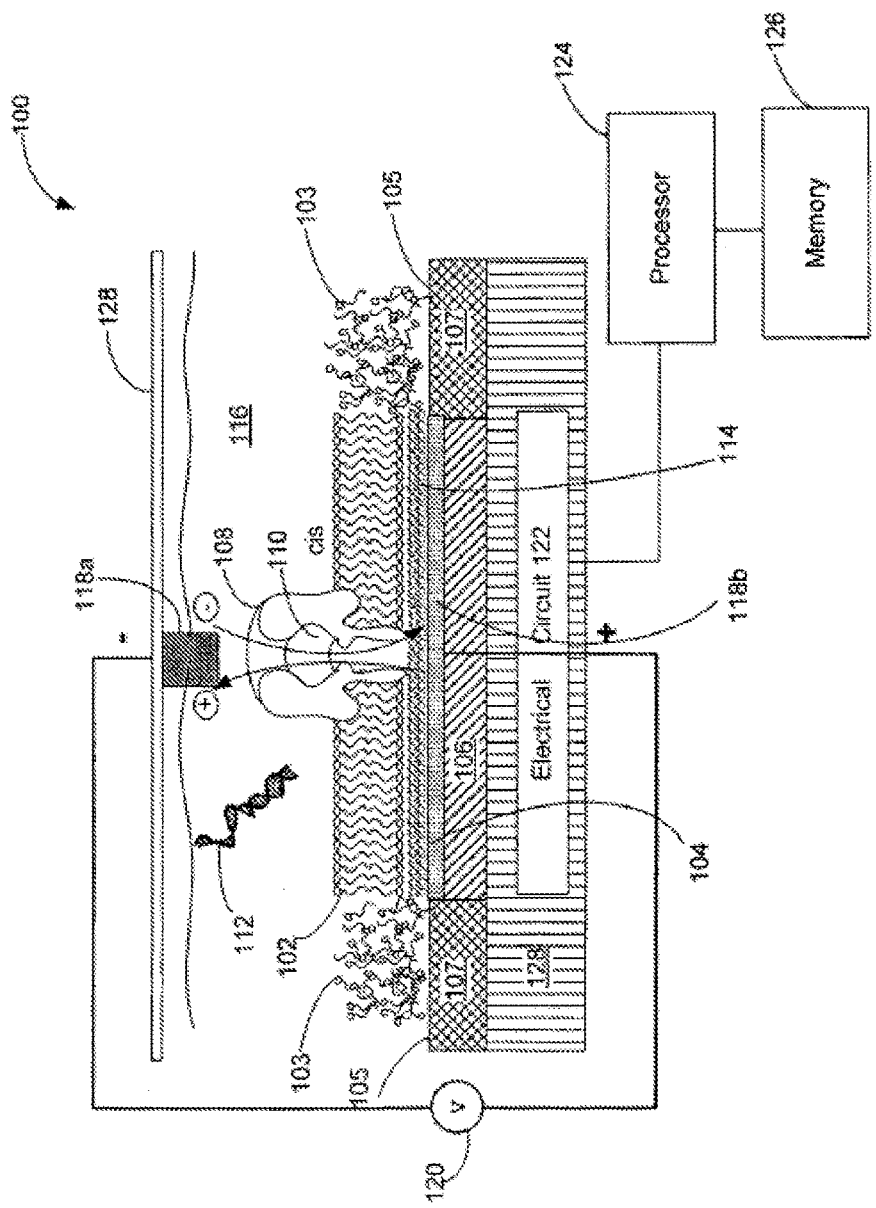
FIG. 8 shows an example of a chip set-up comprising a nanopore and not a well.

FIG. 8 schematically illustrates a nanopore device 100 (or sensor) that may be used to sequence a nucleic acid and/or detect a tag molecule as described herein. The nanopore containing lipid bilayer may be characterized by a resistance and capacitance. The nanopore device 100 includes a lipid bilayer 102 formed on a lipid bilayer compatible surface 104 of a conductive solid substrate 106, where the lipid bilayer compatible surface 104 may be isolated by lipid bilayer incompatible surfaces 105 and the conductive solid substrate 106 may be electrically isolated by insulating materials 107, and where the lipid bilayer 102 may be surrounded by amorphous lipid 103 formed on the lipid bilayer incompatible surface 105. The lipid bilayer 102 may be embedded with a single nanopore structure 108 having a nanopore 110 large enough for passing of the tag molecules being characterized and/or small ions (e.g., $Na^+$, $K^-$, $Ca^{2+}$, $Cl^{-"}$) between the two sides of the lipid bilayer 102. A layer of water molecules 114 may be adsorbed on the lipid bilayer compatible surface 104 and sandwiched between the lipid bilayer 102 and the lipid bilayer compatible surface 104. The aqueous film 114 adsorbed on the hydrophilic lipid bilayer compatible surface 104 may promote the ordering of lipid molecules and facilitate the formation of lipid bilayer on the lipid bilayer compatible surface 104. A sample chamber 116 containing a solution of the nucleic acid molecule 112 and tagged nucleotides may be provided over the lipid bilayer 102. The solution may be an aqueous solution containing electrolytes and buffered to an optimum ion concentration and maintained at an optimum pH to keep the nanopore 110 open. The device includes a pair of electrodes 118 (including a negative node 118a and a positive node 118b) coupled to a variable voltage source 120 for providing electrical stimulus (e.g., voltage bias) across the lipid bilayer and for sensing electrical characteristics of the lipid bilayer (e.g., resistance, capacitance, and ionic current flow). The surface of the positive electrode 118b is or forms a part of the lipid bilayer compatible surface 104. The conductive solid substrate 106 may be coupled to or forms a part of one of the electrodes 118. The device 100 may also include an electrical circuit 122 for controlling electrical stimulation and for processing the signal detected. In some embodiments, the variable voltage source 120 is included as a part of the electrical circuit 122. The electrical circuitry 122 may include amplifier, integrator, noise filter, feedback control logic, and/or various other components. The electrical circuitry 122 may be integrated electrical circuitry integrated within a silicon substrate 128 and may be further coupled to a computer processor 124 coupled to a memory 126.

The lipid bilayer compatible surface 104 may be formed from various materials that are suitable for ion transduction and gas formation to facilitate lipid bilayer formation. In some embodiments, conductive or semi-conductive hydrophilic materials may be used because they may allow better detection of a change in the lipid bilayer electrical characteristics. Example materials include Ag—AgCl, Au, Pt, or doped silicon or other semiconductor materials. In some cases, the electrode is not a sacrificial electrode.

The lipid bilayer incompatible surface 105 may be formed from various materials that are not suitable for lipid bilayer formation and they are typically hydrophobic. In some embodiments, non-conductive hydrophobic materials are preferred, since it electrically insulates the lipid bilayer regions in addition to separate the lipid bilayer regions from each other. Example lipid bilayer incompatible materials include for example silicon nitride (e.g., $Si_3N_4$) and Teflon, silicon oxide (e.g., $SiO_2$) silanized with hydrophobic molecules.

In an example, the nanopore device 100 of FIG. 8 is a alpha hemolysin (aHL) nanopore device having a single alpha hemolysin (aHL) protein 108 embedded in a diphytanoylphosphatidylcholine (DPhPC) lipid bilayer 102 formed over a lipid bilayer compatible silver (Ag) surface 104 coated on an aluminum material 106. The lipid bilayer compatible Ag surface 104 is isolated by lipid bilayer incompatible silicon nitride surfaces 105, and the aluminum material 106 is electrically insulated by silicon nitride materials 107. The aluminum 106 is coupled to electrical circuitry 122 that is integrated in a silicon substrate 128. A silver-silver chloride electrode placed on-chip or extending down from a cover plate 128 contacts an aqueous solution containing nucleic acid molecules.

The aHL nanopore is an assembly of seven individual peptides. The entrance or vestibule of the aHL nanopore is approximately 26 Angstroms in diameter, which is wide enough to accommodate a portion of a dsDNA molecule. From the vestible, the aHL nanopore first widens and then narrows to a barrel having a diameter of approximately 15 Angstroms, which is wide enough to allow a single ssDNA molecule (or smaller tag molecules) to pass through but not wide enough to allow a dsDNA molecule (or larger tag molecules) to pass through.

In addition to DPhPC, the lipid bilayer of the nanopore device may be assembled from various other suitable amphiphilic materials, selected based on various considerations, such as the type of nanopore used, the type of molecule being characterized, and various physical, chemical and/or electrical characteristics of the lipid bilayer formed, such as stability and permeability, resistance, and capacitance of the lipid bilayer formed. Example amphiphilic materials include various phospholipids such as palmitoyl-oleoyl-phosphatidyl-choline (POPC) and dioleoyl-phosphatidyl-methyl ester (DOPME), diphytanoylphosphatidylcholine (DPhPC), 1,2-di-O-phytanyl-sn-glycero-3-phosphocholine (DoPhPC), dipalmitoylphosphatidylcholine (DPPC), phosphatidylcholine, phosphatidylethanolamine, phosphatidylserine, phosphatidic acid, phosphatidylinositol, phosphatidylglycerol, and sphingomyelin.

In addition to the aHL nanopore shown above, the nanopore may be of various other types of nanopores. Examples include γ-hemolysin, leukocidin, melittin, *Mycobacterium smegmatis* porin A (MspA) and various other naturally occurring, modified natural, and synthetic nanopores. A suitable nanopore may be selected based on various characteristics of the analyte molecule such as the size of the analyte molecule in relation to the pore size of the nanopore. For example, the aHL nanopore that has a restrictive pore size of approximately 15 Angstroms.

Current Measurement

In some cases, current may be measured at different applied voltages. In order to accomplish this, a desired potential may be applied to the electrode, and the applied potential may be subsequently maintained throughout the measurement. In an implementation, an opamp integrator topology may be used for this purpose as described below. The integrator maintains the voltage potential at the electrode by means of capacitive feedback. The integrator circuit may provide outstanding linearity, cell-to-cell matching, and offset characteristics. The opamp integrator typically requires a large size in order to achieve the required performance. A more compact integrator topology is described below.

In some cases, a voltage potential "Vliquid" may be applied to the chamber which provides a common electrical potential (e.g., 350 mV) for all of the cells on the chip. The integrator circuit may initialize the electrode (which is electrically the top plate of the integrating capacitor) to a potential greater than the common liquid potential. For example, biasing at 450 mV may give a positive 100 mV potential between electrode and liquid. This positive voltage potential may cause a current to flow from the electrode to the liquid chamber contact. In this instance, the carriers are: (a) K+ ions which flow through the pore from the electrode (trans) side of the bi-layer to the liquid reservoir (cis) side of the bi-layer and (b) chlorine (Cl−) ions on the trans side which reacts with the silver electrode according to the following electro-chemical reaction: $Ag+Cl^- \rightarrow AgCl+e^-$.

In some cases, K+ flows out of the enclosed cell (from trans to cis side of bi-layer) while Cl− is converted to silver chloride. The electrode side of the bilayer may become desalinated as a result of the current flow. In some cases, a silver/silver-chloride liquid spongy material or matrix may serve as a reservoir to supply Cl− ions in the reverse reaction which occur at the electrical chamber contact to complete the circuit.

In some cases, electrons ultimately flow onto the top side of the integrating capacitor which creates the electrical current that is measured. The electrochemical reaction converts silver to silver chloride and current will continue to flow only as long as there is available silver to be converted. The limited supply of silver leads to a current dependent electrode life in some cases. In some embodiments, electrode materials that are not depleted (e.g., platinum) are used.

The tag can modulate an ionic current flowing through a nanopore when a constant electrical potential is applied to the nanopore detector, allowing a record of the current to determine the identity of the tag. However, a constant electrical potential may not adequately distinguish between different tags (e.g., tags associated with A, C, T or G). In an aspect, the applied voltage can be varied (e.g., swept over a range of voltages) to identify the tag (e.g., with a confidence of at least 90%, at least 95%, at least 99%, at least 99.9%, or at least 99.99%).

The applied voltage can be varied in any suitable manner including according to any of the waveforms shown in FIG. 21. The voltage can be varied over any suitable range including from about 120 mV to about 150 mV, from about 40 mV to about 150 mV.

Figure 22:
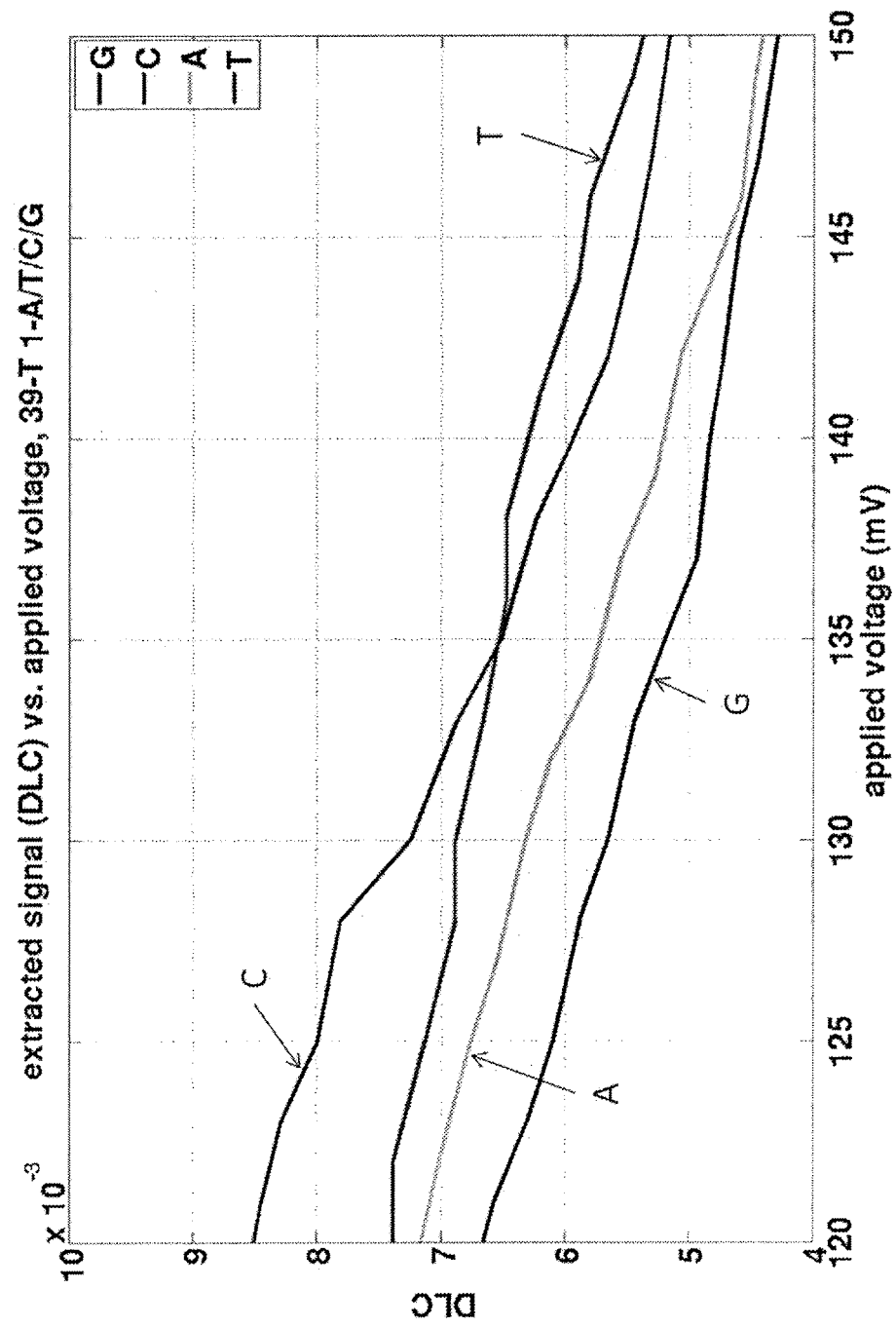
FIG. 22 shows a plot of extracted signal versus applied voltage for the four nucleic acid bases adenine (A), cytosine (C), guanine (G) and thymine (T)
Figure 23:
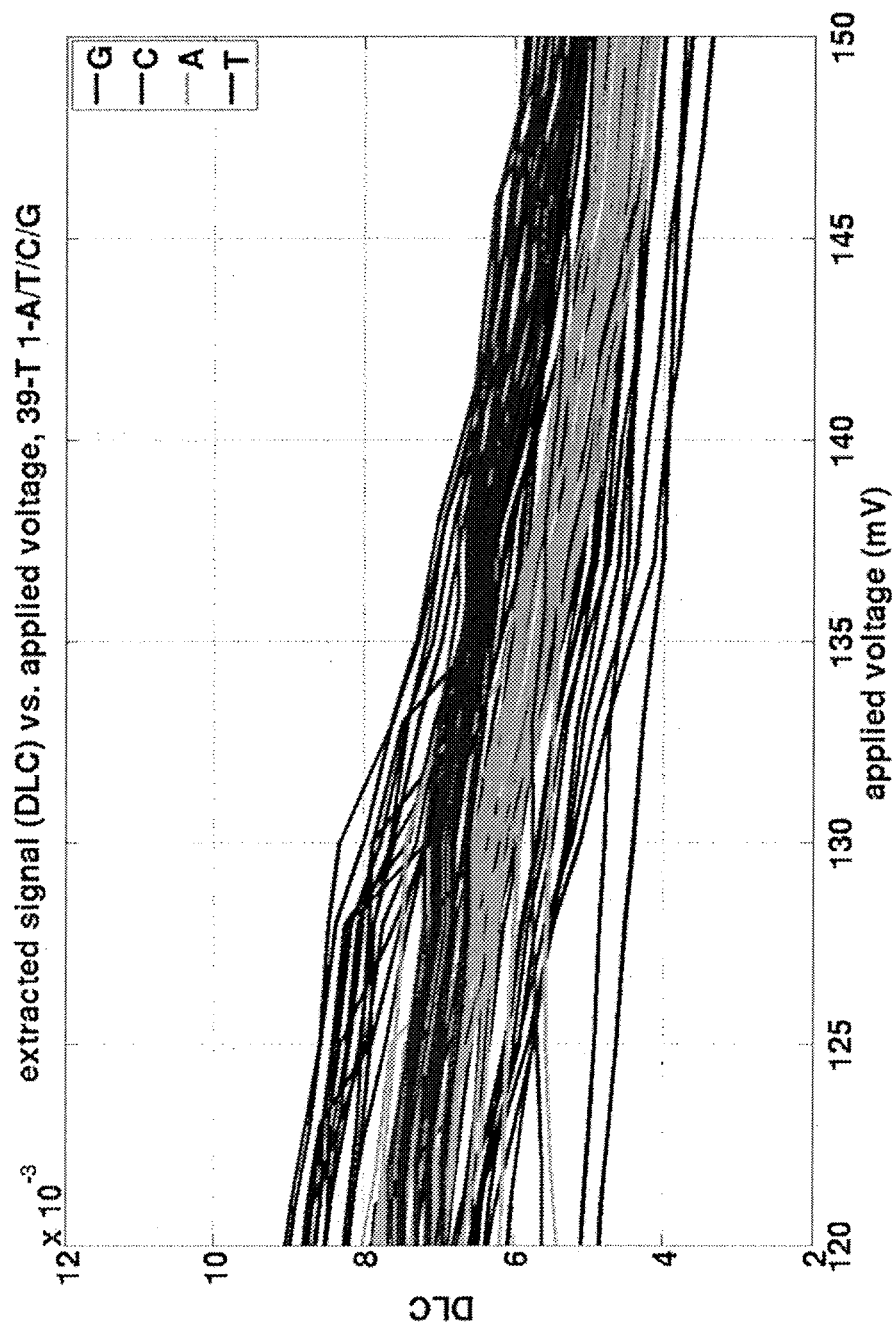
FIG. 23 shows a plot of extracted signal versus applied voltage for multiple runs of the four nucleic acid bases adenine (A), cytosine (C), guanine (G) and thymine (T)

FIG. 22 shows the extracted signal (e.g., differential log conductance (DLC)) versus applied voltage for the nucleotides adenine (A, green), cytosine (C, blue), guanine (G, black) and thymine (T, red). FIG. 23 shows the same information for a plurality of nucleotides (many experimental trials). As seen here, cytosine is relatively easy to distinguish from thymine at 120 mV, but difficult to distinguish from each other at 150 mV (e.g., because the extracted signal is approximately equal for C and T at 150 mV). Also, thymine is difficult to distinguish from adenine at 120 mV, but relatively easier to distinguish at 150 mV. Therefore, in an embodiment, the applied voltage can be varied from 120 mV to 150 mV to distinguish each of the nucleotides A, C, G and T.

Figure 24:
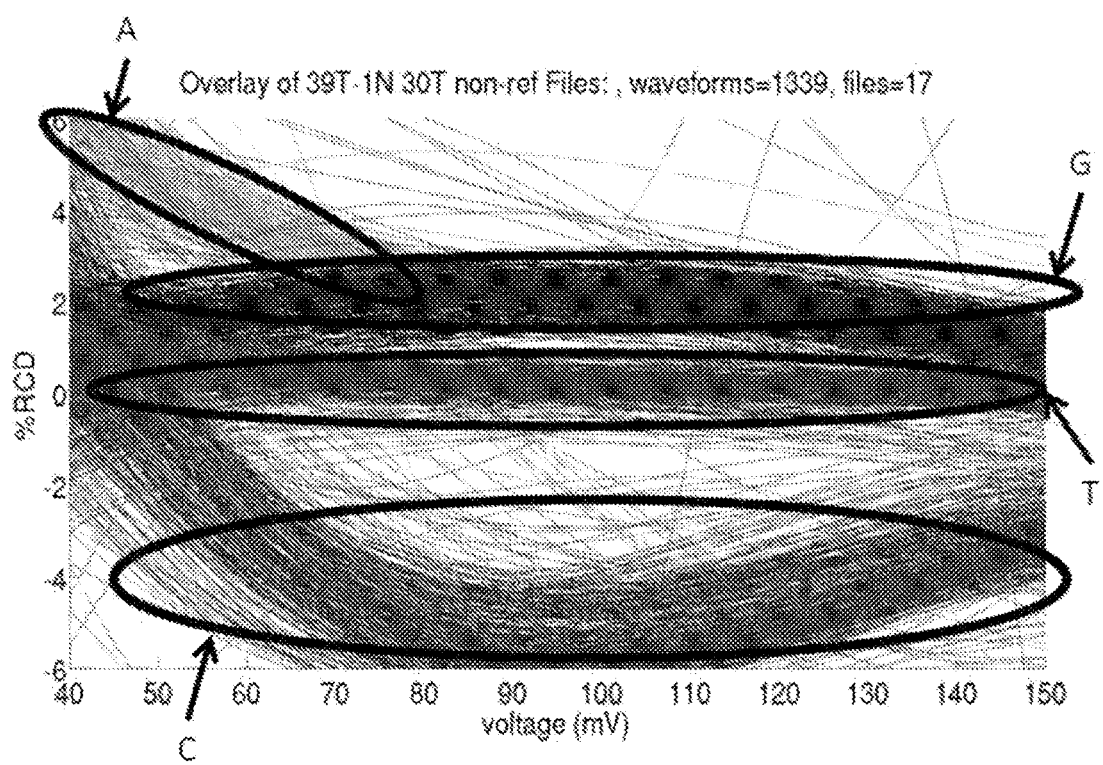
FIG. 24 shows a plot of percent reference conductive difference (% RCD) versus applied voltage for multiple runs of the four nucleic acid bases adenine (A), cytosine (C), guanine (G) and thymine (T)

FIG. 24 shows the percent reference conductive difference (% RCD) as a function of applied voltage for the nucleotides adenine (A, green), cytosine (C, blue), guanine (G, black) and thymine (T, red). Plotting % RCD (which is essentially the difference in conductance of each molecule referenced to a 30T reference molecule) can remove off set and gain variation between experiments. FIG. 24 includes individual DNA waveforms from the first block of 17/20 Trials. The % RCD of all single nucleotide DNA captures from number 50 to 200 for all 17 good Trials. Voltages where each of the nucleotides are distinguishable are indicated.

While FIGS. 22-24 show the response to varied applied voltage for nucleotides, the concept of varied applied voltage can be used to distinguish tag molecules (e.g., attached to tagged nucleotides).

Cell Circuitry

Figure 12:
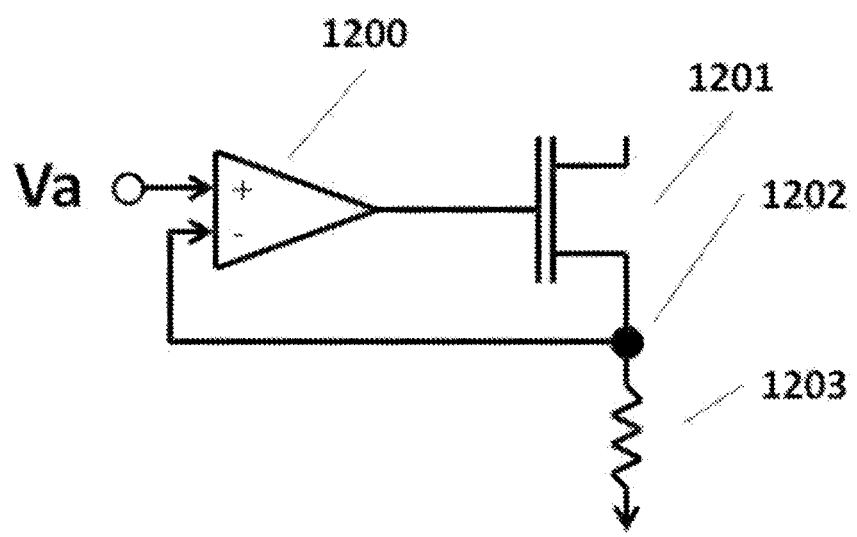
FIG. 12 shows an example of an ultra compact measurement circuit.

An example of cell circuitry is shown in FIG. 12. An applied voltage Va is applied to an opamp 1200 ahead of a MOSFET current conveyor gate 1201. Also shown here are an electrode 1202 and the resistance of the nucleic acid and/or tag detected by the device 1203.

An applied voltage Va can drive the current conveyor gate 1201. The resulting voltage on the electrodes is then Va–Vt where Vt is the threshold voltage of the MOSFET. In some instances, this results in limited control of the actual voltage applied to the electrode as a MOSFET threshold voltage can vary considerably over process, voltage, temperature, and even between devices within a chip. This Vt variation can be greater at low current levels where sub-threshold leakage effects can come into play. Therefore, in order to provide better control of the applied voltage, an opamp can be used in a follower feedback configuration with the current conveyor device. This ensures that the voltage applied to the electrode is Va, independent of variation of the MOSFET threshold voltage.

Figure 10:
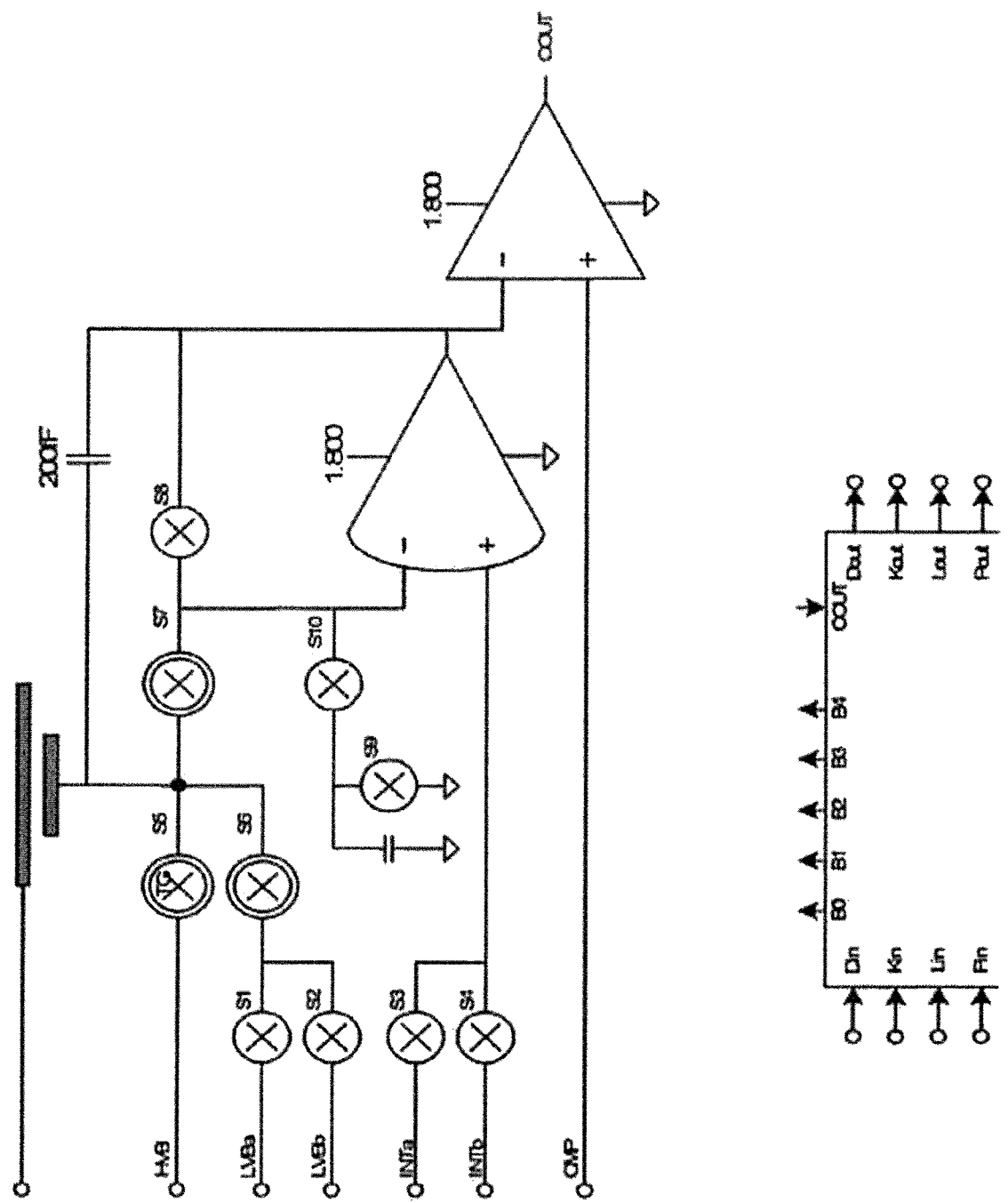
FIG. 10 shows an example of cell analog circuitry.

Another example of cell circuitry is shown in FIG. 10 and includes an integrator, comparator, and digital logic to shift in control bits and simultaneously shift out the state of the comparator output. The cell circuitry may be adapted for use with systems and methods provided herein. The B0 through B1 lines may come out of the shift register. The analog signals are shared by all cells within a bank while digital lines may be daisy-chained from cell to cell.

The cell digital logics comprises the 5 bit data shift register (DSR), 5 bit parallel load registers (PLR), control logic, and analog integrator circuit. Using the LIN signal, the control data shifted into the DSR is parallel loaded into the PLR. These 5 bits control digital "break-before-make" timing logic which controls the switches in the cell. In addition the digital logic has a set-reset (SR) latch to record the switching of the comparator output.

The architecture delivers a variable sample rate that is proportional to the individual cell current. A higher current may result in more samples per second than a lower current. The resolution of the current measurement is related to the current being measured. A small current may be measured with finer resolution than a large current, which may be a benefit over fixed resolution measurement systems. There is an analog input which allows the user to adjust sample rates by changing the voltage swing of the integrator. It may be possible to increase the sample rate in order to analyze biologically fast processes or to slow the sample rate (and thereby gain precision) in order to analyze biologically slow processes.

The output of the integrator is initialized to the voltage LVB (low voltage bias) and integrates up to the voltage CMP. A sample is generated every time the integrator output swings between these two levels. Thus the greater the current the faster the integrator output swings and therefore the faster the sample rate. Similarly if CMP voltage is reduced the output swing of the integrator needed to generate a new sample is reduced and therefore the sample rate is increased. Thus simply reducing the voltage difference between LVB and CMP provides a mechanism to increase the sample rate.

A nanopore based sequencing chip may incorporate a large number of autonomously operating or individually addressable cells configured as an array. For example an array of one million cells can be constructed of 1000 rows of cells by 1000 columns of cells. This array enables the parallel sequencing of nucleic acid molecules by measuring the conductance difference when tags released upon nucleotide incorporation events are detected by the nanopore for example. Moreover this circuitry implementation allows the conductance characteristics of the pore-molecular complex to be determined which may be valuable in distinguishing between tags.

The integrated nanopore/bilayer electronic cell structures may apply appropriate voltages in order to perform current measurements. For example, it may be necessary to both (a) control electrode voltage potential and (b) monitor electrode current simultaneously in order to perform correctly.

Moreover it may be necessary to control cells independently from one another. The independent control of a cell may be required in order to manage a large number of cells that may be in different physical states. Precise control of the piecewise linear voltage waveform stimulus applied to the electrode may be used to transition between the physical states of the cell.

In order to reduce the circuit size and complexity it may be sufficient to provide logic to apply two separate voltages. This allows two independent grouping of cells and corresponding state transition stimulus to be applied. The state transitions are stochastic in nature with a relatively low probability of occurrence. Thus it may be highly useful to be able to assert the appropriate control voltage and subsequently perform a measurement to determine if the desired state transition has occurred. For example the appropriate voltage may be applied to a cell and then the current measured to determine whether a bilayer has formed. The cells are divided into two groups: (a) those which have had a bilayer form and no longer need to have the voltage applied. These cells may have a 0V bias applied in order to effect the null operation (NOP)—that is stay in the same state and (b) those which do not have a bilayer formed. These cells will again have the bilayer formation electric voltage applied.

A substantial simplification and circuit size reduction may be achieved by constraining the allowable applied voltages to two and iteratively transitioning cells in batches between the physical states. For example, a reduction by at least a factor of 1.1, 2, 3, 4, 5, 6, 7, 8, 9, 10, 20, 30, 40, 50, or 100 may be achieved by constraining the allowable applied voltages.

Figure 11:
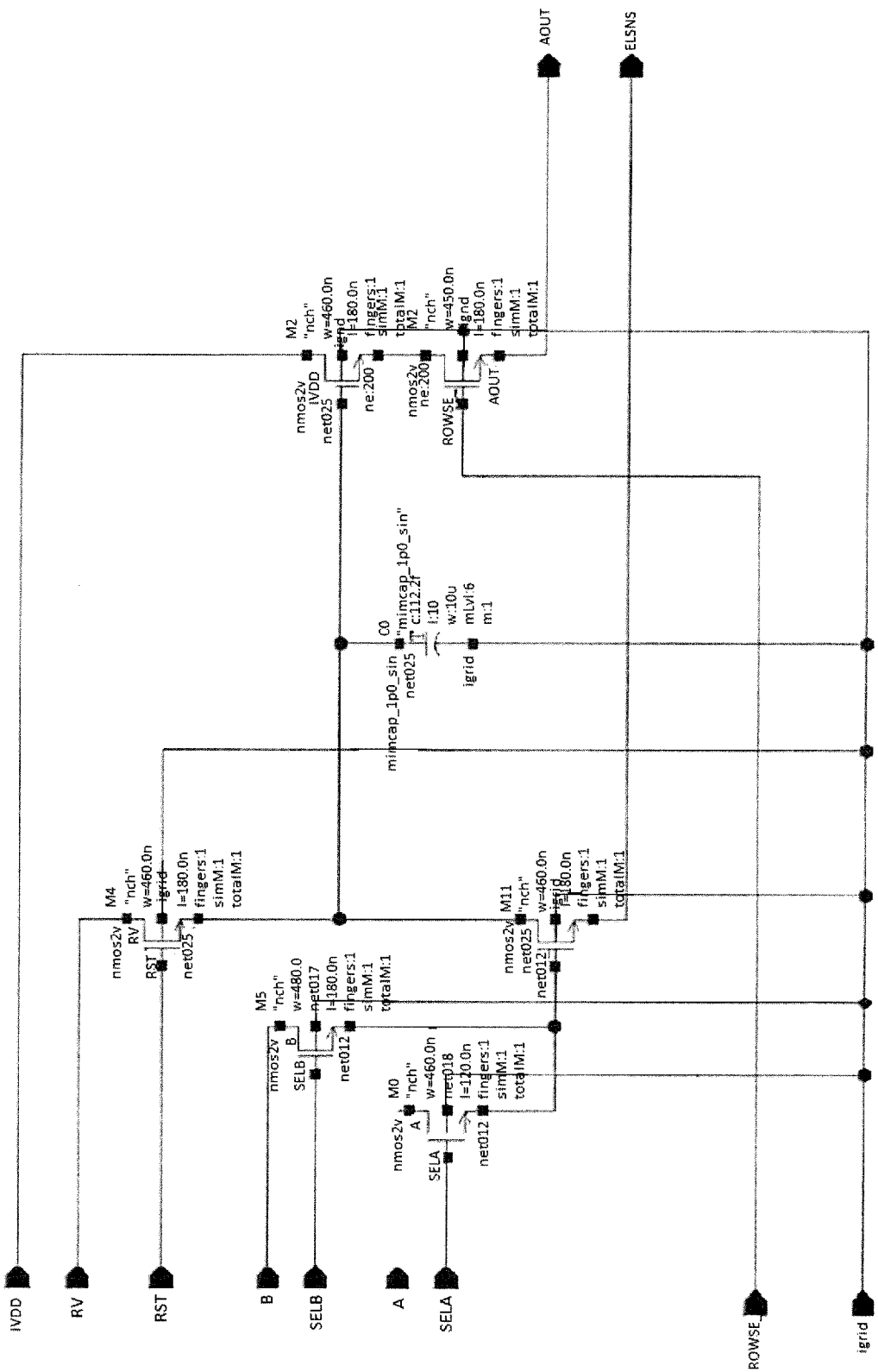
FIG. 11 shows an example of an ultra compact measurement circuit.

Yet another implementation of the invention using a compact measurement circuit is shown in FIG. 11. In some instances, the compact measurement circuit may be used to achieve the high array densities described herein. This circuit is also designed to apply a voltage to the electrode while simultaneously measuring low level currents.

The cell operates as an Ultra Compact Integrator (UCI) and the basic operation is described here. The cell is electrically connected to an electrochemically active electrode (e.g., AgCl) through the Electrod-Sense (ELSNS) connection. NMOS transistor M11 performs two independent functions: (1) operates as a source follower to apply a voltage to the ELSNS node given by (Vg1–Vt1) and (2) operates as a current conveyer to move electrons from the capacitor C1 to the ELSNS node (and vice versa).

In some instances, a controlled voltage potential may be applied to the ELSNS electrode and this may be varied simply by changing the voltage on the gate of the electrode source follower M11. Furthermore any current from M11 source pin is directly and accurately propagated to the M11 drain pin where it may accumulate on capacitor C0. Thus M11 and C0 act together as an ultra-compact integrator. This integrator may be used to determine the current sourced/sunk to/from the electrode by measuring the change in voltage integrated onto the capacitor according to the following: $I*t=C*V$, where I is current, t is time, C is capacitance and V is voltage change.

In some cases, the voltage change is measured at a fixed interval t (e.g., every 1 ms).

Transistor M2 may be configured as a source follower in order to buffer the capacitor voltage and provide a low impedance representation of the integrated voltage. This prevents charge sharing from changing the voltage on the capacitor.

Transistor M3 may be used as a row access device with the analog voltage output AOUT connected as a column shared with many other cells. Only a single row of the column connected AOUT signal is enabled so that a single cell's voltage is measured.

In an alternative implementation transistor M3 may be omitted by connecting transistor M2's drain to a row selectable "switched rail".

Transistor M4 may be used to reset the cell to a predetermined starting voltage from which the voltage is integrated. For example applying a high voltage (ex: to VDD=1.8V) to both RST and RV will pull the capacitor up to a pre-charged value of (VDD−Vt5). The exact starting value may vary both cell to cell (due to Vt variation of M4 and M2) as well as from measurement to measurement due to the reset switch thermal noise (sqrt(KTC) noise). As a result a correlated double sampling (CDS) technique is used to measure the integrator starting voltage and the ending voltage to determine the actual voltage change during the integration period.

Note also that the drain of transistor M4 may be connected to a controlled voltage RV (reset voltage). In normal operation this may be driven to VDD, however it may also be driven to a low voltage. If the "drain" of M4 is in fact driven to ground than the current flow may be reversed (i.e., current may flow from the electrode into the circuit through M1 and M4 and the notion of source and drain may be swapped). In some cases, when operating the circuit in this mode the negative voltage applied to the electrode (with respect to the liquid reference) is controlled by this RV voltage (assuming that Vg1 and Vg5 are at least a threshold greater than RV). Thus a ground voltage on RV may be used to apply a negative voltage to the electrode (for example to accomplish electro-poration or bi-layer formation).

An analog to digital converter (ADC, not shown) measures the AOUT voltage immediately after reset and again after the integration period (performs CDS measurement) in order to determine the current integrated during a fixed period of time. And ADC may be implemented per column or a separate transistor used for each column as an analog mux to share a single ADC between multiple columns. This column mux factor may be varied depending on the requirements for noise, accuracy, and throughput.

At any given time, each cell may be in one of four different physical states: (1) short-circuit to liquid (2) bi-layer formed (3) bi-layer+pore (4) bi-layer+pore+nucleic acid and/or tag molecules.

In some instances, a voltage is applied in order to move cells between states. The NOP operation is used to leave a cell in a particular desired state while other cells are stimulated with an applied potential to move from one state to another.

This may be accomplished by having two (or more) different voltages which may be applied to the gate voltage of the M1 source follower which is indirectly used to control the voltage applied to the electrode with respect to the liquid potential. Thus transistor M5 is used to apply voltage A while transistor M6 is used to apply voltage B. Thus together M5 and M6 operate as an analog mux with either SELA or SELB being driven high to select the voltage.

Since every cell may be in a possible different state and because SELA and SELB are complementary a memory element can be used in each cell to select between voltage A or B. This memory element can be a dynamic element (capacitor) that was refreshed on every cycle or a simple cheater-latch memory element (cross-coupled inverter).

Opamp Test Chip Structure

In some examples, a test chip includes an array of 264 sensors arranged in four separate groups (aka banks) of 66 sensor cells each. Each group is in turn divided into three "columns" with 22 sensors "cells" in each column. The "cell" name is apropos given that ideally a virtual cell consisting of a bi-lipid layer and inserted nanopore is formed above each of the 264 sensors in the array (although the device may operate successfully with only a fraction of the sensor cells so populated).

There is a single analog I/O pad which applies a voltage potential to the liquid contained within a conductive cylinder mounted to the surface of the die. This "liquid" potential is applied to the top side of the pore and is common to all cells in a detector array. The bottom side of the pore has an exposed electrode and each sensor cell may apply a distinct bottom side potential to its electrode. The current is then measured between the top liquid connection and each cell's electrode connection on the bottom side of the pore. The sensor cell measures the current traveling through the pore as modulated by the tag molecule passing within the pore.

Figure 9:
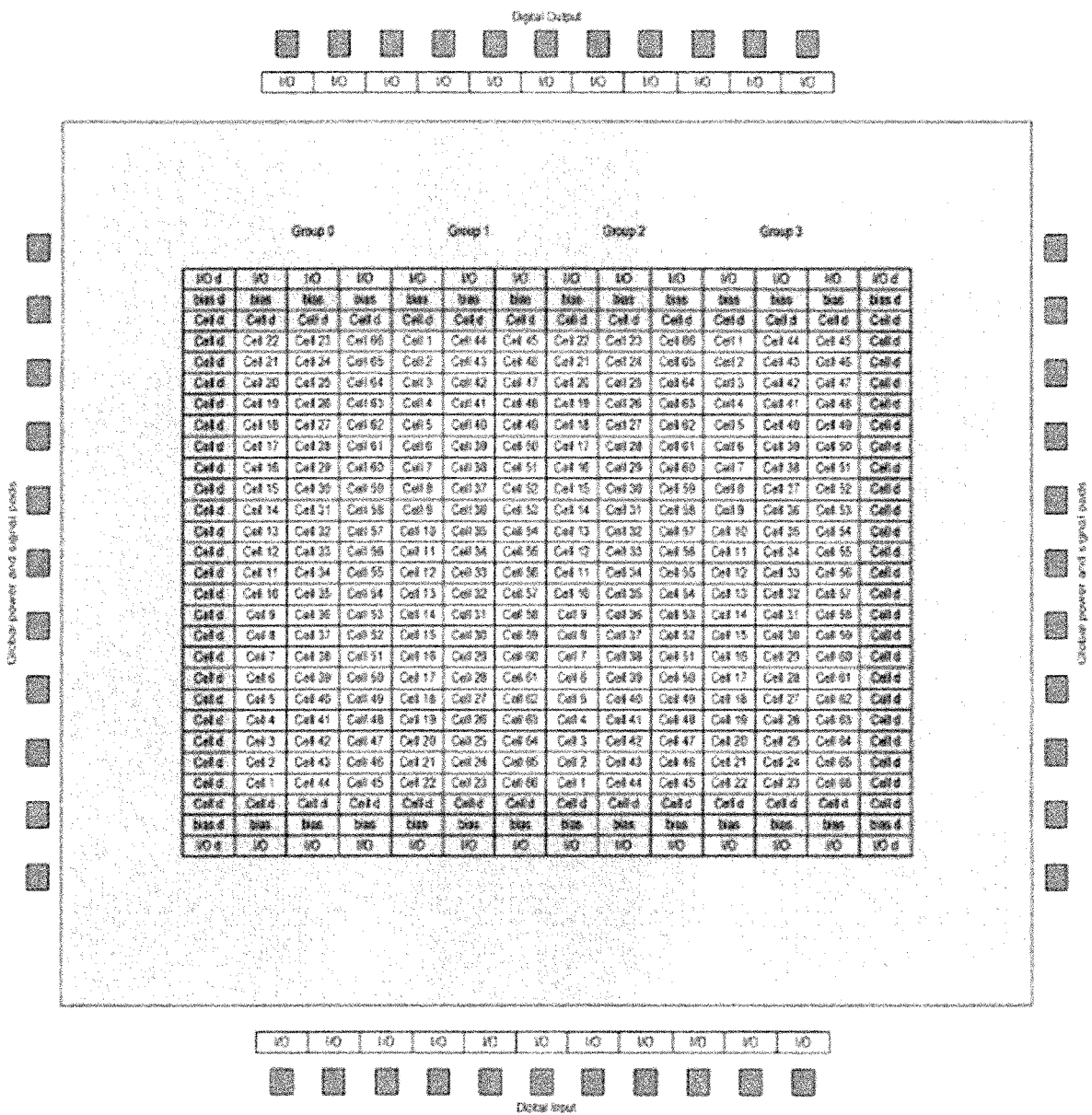
FIG. 9 shows an example of a test chip cell array configuration.

In some cases, five bits control the mode of each sensor cell. With continued reference to FIG. 9, each of the 264 cells in the array may be controlled individually. Values are applied separately to a group of 66 cells. The mode of each of the 66 cells in a group is controlled by serially shifting in 330 (66*5 bits/cell) digital values into a DataShiftRegister (DSR). These values are shifted into the array using the KIN (clock), and DIN (dat in) pins with a separate pin pair for each group of 66 cells.

Thus 330 clocks are used to shift 330 bits into the DSR shift register. A second 330 bit Parallel Load Register (PLR) is parallel loaded from this shift register when the corresponding LIN<i> (Load Input) is asserted high. At the same time as the PLR is parallel loaded the status value of the cell is loaded into the DSR.

A complete operation may consist of 330 clocks to shift in 330 data bits into the DSR, a single clock cycle with LIN signal asserted high, followed by 330 clock cycles to read the captured status data shifted out of the DSR. The operation is pipelined so that a new 330 bits may be shifted into the DSR simultaneously while the 330 bits are being read out of the array. Thus at 50 MHz clock frequency the cycle time for a read is 331/50 MHz=6.62 us.

Arrays of Nanopores for Sequencing

Figure 7:
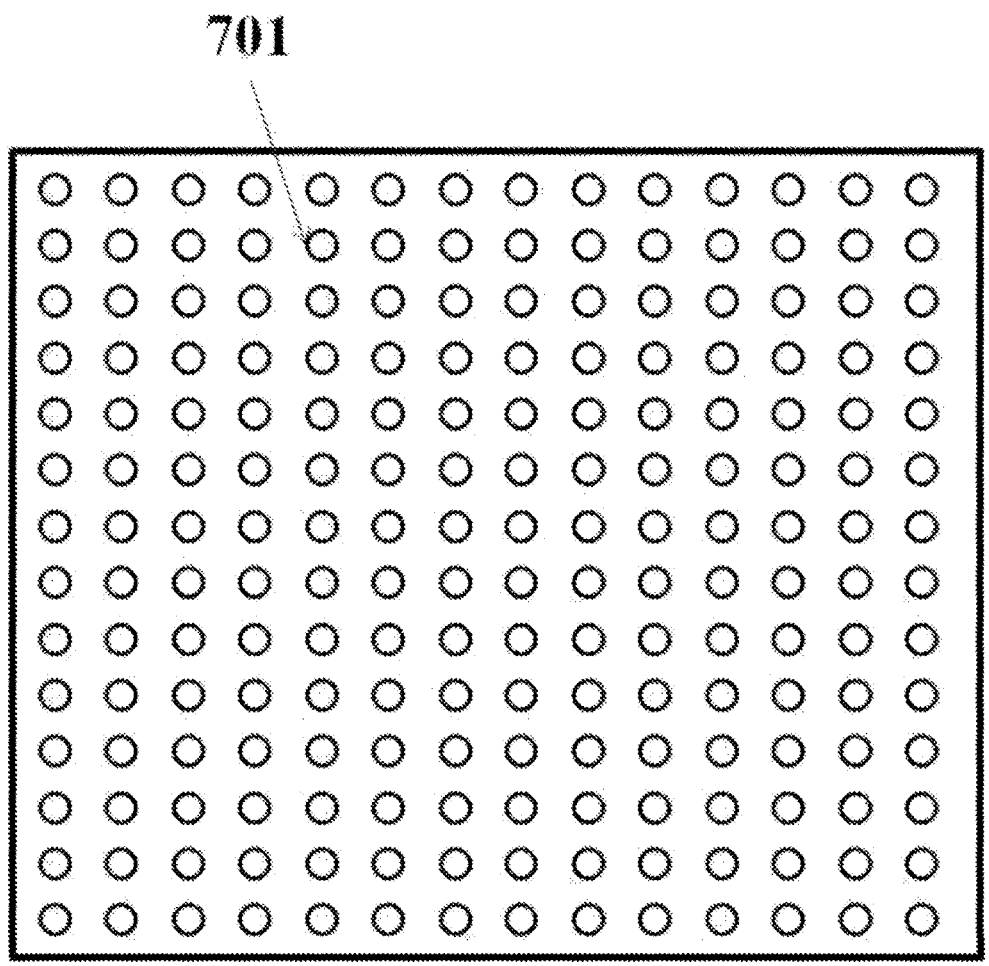
FIG. 7 shows an array of nanopore detectors.

The disclosure provides an array of nanopore detectors (or sensors) for sequencing nucleic acids. With reference to FIG. 7, a plurality of nucleic acid molecules may be sequenced on an array of nanopore detectors. Here, each nanopore location (e.g., 701) comprises a nanopore, in some cases attached to a polymerase enzyme and/or phosphatase enzymes. There is also generally a sensor at each array location as described elsewhere herein.

In some examples, an array of nanopores attached to a nucleic acid polymerase is provided, and tagged nucleotides are incorporated with the polymerase. During polymerization, a tag is detected by the nanopore (e.g., by releasing and passing into or through the nanopore, or by being presented to the nanopore). The array of nanopores may have any suitable number of nanopores. In some instances, the array comprises about 200, about 400, about 600, about 800, about 1000, about 1500, about 2000, about 3000, about 4000, about 5000, about 10000, about 15000, about 20000, about 40000, about 60000, about 80000, about 100000, about 200000, about 400000, about 600000, about 800000, about 1000000, and the like nanopores. In some instances, the array comprises at least 200, at least 400, at least 600, at least 800, at least 1000, at least 1500, at least 2000, at least 3000, at least 4000, at least 5000, at least 10000, at least 15000, at least 20000, at least 40000, at least 60000, at least 80000, at least 100000, at least 200000, at least 400000, at least 600000, at least 800000, or at least 1000000 nanopores.

In some cases, a single tag is released and/or presented upon incorporation of a single nucleotide and detected by a nanopore. In other cases, a plurality of tags are released and/or presented upon incorporation of a plurality of nucleotides. A nanopore sensor adjacent to a nanopore may detect an individual tag, or a plurality of tags. One or more signals associated with plurality of tags may be detected and processed to yield an averaged signal.

Tags may be detected by the sensor as a function of time. Tags detected with time may be used to determine the nucleic acid sequence of the nucleic acid sample, such as with the aid of a computer system (see, e.g., FIG. 16) that is programmed to record sensor data and generate sequence information from the data.

The array of nanopore detectors may have a high density of discrete sites. For example, a relatively large number of sites per unit area (i.e., density) allows for the construction of smaller devices, which are portable, low-cost, or have other advantageous features. An individual site in the array can be an individually addressable site. A large number of sites comprising a nanopore and a sensing circuit may allow for a relatively large number of nucleic acid molecules to be sequenced at once, such as, for example, through parallel sequencing. Such a system may increase the throughput and/or decrease the cost of sequencing a nucleic acid sample.

A nucleic acid sample may be sequenced using a sensor (or detector) having a substrate with a surface comprising discrete sites, each individual site having a nanopore, a polymerase and in some cases at least one phosphatase enzyme attached to the nanopore and a sensing circuit adjacent to the nanopore. The system may further comprise a flow cell in fluid communication with the substrate, the flow cell adapted to deliver one or more reagents to the substrate.

The surface comprises any suitable density of discrete sites (e.g., a density suitable for sequencing a nucleic acid sample in a given amount of time or for a given cost). Each discrete site can include a sensor. The surface may have a density of discrete sites greater than or equal to about 500 sites per 1 mm$^2$. In some embodiments, the surface has a density of discrete sites of about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 sites per 1 mm$^2$. In some cases, the surface has a density of discrete sites of at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 20000, at least 40000, at least 60000, at least 80000, at least 100000, or at least 500000 sites per 1 mm$^2$.

Tagged Nucleotides

In some cases, a tagged nucleotide comprises a tag capable of being cleaved in a nucleotide incorporation event and detected with the aid of a nanopore. The tag may be attached to the 5'-phosphate of the nucleotide. In some instances, the tag is not a fluorophore. The tag may be detectable by its charge, shape, size, or any combination thereof. Examples of tags include various polymers. Each type of nucleotide (i.e., A, C, G, T) generally comprises a unique tag.

Figure 13:
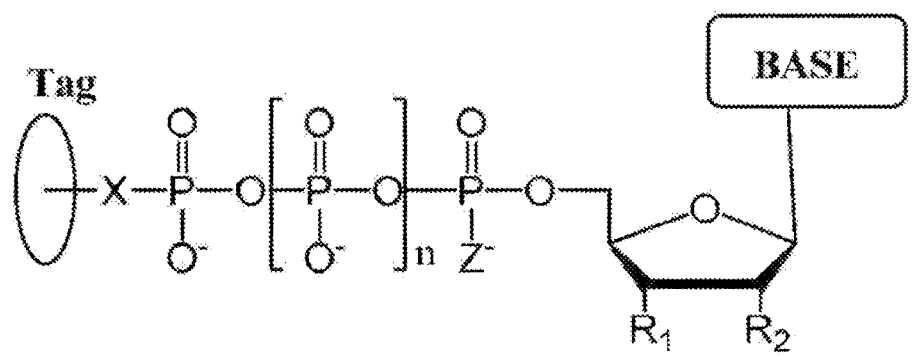
FIG. 13 shows an example of a tag molecule attached to the phosphate of a nucleotide.

Tags may be located on any suitable position on the nucleotide. FIG. 13 provides an example of a tagged nucleotide. Here, $R_1$ is generally OH and $R_2$ is H (i.e., for DNA) or OH (i.e., for RNA), although other modifications are acceptable. In FIG. 13, X is any suitable linker. In some cases, the linker is cleavable. Examples of linkers include without limitation, O, NH, S or $CH_2$. Examples of suitable chemical groups for the position Z include O, S, or $BH_3$. The base is any base suitable for incorporation into a nucleic acid including adenine, guanine, cytosine, thymine, uracil, or a derivative thereof. Universal bases are also acceptable in some cases.

The number of phosphates (n) is any suitable integer value (e.g., a number of phosphates such that the nucleotide may be incorporated into a nucleic acid molecule). In some instances, all types of tagged nucleotides have the same number of phosphates, but this is not required. In some applications, there is a different tag for each type of nucleotide and the number of phosphates is not necessarily used to distinguish the various tags. However, in some cases more than one type of nucleotide (e.g., A, C, T, G or U) have the same tag molecule and the ability to distinguish one nucleotide from another is determined at least in part by the number of phosphates (with various types of nucleotides having a different value for n). In some embodiments, the value for n is 1, 2, 3, 4, 5, 6, 7, 8, 9, 10, or greater.

Suitable tags are described below. In some instances, the tag has a charge which is reverse in sign relative to the charge on the rest of the compound. When the tag is attached, the charge on the overall compound may be neutral. Release of the tag may result in two molecules, a charged tag and a charged nucleotide. The charged tag passes through a nanopore and is detected in some cases.

Figure 14:
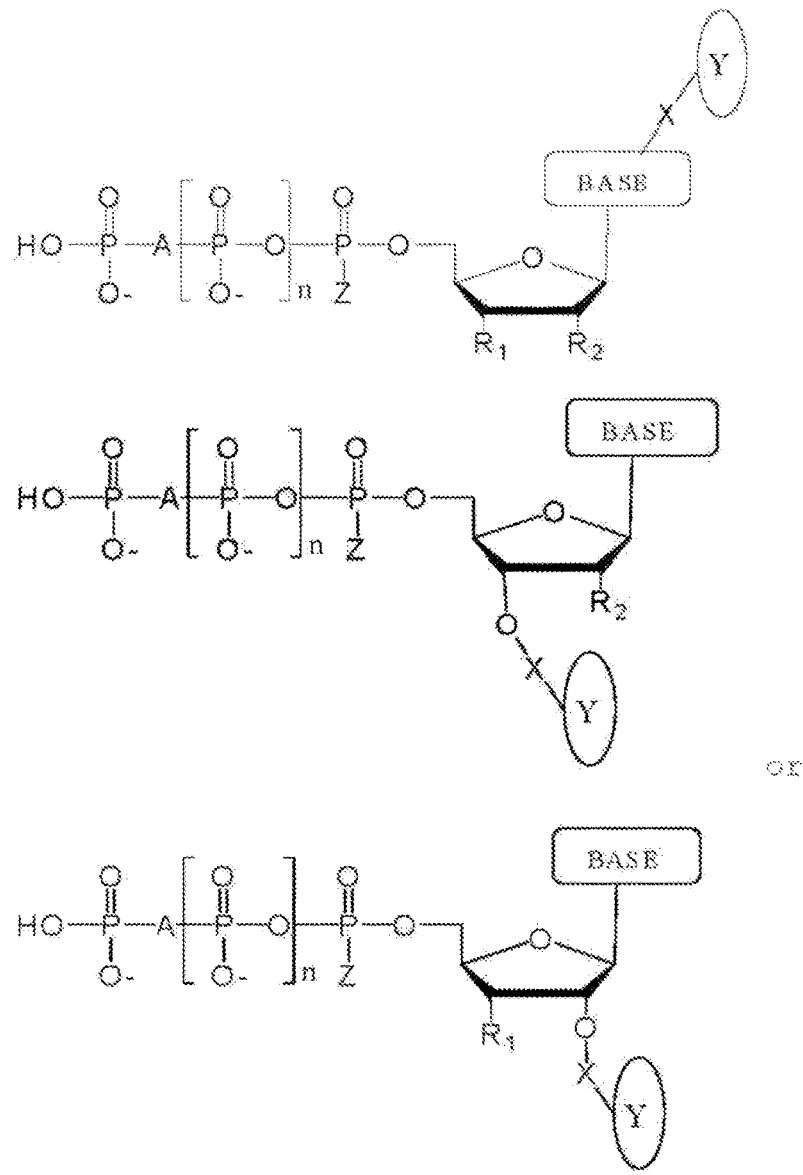
FIG. 14 shows examples of alternate tag locations.

More examples of suitable tagged nucleotides are shown in FIG. 14. The tag may be attached to the sugar molecule, the base molecule, or any combination thereof. With reference to FIG. 13, Y is a tag and X is a linker (in some cases cleavable). Furthermore, $R_1$, if present, is generally OH, —$OCH_2N_3$ or —O-2-nitrobenzyl, and $R_2$, if present, is generally H. Also, Z is generally O, S or $BH_3$, and n is any integer including 1, 2, 3, or 4. In some cases, the A is O, S, CH2, CHF, CFF, or NH.

With continued reference to FIG. 14, the type of base on each dNPP analogue is generally different from the type of base on each of the other three dNPP analogues, and the type of tag on each dNPP analogue is generally different from the type of tag on each of the other three dNPP analogues. Suitable bases include, but are not limited to adenine, guanine, cytosine, uracil or thymine, or a derivative of each thereof. In some cases, the base is one of 7-deazaguanine, 7-deazaadenine or 5-methylcytosine.

In cases where $R_1$ is —O—$CH_2N_3$, the methods can further comprise treating the incorporated dNPP analogue so as to remove the —$CH_2N_3$ and result in an OH group attached to the 3' position thereby permitting incorporation of a further dNPP analogue.

In cases where $R_1$ is —O-2-nitrobenzyl, the methods can further comprise treating the incorporated nucleotide analogue so as to remove the -2-nitrobenzyl and result in an OH group attached to the 3' position thereby permitting incorporation of a further dNPP analogue.

Examples of Tags

A tag may be any chemical group or molecule that is capable of being detected in a nanopore. In some cases, a tag comprises one or more of ethylene glycol, an amino acid, a carbohydrate, a peptide, a dye, a chemilluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof.

It is also contemplated that the tag further comprises appropriate number of lysines or arginines to balance the number of phosphates in the compound.

In some cases, the tag is a polymer. Polyethylene glycol (PEG) is an example of a polymer and has the structure as follows:

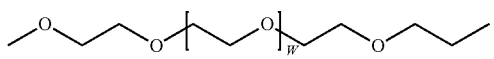

Any number of ethylene glycol units (W) may be used. In some instances, W is an integer between 0 and 100. In some cases, the number of ethylene glycol units is different for each type of nucleotide. In an embodiment, the four types of nucleotides comprise tags having 16, 20, 24 or 36 ethylene glycol units. In some cases, the tag further comprises an additional identifiable moiety, such as a coumarin based dye. In some cases, the polymer is charged. In some instances, the polymer is not charged and the tag is detected in a high concentration of salt (e.g., 3-4 M).

As used herein, the term "alkyl" includes both branched and straight-chain saturated aliphatic hydrocarbon groups having the specified number of carbon atoms and may be unsubstituted or substituted. As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom.

Figure 31:
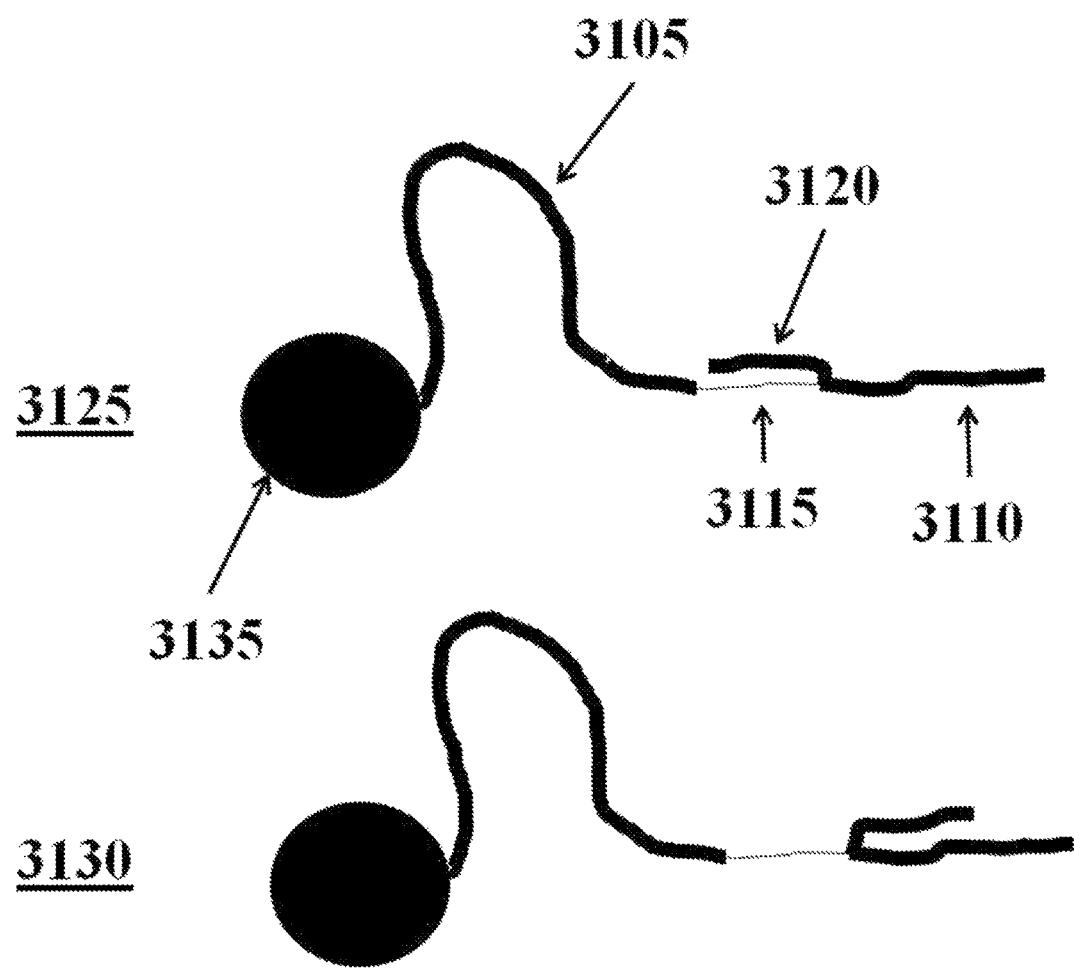
FIG. 31 shows an example of a tagged nucleotide having a gate.

In some cases, the tag is only capable of passing through the nanopore in one direction (e.g., without reversing direction). The tag can have a hinged gate attached to the tag that is thin enough to pass through the nanopore when the gate is aligned with the tag in one direction, but not in another direction. With reference to FIG. 31, the disclosure provides a tag molecule, comprising a first polymer chain 3105 comprising a first segment 3110 and a second segment 3115, where the second segment is narrower than the first segment. The second segment can have a width that is smaller than the narrowest opening of the nanopore. The tag molecule can include a second polymer chain 3120 comprising two ends, where a first end is affixed to the first polymer chain adjacent to the second segment and a second end is not affixed to the first polymer chain. The tag molecule is capable of being threaded through a nanopore in a first direction where the second polymer chain aligns adjacent to the second segment 3125. In some cases, the tag molecule is not capable of being threaded through the nanopore in a second direction where the second polymer chain does not align adjacent to the second segment 3130. The second direction can be opposite the first direction.

The first and/or second polymer chains can comprise nucleotides. In some cases, the second polymer chain base pairs with the first polymer chain when the second polymer chain does not align adjacent to the second segment. In some instances, the first polymer chain is affixed to a nucleotide 3135 (e.g., to a terminal phosphate of the nucleotide). The first polymer chain can be released from the nucleotide when the nucleotide is incorporated into a growing nucleic acid strand.

The second segment can comprise any polymer or other molecule that is thin enough to pass through a nanopore when aligned with the gate (second polymer). For instance, the second segment can comprise a-basic nucleotides (i.e., a nucleic acid chain not having any nucleic acid bases) or a carbon chain.

Figure 32:
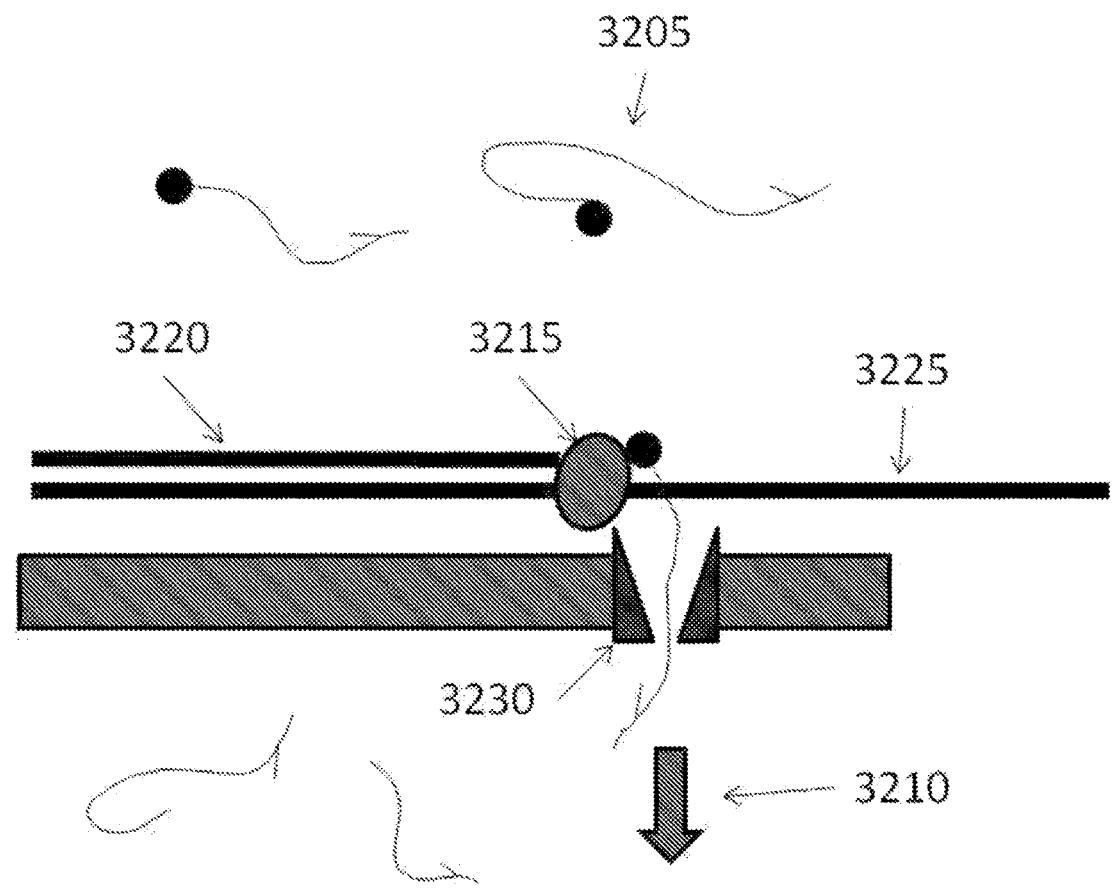
FIG. 32 shows an example of nucleic acid sequencing using a tagged nucleotide having a gate.

The disclosure also provides a method for sequencing a nucleic acid sample with the aid of a nanopore in a membrane adjacent to a sensing electrode. With reference to FIG. 32, the method can comprise providing tagged nucleotides 3205 into a reaction chamber comprising the nanopore, where an individual tagged nucleotide of the tagged nucleotides contains a tag coupled to a nucleotide where the tag is detectable with the aid of the nanopore. The tag comprises a first polymer chain comprising a first segment and a second segment, where the second segment is narrower than the first segment and a second polymer chain comprising two ends, where a first end is affixed to the first polymer chain adjacent to the second segment and a second end is not affixed to the first polymer chain. The tag molecule is capable of being threaded through a nanopore in a first direction 3210 where the second polymer chain aligns adjacent to the second segment.

The method includes carrying out a polymerization reaction with the aid of a polymerase 3215, thereby incorporating an individual tagged nucleotide of the tagged nucleotides into a growing strand 3220 complementary to a single stranded nucleic acid molecule 3225 from the nucleic acid sample. The method can include detecting, with the aid of the nanopore 3230, a tag associated with the individual tagged nucleotide during incorporation of the individual tagged nucleotide, wherein the tag is detected with the aid of the nanopore when the nucleotide is associated with the polymerase.

In some cases, the tag molecule is not capable of being threaded through the nanopore in a second direction where the second polymer chain does not align adjacent to the second segment.

The tag can be detected a plurality of times while associated with the polymerase. In some embodiments, an electrode is re-charged between tag detection periods. In some cases, the tag threads into the nanopore during incorporation of the individual tagged nucleotide and the tag does not thread out of the nanopore when the electrode is re-charged.

Methods for Attaching Tags

Any suitable method for attaching the tags may be used. In an example, tags may be attached to the terminal phosphate by (a) contacting a nucleotide triphosphate with dicyclohexylcarbodiimide/dimethylformamide under conditions permitting production of a cyclic trimetaphosphate; (b) contacting the product resulting from step a) with a nucleophile so as to form an —OH or —NH₂ functionalized compound; and (c) reacting the product of step b) with a tag having a —COR group attached thereto under conditions permitting the tag to bond indirectly to a terminal phosphate thereby forming the nucleotide triphosphate analogue.

In some cases, the nucleophile is H₂N—R—OH, H₂N—R—NH₂, R'S—R—OH, R'S—R—NH₂, or

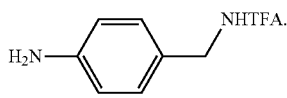

In some instances, the method comprises, in step b), contacting the product resulting from step a) with a compound having the structure:

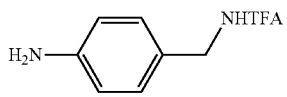

and subsequently or concurrently contacting the product with NH₄OH so as to form a compound having the structure:

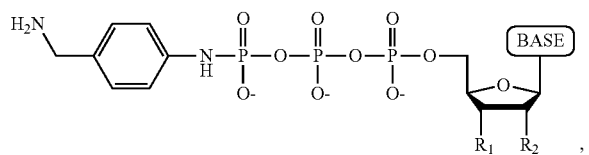

The product of step b) may then be reacted with a tag having a —COR group attached thereto under conditions permitting the tag to bond indirectly to a terminal phosphate thereby forming the nucleotide triphosphate analogue having the structure:

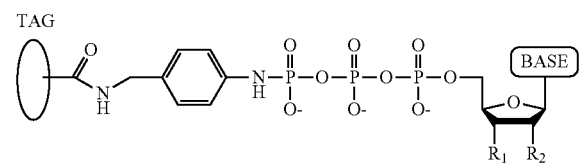

wherein $R_1$ is OH, wherein $R_2$ is H or OH, wherein the base is adenine, guanine, cytosine, thymine, uracil, a 7-deazapurine or a 5-methylpyrimidine.

Release of Tags

A tag may be released in any manner A tag can be released during or subsequent to the incorporation of a nucleotide having the tag into a growing nucleic acid strand. In some cases, the tag is attached to polyphosphate (e.g., FIG. 13) and incorporation of the nucleotide into a nucleic acid molecule results in release of a polyphosphate having the tag attached thereto. The incorporation may be catalyzed by at least one polymerase, which can be attached to the nanopore. In some instances, at least one phosphatase enzyme is also attached to the pore. The phosphatase enzyme may cleave the tag from the polyphosphate to release the tag. In some cases, the phosphatase enzymes are positioned such that pyrophosphate produced by the polymerase in a polymerase reaction interacts with the phosphatase enzymes before entering the pore.

In some cases, the tag is not attached to polyphosphate (see, e.g., FIG. 14). In these cases, the tag is attached by a linker (X), which is can be cleavable. Methods for production of cleavably capped and/or cleavably linked nucleotide analogues are disclosed in U.S. Pat. No. 6,664,079, which is entirely incorporated herein by reference. The linker need not be cleavable.

The linker may be any suitable linker and can be cleaved in any suitable manner. The linkers may be photocleavable. In an embodiment UV light is used to photochemically cleave the photochemically cleavable linkers and moieties. In an embodiment, the photocleavable linker is a 2-nitrobenzyl moiety.

The —CH₂N₃ group may be treated with TCEP (tris(2-carboxyethyl)phosphine) so as to remove it from the 3' O atom of a dNPP analogue, or rNPP analogue, thereby creating a 3' OH group.

Detection of Tags

In some instances, a polymerase draws from a pool of tagged nucleotides comprising a plurality of different bases (e.g., A, C, G, T, and/or U). It is also possible to iteratively contact the polymerase with the various types of tagged bases. In this case, it may not be necessary that each type of nucleotide have a unique base, but the cycling between different base types adds cost and complexity to the process in some cases, nevertheless this embodiment is encompassed in the present invention.

Figure 15:
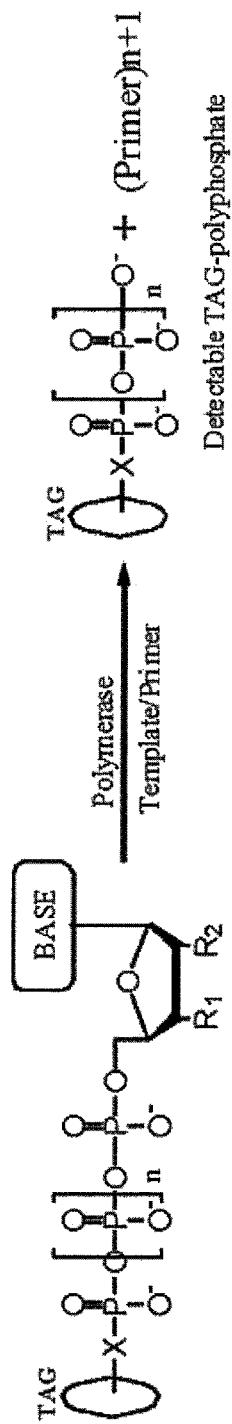
FIG. 15 shows detectable TAG-polyphosphate and detectable TAG.

FIG. 15 shows that incorporation of the tagged nucleotide into a nucleic acid molecule (e.g., using a polymerase to extend a primer base paired to a template) can release a detectable TAG-polyphosphate in some embodiments. In some cases, the TAG-polyphosphate is detected as it passes through the nanopore. In some embodiments, the TAG-polyphosphate is detected as it resides in the nanopore.

In some cases, the method distinguishes the nucleotide based on the number of phosphates comprising the polyphosphate (e.g., even when the TAGs are identical). Nevertheless, each type of nucleotide generally has a unique tag.

With reference to FIG. 15, the TAG-polyphosphate compound may be treated with phosphatase (e.g., alkaline phosphatase) before passing the tag into and/or through a nanopore and measuring the ionic current.

Tags may flow through a nanopore after they are released from the nucleotide. In some instances, a voltage is applied to pull the tags through the nanopore. At least about 85%, at least 90%, at least 95%, at least 99%, at least 99.9 or at least 99.99% of the released tags may translocate through the nanopore.

In some instances, the tags reside in the nanopore for a period of time where they are detected. In some instances, a voltage is applied to pull the tags into the nanopore, detect the tags, expel the tags from the nanopore, or any combination thereof. The tags can be released or remain bound to the nucleotide upon nucleotide incorporation events.

The tag may be detected in the nanopore (at least in part) because of its charge. In some instances, the tag compound is an alternatively charged compound which has a first net charge and, after a chemical, physical or biological reaction, a different second net charge. In some instance, the magnitude of the charge on the tag is the same as the magnitude of the charge on the rest of the compound. In an embodiment, the tag has a positive charge and removal of the tag changes the charge of the compound.

In some cases, as the tag passes into and/or through the nanopore, it may generate an electronic change. In some cases the electronic change is a change in current amplitude, a change in conductance of the nanopore, or any combination thereof.

The nanopore may be biological or synthetic. It is also contemplated that the pore is proteinaceous, for example wherein the pore is an alpha hemolysin protein. An example of a synthetic nanopore is a solid-state pore or graphene.

In some cases, polymerase enzymes and/or phosphatase enzymes are attached to the nanopore. Fusion proteins or disulfide crosslinks are example of methods for attaching to a proteinaceous nanopore. In the case of a solid state nanopore, the attachment to the surface near the nanopore may be via biotin-streptavidin linkages. In an example the DNA polymerase is attached to a solid surface via gold surface modified with an alkanethiol self-assembled monolayer functionalized with amino groups, wherein the amino groups are modified to NHS esters for attachment to amino groups on the DNA polymerase.

The method may be performed at any suitable temperature. In some embodiments, the temperature is between 4° C. and 10° C. In some embodiments, the temperature is ambient temperature.

The method may be performed in any suitable solution and/or buffer. In some instances, the buffer is 300 mM KCl buffered to pH 7.0 to 8.0 with 20 mM HEPES. In some embodiments, the buffer does not comprise divalent cations. In some cases, the method is unaffected by the presence of divalent cations.

Computer Systems for Sequencing Nucleic Acid Samples

Figure 16:
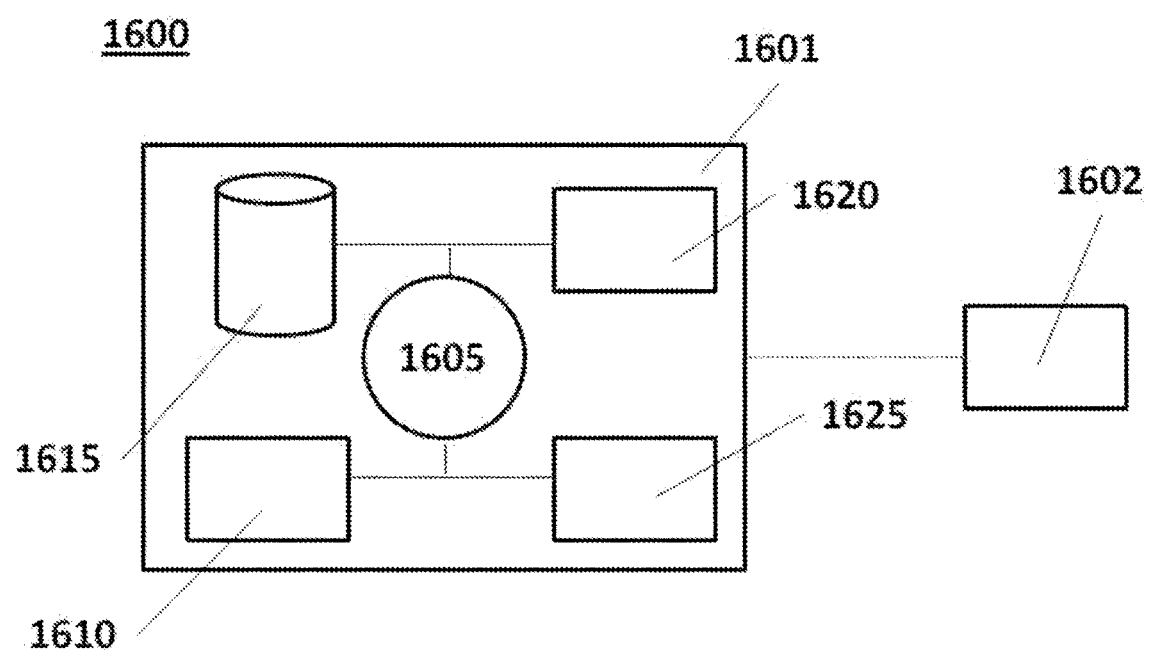
FIG. 16 shows a computer system configured to control a sequencer.

Nucleic acid sequencing systems and methods of the disclosure may be regulated with the aid of computer systems. FIG. 16 shows a system 1600 comprising a computer system 1601 coupled to a nucleic acid sequencing system 1602. The computer system 1601 may be a server or a plurality of servers. The computer system 1601 may be programmed to regulate sample preparation and processing, and nucleic acid sequencing by the sequencing system 1602. The sequencing system 1602 may be a nanopore-based sequencer (or detector), as described elsewhere herein.

The computer system may be programmed to implement the methods of the invention. The computer system 1601 includes a central processing unit (CPU, also "processor" herein) 1605, which can be a single core or multi core processor, or a plurality of processors for parallel processing. The computer system 1601 also includes memory 1610 (e.g., random-access memory, read-only memory, flash memory), electronic storage unit 1615 (e.g., hard disk), communications interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communications bus (solid lines), such as a motherboard. The storage unit 1615 can be a data storage unit (or data repository) for storing data. The computer system 1601 may be operatively coupled to a computer network ("network") with the aid of the communications interface 1620. The network can be the Internet, an internet and/or extranet, or an intranet and/or extranet that is in communication with the Internet. The network can include one or more computer servers, which can enable distributed computing.

Methods of the invention can be implemented by way of machine (or computer processor) executable code (or software) stored on an electronic storage location of the computer system 1601, such as, for example, on the memory 1610 or electronic storage unit 1615. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

The code can be pre-compiled and configured for use with a machine have a processer adapted to execute the code, or can be compiled during runtime. The code can be supplied in a programming language that can be selected to enable the code to execute in a pre-compiled or as-compiled fashion.

The computer system 1601 can be adapted to store user profile information, such as, for example, a name, physical address, email address, telephone number, instant messaging (IM) handle, educational information, work information, social likes and/or dislikes, and other information of potential relevance to the user or other users. Such profile information can be stored on the storage unit 1615 of the computer system 1601.

Aspects of the systems and methods provided herein, such as the computer system 1601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., ROM, RAM) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Systems and methods of the disclosure may be used to sequence various types of biological samples, such as nucleic acids (e.g., DNA, RNA) and proteins. In some embodiments, the methods, devices and systems described herein can be used to sort biological samples (e.g., proteins or nucleic acids). The sorted samples and/or molecules can be directed to various bins for further analysis.

Sequencing Accuracy

Methods provided herein may accurately distinguish between individual nucleotide incorporation events (e.g., single-molecule events). The methods may accurately distinguish between individual nucleotide incorporation events in a single pass—i.e., without having to re-sequence a given nucleic acid molecule. In some cases, methods provided herein may be used to sequence and re-sequence a nucleic acid molecule, or sense a single time or multiple times a tag associated with a tagged molecule. For instance, a tag can be sensed with the aid of a nanopore at least 1, 2, 3, 4, 5, 6, 7, 8, 9, 10, 20, 30, 40, 50, 60, 70, 80, 90, 100, 200, 300, 400, 500, 600, 700, 800, 900, 1000, or 10,000 times. The tag may be sensed and re-sensed with the aid of, for example, a voltage applied to a membrane having the nanopore, which can draw the tag into the nanopore or expel the tag from the nanopore.

A method for nucleic acid sequencing comprises distinguishing between individual nucleotide incorporation events with an accuracy of greater than about 4 σ. In some cases, the nucleotide incorporation events are detected with aid of a nanopore. Tags associated with the nucleotides may be released upon incorporation and the tags pass through the nanopore. In some instances the tags are not released (e.g., are presented to the nanopore). In yet more embodiments, the tags are released but reside in (e.g., do not pass through the nanopore). A different tag may be associated with and/or released from each type of nucleotide (e.g., A, C, T, G) and is detected by the nanopore. Errors include, but are not limited to, (a) failing to detect a tag, (b) mis-identifying a tag, (c) detecting a tag where there is no tag, (d) detecting tags in the incorrect order (e.g., two tags are released in a first order, but are detected in a second order), (e) a tag that has not been released from a nucleotide is detected as being released, (f) a tag that is not attached to an incorporated nucleotide is detected as being incorporated into the growing nucleotide chain, or any combination thereof. In some embodiments, the accuracy of distinguishing between individual nucleotide incorporation events is 100% subtracted by the rate at which errors occur (i.e., error rate).

The accuracy of distinguishing between individual nucleotide incorporation events is any suitable percentage. The accuracy of distinguishing between individual nucleotide incorporation events may be about 93%, about 94%, about 95%, about 96%, about 97%, about 98%, about 99%, about 99.5%, about 99.9%, about 99.99%, about 99.999%, about 99.9999%, and the like. In some cases, the accuracy of distinguishing between individual nucleotide incorporation events is at least 93%, at least 94%, at least 95%, at least 96%, at least 97%, at least 98%, at least 99%, at least 99.5%, at least 99.9%, at least 99.99%, at least 99.999%, at least 99.9999%, and the like. In some instances, the accuracy of distinguishing between individual nucleotide incorporation events is reported in sigma (n) units. Sigma is a statistical variable that is sometimes used in business management and manufacturing strategy to report error rates such as the percentage of defect-free products. Here, sigma values may be used interchangeably with accuracy according to the relationship as follows: 4 σ is 99.38% accuracy, 5 σ is 99.977% accuracy, and 6 σ is 99.99966% accuracy.

Distinguishing between individual nucleotide incorporation events, according to methods described herein, may be used to accurately determine a nucleic acid sequence. In some instances, the determination of the nucleic acid sequence of a nucleic acid (e.g., DNA and RNA) includes errors. Examples of errors include, but are not limited to deletions (failing to detect a nucleic acid) insertions (detecting a nucleic acid where none are truly present) and substitutions (detecting the incorrect nucleic acid). The accuracy of nucleic acid sequencing may be determined by lining up the measured nucleic acid sequence with the true nucleic acid sequence (e.g., according to bioinformatics techniques) and determining the percentage of nucleic acid positions that are deletions, insertions and/or substitutions. The errors are any combination of deletions, insertions and substitutions. The accuracy ranges from 0% to 100%, with 100% being a completely correct determination of the sequence of the nucleic acid. Similarly, the error rate is 100%—the accuracy and ranges from 0% to 100%, with 0% error rate being a completely correct determination of the sequence of the nucleic acid.

The accuracy of nucleic acid sequencing as performed according to the methods and/or using the devices described herein is high. The accuracy is any suitably high value. In some instances, the accuracy is about 95%, about 95.5%, about 96%, about 96.5%, about 97%, about 97.5%, about 98%, about 98.5%, about 99%, about 99.5%, about 99.9%, about 99.99%, about 99.999%, about 99.9999%, and the like. In some instances, the accuracy is at least 95%, at least 95.5%, at least 96%, at least 96.5%, at least 97%, at least 97.5%, at least 98%, at least 98.5%, at least 99%, at least 99.5%, at least 99.9%, at least 99.99%, at least 99.999%, at least 99.9999%, and the like. In some instances, the accuracy is between about 95% and 99.9999%, between about 97% and 99.9999%, between about 99% and 99.9999%, between about 99.5% and 99.9999%, between about 99.9% and 99.9999%, and the like.

High accuracy may be achieved by performing multiple passes (i.e., sequencing a nucleic acid molecule a plurality of times, e.g., by passing the nucleic acid through or in proximity to a nanopore and sequencing nucleic acid bases of the nucleic acid molecule). The data from multiple passes may be combined (e.g., deletions, insertions and/or substitutions in a first pass are corrected using data from other repeated passes). In some instances, the accuracy of detection of a tag can be increased by passing a tag through or adjacent to a nanopore multiple times, such as, for example, by reversing the voltage (e.g., DC or AC voltage) applied to the nanopore or membrane. The method provides high accuracy with few passes (also referred to as reads, multiplicity of sequencing coverage). The number of passes is any suitable number, and need not be an integer. In some embodiments, the nucleic acid molecule is sequenced 1 time, 2 times, 3 times, 4 times, 5 times, 6 times, 7 times, 8 times, 9 times, 10 times, 12 times, 14 times, 16 times, 18 times, 20 times, 25 times, 30 times, 35 times, 40 times, 45 times, 50 times, and the like. In some embodiments, the nucleic acid molecule is sequenced at most 1 time, at most 2 times, at most 3 times, at most 4 times, at most 5 times, at most 6 times, at most 7 times, at most 8 times, at most 9 times, at most 10 times, at most 12 times, at most 14 times, at most 16 times, at most 18 times, at most 20 times, at most 25 times, at most 30 times, at most 35 times, at most 40 times, at most 45 times, at most 50 times, and the like. In some embodiments, the nucleic acid molecule is sequenced between about 1 time and 10 times, between about 1 time and 5 times, between about 1 time and 3 times, and the like. The level of accuracy may be achieved by combining data collected from at most 20 passes. In some embodiments, the level of accuracy is achieved by combining data collected from at most 10 passes. In some embodiments, the level of accuracy is achieved by combining data collected from at most 5 passes. In some cases, the level of accuracy is achieved in a single pass.

The error rate is any suitably low rate. In some instances, the error rate is about 10%, about 5%, about 4%, about 3%, about 2%, about 1%, about 0.5%, about 0.1%, about 0.01%, about 0.001%, about 0.0001%, and the like. In some instances, the error rate is at most 10%, at most 5%, at most 4%, at most 3%, at most 2%, at most 1%, at most 0.5%, at most 0.1%, at most 0.01%, at most 0.001%, at most 0.0001%, and the like. In some instances, the error rate is between 10% and 0.0001%, between 3% and 0.0001%, between 1% and 0.0001%, between 0.01% and 0.0001%, and the like.

Removal of Repetitive Sequences

Genomic DNA can contain repetitive sequences that in some cases are not of interest when performing nucleic acid sequencing reactions. Provided herein are methods for removing these repetitive sequences (e.g., by hybridization with sequences complimentary to the repetitive sequences, e.g., Cot-1 DNA).

In an aspect, a method for sequencing a nucleic acid sample with the aid of a nanopore in a membrane adjacent to a sensing electrode comprises removing a repetitive nucleic acid sequence from the nucleic acid sample to provide a single-stranded nucleic acid molecule for sequencing. The method can further include providing tagged nucleotides into a reaction chamber comprising the nanopore, where an individual tagged nucleotide of the tagged nucleotides contains a tag coupled to a nucleotide that is detectable with the aid of the nanopore. In some cases, the method includes carrying out a polymerization reaction with the aid of a polymerase, thereby incorporating an individual tagged nucleotide of the tagged nucleotides into a growing strand complementary to the single-stranded nucleic acid molecule. The method can include detecting, with the aid of the nanopore, a tag associated with the individual tagged nucleotide during incorporation of the individual tagged nucleotide, wherein the tag is detected with the aid of the nanopore when the nucleotide is associated with the polymerase.

In some cases, the repetitive sequences are not physically removed from the reaction, but are rendered incapable of being sequenced and left in the reaction mixture (e.g., by hybridization with Cot-1 DNA, which renders the repetitive sequences double stranded and effectively "removed" form the sequencing reaction). In some cases, repetitive sequences are made to be double stranded.

The repetitive sequence can have any suitable length. In some cases, the repetitive nucleic acid sequence comprises about 20, about 40, about 60, about 80, about 100, about 200, about 400, about 600, about 800, about 1000, about 5000, about 10000, or about 50000 nucleic acid bases. In some cases, the repetitive nucleic acid sequence comprises at least about 20, at least about 40, at least about 60, at least about 80, at least about 100, at least about 200, at least about 400, at least about 600, at least about 800, at least about 1000, at least about 5000, at least about 10000, or at least about 50000 nucleic acid bases. In some cases, the bases are consecutive.

The repetitive nucleic acid sequence can have any number of repeated subunits. In some cases, the repeated subunits are consecutive. In some embodiments, the repetitive nucleic acid sequence comprises about 20, about 40, about 60, about 80, about 100, about 200, about 400, about 600, about 800, or about 1000 repeated subunits of nucleic acid bases. In some cases, the repetitive nucleic acid sequence comprises at least about 20, at least about 40, at least about 60, at least about 80, at least about 100, at least about 200, at least about 400, at least about 600, at least about 800, or at least about 1000 repeated subunits of nucleic acid bases.

In some cases, the repetitive nucleic acid sequence is removed by hybridization with a nucleic acid sequence complimentary to the repetitive nucleic acid sequence. The nucleic acid sequence complimentary to the repetitive nucleic acid sequence can be immobilized on a solid support such as a surface or a bead. In some cases, the nucleic acid sequence complimentary to the repetitive nucleic acid sequence comprises Cot-1 DNA (which is an example of repetitive nucleic acid sequences having a length of between about 50 and about 100 nucleic acid bases).

Nanopore Assembly and Insertion

The methods described herein can use a nanopore having a polymerase attached to the nanopore. In some cases, it is desirable to have one and only one polymerase per nanopore (e.g., so that only one nucleic acid molecule is sequenced at each nanopore). However, many nanopores, including alpha-hemolysin (αHL), can be multimeric proteins having a plurality of subunits (e.g., 7 subunits for αHL). The subunits can be identical copies of the same polypeptide. Provided herein are multimeric proteins (e.g., nanopores) having a defined ratio of modified subunits to un-modified subunits. Also provided herein are methods for producing multimeric proteins (e.g., nanopores) having a defined ratio of modified subunits to un-modified subunits.

Figure 27:
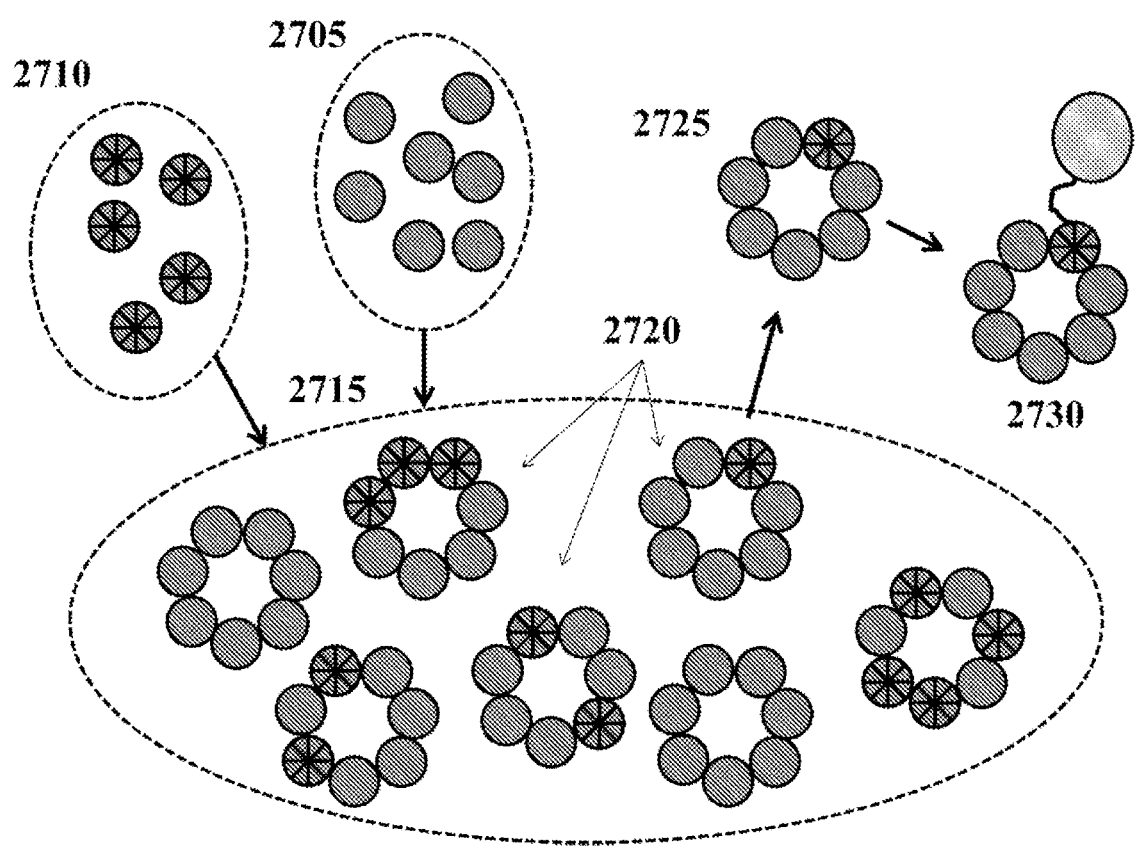
FIG. 27 shows an example of a method for forming multimeric proteins having a defined number of modified subunits.

With reference to FIG. 27, a method for assembling a protein having a plurality of subunits comprises providing a plurality of first subunits 2705 and providing a plurality of second subunits 2710, where the second subunits are modified when compared with the first subunits. In some cases, the first subunits are wild-type (e.g., purified from native sources or produced recombinantly). The second subunits can be modified in any suitable way. In some cases, the second subunits have a protein (e.g., a polymerase) attached (e.g., as a fusion protein). The modified subunits can comprise a chemically reactive moiety (e.g., an azide or an alkyne group suitable for forming a linkage). In some cases, the method further comprises performing a reaction (e.g., a Click chemistry cycloaddition) to attach an entity (e.g., a polymerase) to the chemically reactive moiety.

The method can further comprise contacting the first subunits with the second subunits 2715 in a first ratio to form a plurality of proteins 2720 having the first subunits and the second subunits. For example, one part modified αHL subunits having a reactive group suitable for attaching a polymerase can be mixed with six parts wild-type αHL subunits (i.e., with the first ratio being 1:6). The plurality of proteins can have a plurality of ratios of the first subunits to the second subunits. For example, the mixed subunits can form several nanopores having a distribution of stoichiometrics of modified to un-modified subunits (e.g., 1:6, 2:5, 3:4).

In some cases, the proteins are formed by simply mixing the subunits. In the case of αHL nanopores for example, a detergent (e.g., deoxycholic acid) can trigger the αHL monomer to adopt the pore conformation. The nanopores can also be formed using a lipid (e.g., 1,2-diphytanoyl-sn-glycero-3-phosphocholine (DPhPC) or 1,2-di-O-phytanyl-sn-glycero-3-phosphocholine (DoPhPC)) and moderate temperature (e.g., less than about 100° C.). In some cases, mixing DPhPC with a buffer solution creates large multilamellar vesicles (LMV), and adding αHL subunits to this solution and incubating the mixture at 40° C. for 30 minutes results in pore formation.

If two different types of subunits are used (e.g., the natural wild type protein and a second αHL monomer which can contain a single point mutation), the resulting proteins can have a mixed stoichiometry (e.g., of the wild type and mutant proteins). The stoichiometry of these proteins can follow a formula which is dependent upon the ratio of the concentrations of the two proteins used in the pore forming reaction. This formula is as follows:

$$100 P_m = 100 [n!/m!(n-m)!] \cdot f_{mut}^m \cdot f_{wt}^{n-m}, \text{ where}$$

$P_m$=probability of a pore having m number of mutant subunits
n=total number of subunits (e.g., 7 for αHL)
m=number of "mutant" subunits
$f_{mut}$=fraction or ratio of mutant subunits mixed together
$f_{wt}$=fraction or ratio of wild-type subunits mixed together The method can further comprise fractionating the plurality of proteins to enrich proteins that have a second ratio of the first subunits to the second subunits 2725. For example, nanopore proteins can be isolated that have one and only one modified subunit (e.g., a second ratio of 1:6). However, any second ratio is suitable. A distribution of second ratios can also be fractionated such as enriching proteins that have either one or two modified subunits. The total number of subunits forming the protein is not always 7 (e.g., a different nanopore can be used or an alpha-hemolysin nanopore can form having six subunits) as depicted in FIG. 27. In some cases, proteins having only one modified subunit are enriched. In such cases, the second ratio is 1 second subunit per (n−1) first subunits where n is the number of subunits comprising the protein.

The first ratio can be the same as the second ratio, however this is not required. In some cases, proteins having mutated monomers can form less efficiently than those not having mutated subunits. If this is the case, the first ratio can be greater than the second ratio (e.g., if a second ratio of 1 mutated to 6 non-mutated subunits are desired in a nanopore, forming a suitable number of 1:6 proteins may require mixing the subunits at a ratio greater than 1:6).

Figure 28:
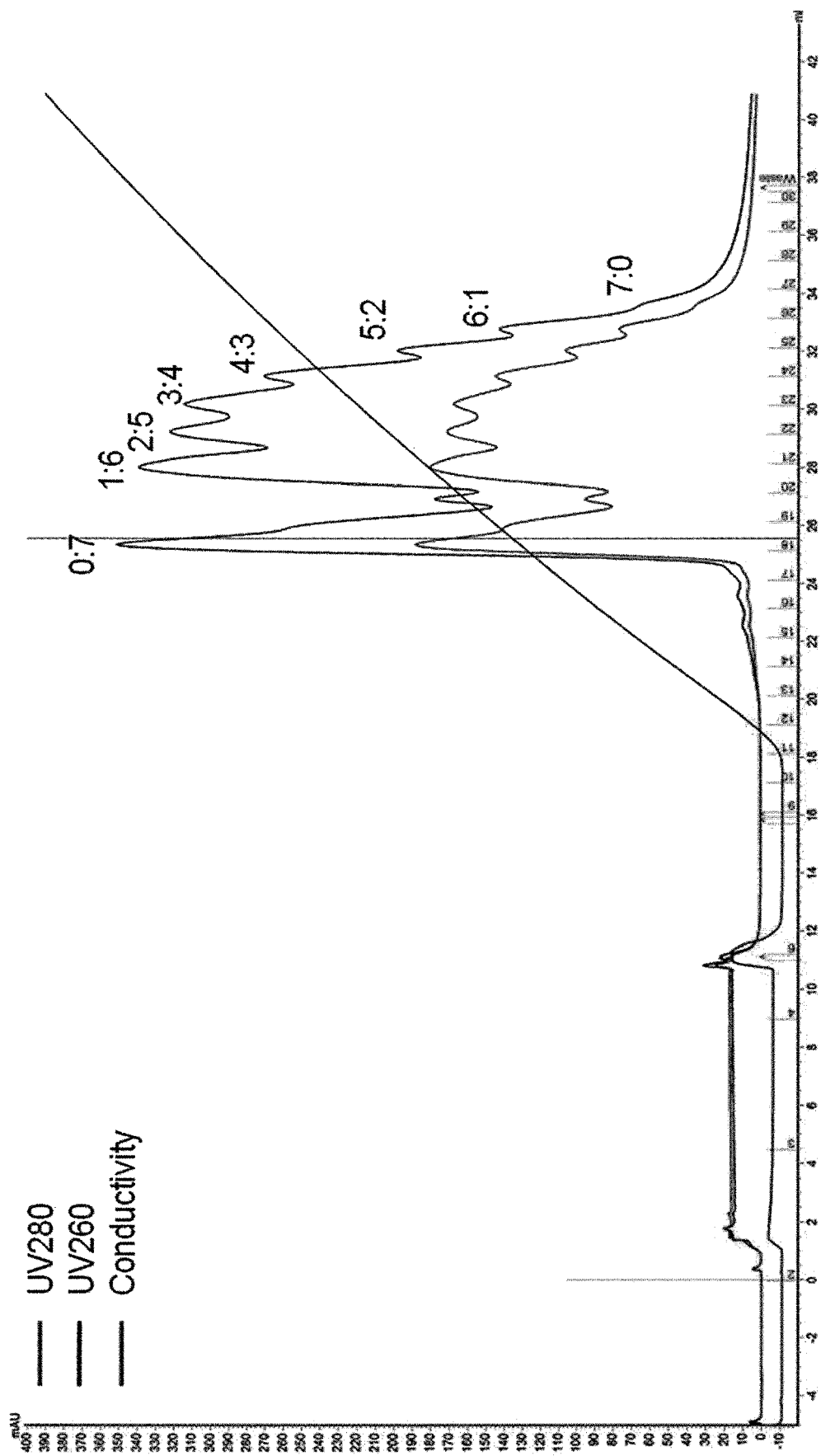
FIG. 28 shows an example of fractionating a plurality of nanopores having a distribution of different numbers of modified subunits.
Figure 29:
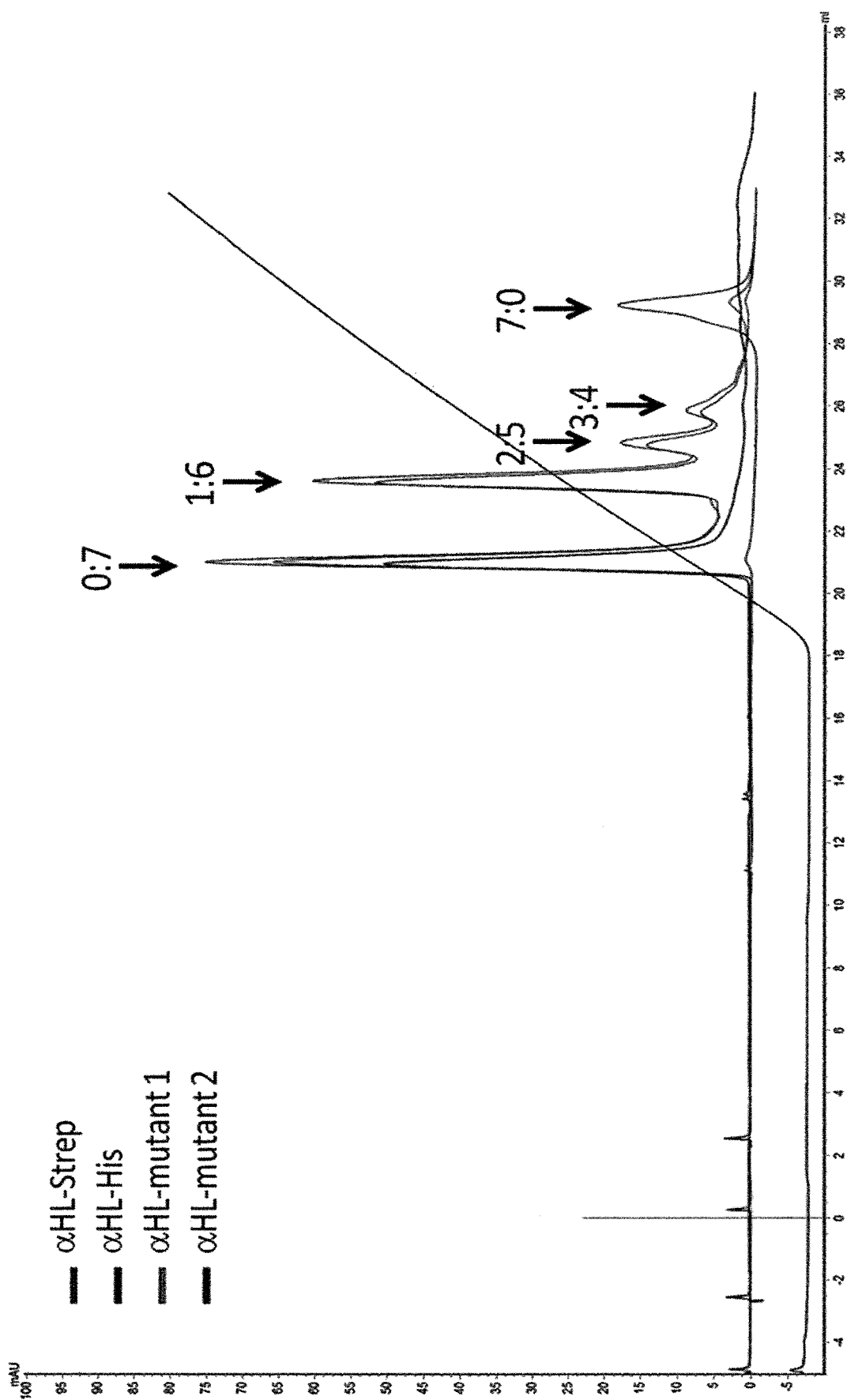
FIG. 29 shows an example of fractionating a plurality of nanopores having a distribution of different numbers of modified subunits.

Proteins having different second ratios of subunits can behave differently (e.g., have different retention times) in a separation. In some cases, the proteins are fractionated using chromatography, such as ion exchange chromatography or affinity chromatography. Since the first and second subunits can be identical apart from the modification, the number of modifications on the protein can serve as a basis for separation. In some cases, either the first or second subunits have a purification tag (e.g., in addition to the modification) to allow or improve the efficiency of the fractionation. In some cases, a poly-histidine tag (His-tag), a streptavidin tag (Strep-tag), or other peptide tag is used. In some instances, the first and second subunits each comprise different tags and the fractionation step fractionates on the basis of each tag. In the case of a His-tag, a charge is created on the tag at low pH (Histidine residues become positively charged below the pKa of the side chain). With a significant difference in charge on one of the αHL molecules compared to the others, ion exchange chromatography can be used to separate the oligomers which have 0, 1, 2, 3, 4, 5, 6, or 7 of the "charge-tagged" αHL subunits. In principle, this charge tag can be a string of any amino acids which carry a uniform charge. FIG. 28 and FIG. 29 show examples of fractionation of nanopores based on a His-tag. FIG. 28 shows a plot of ultraviolet absorbance at 280 nanometers, ultraviolet absorbance at 260 nanometers, and conductivity. The peaks correspond to nanopores with various ratios of modified and unmodified subunits. FIG. 29 shows fractionation of αHL nanopores and mutants thereof using both His-tag and Strep-tags.

In some cases, an entity (e.g., a polymerase) is attached to the protein following fractionation 2730. The protein can be a nanopore and the entity can be a polymerase. In some instances, the method further comprises inserting the proteins having the second ratio subunits into a bilayer.

In some situations, a nanopore can comprise a plurality of subunits. A polymerase can be attached to one of the subunits and at least one and less than all of the subunits comprise a first purification tag. In some examples, the nanopore is alpha-hemolysin or a variant thereof. In some instances, all of the subunits comprise a first purification tag or a second purification tag. The first purification tag can be a poly-histidine tag (e.g., on the subunit having the polymerase attached).

Linkers

Methods described herein can use an enzyme (e.g., polymerase) attached to a nanopore for nanopore detection, including nucleic acid sequencing. In some cases, the link between the enzyme and the nanopore can affect the performance of the system. For example, engineering an attachment of the DNA polymerase to the pore (alpha-hemolysin) can increase effective tagged nucleotide concentration, thereby lowering entropic barrier. In some cases, the polymerase is attached directly to the nanopore. In other cases, a linker is used between the polymerase and the nanopore.

The tag sequencing described herein can benefit from an efficient capture of a specific tag-nucleotide to the αHL pore induced by electric potential. The capture can happen during or after polymerase primer extension based on the DNA template. One method to improve the efficiency of capture is to optimize the connection between polymerase and the αHL pore. Without limitation, three features of the connection to be optimized are: (a) the length of the connection (which can increase effective tagged nucleotide concentration, affect the kinetics of capture, and/or change the entropic barrier); (b) connection flexibility (which can influence the kinetics of the connector conformational changes); and (c) the number and location of the connections between the polymerase and the nanopore (which can reduce the number of available conformational states, thereby increasing the likelihood of proper pore-polymerase orientation, increase effective tagged nucleotide concentration and reduce the entropic barrier).

The enzyme and the polymerase can be connected in any suitable way. In some cases, the open reading frames (ORF) are fused, either directly or with a linker of amino acids. The fusion can be in any order. In some cases, a chemical bond is formed (e.g., by click chemistry). In some cases, the connection is non-covalent (e.g., molecular staples, through biotin-streptavidin interactions, or through protein-protein tags such as the PDZ, GBD, SpyTag, Halo tag, or SH3 ligands).

In some cases, the linker is a polymer such as a peptide, nucleic acid, polyethylene glycol (PEG). The linker can be any suitable length. For example, the linker can be about 5 nanometers (nm), about 10 nm, about 15 nm, about 20 nm, about 40 nm, about 50 nm, or about 100 nm long. In some cases, the linker is at least about 5 nanometers (nm), at least about 10 nm, at least about 15 nm, at least about 20 nm, at least about 40 nm, at least about 50 nm, or at least about 100 nm long. In some cases, the linker is at most about 5 nanometers (nm), at most about 10 nm, at most about 15 nm, at most about 20 nm, at most about 40 nm, at most about 50 nm, or at most about 100 nm long. The linker can be rigid, flexible, or any combination thereof. In some cases, no linker is used (e.g., the polymerase is attached directly to the nanopore).

In some cases, more than one linker connects the enzyme with the nanopore. The number and location of the connection between polymerase and nanopore can be varied. Examples include: αHL C-terminus to polymerase N-terminus; αHL N-terminus to polymerase C-terminus; and connections between amino acids not at the terminus.

In an aspect, a method for sequencing a nucleic acid sample with the aid of a nanopore in a membrane adjacent to a sensing electrode comprises providing tagged nucleotides into a reaction chamber comprising the nanopore, where an individual tagged nucleotide of the tagged nucleotides contains a tag coupled to a nucleotide that is detectable with the aid of the nanopore. The method can include carrying out a polymerization reaction with the aid of a polymerase attached by a linker to the nanopore, thereby incorporating an individual tagged nucleotide of the tagged nucleotides into a growing strand complementary to a single stranded nucleic acid molecule from the nucleic acid sample. The method can include detecting, with the aid of the nanopore, a tag associated with the individual tagged nucleotide during incorporation of the individual tagged nucleotide, where the tag is detected with the aid of the nanopore when the nucleotide is associated with the polymerase.

In some cases, the linker orients the polymerase with respect to the nanopore such that the tag is detected with the aid of the nanopore. In some instances, the polymerase is attached to the nanopore by two or more linkers.

In some cases the linker comprises one or more of SEQ ID Nos 2-35 or a PCR product sequenced therefrom. In some instances, the linker comprises the peptide encoded by one or more of SEQ ID Nos 2-35 or a PCR product produced therefrom. Table discloses "GGGGSG," "GGGGS," and EAAAK" as SEQ ID Nos 38-39, respectively.

| SEQ. ID. No. | Name | Sequence (5'-3') |
| --- | --- | --- |
| 2 | 1-GGGGSG_For | GATCG GGAGGAGGTGGGAGCGGA G |
| 3 | 1-GGGGSG_Rev | GATCC TCCGCTCCCACCTCCTCC C |
| 4 | 2-GGGGS_For | GATCG GGAGGAGGTGGGAGCGGAGGAGGTGGGAGCGGA G |
| 5 | 2-GGGGS_Rev | GATCC TCCGCTCCCACCTCCTCCGCTCCCACCTCCTCC C |
| 6 | 3-GGGGS_For | GGAGGAGGTGGGAGCGGAGGAGGTGGGAGCGGAGGAGGTGGGAGCGGA G |
| 7 | 3-GGGGS_Rev | GATCC TCCGCTCCCACCTCCTCCGCTCCCACCTCCTCCGCTCCCACCTCCT CC C |
| 8 | 4-GGGGS_For | GGAGGAGGTGGGAGCGGAGGAGGTGGGAGCGGAGGAGGTGGGAGCGGAGGAGGTGGGAGCGGA G |
| 9 | 4-GGGGS_Rev | TCCGCTCCCACCTCCTCCGCTCCCACCTCCTCCGCTCCCACCTCCTCCGCTCCCACCTCCTCC C |
| 10 | 5-GGGGS_For | GATCG GGAGGAGGTGGGAGCGGAGGAGGTGGGAGCGGAGGAGGTGGGAGCGGAGGAGGTGGGAGCGGA G |
| 11 | 5-GGGGS_Rev | GATCC TCCGCTCCCACCTCCTCCGCTCCCACCTCCTCCGCTCCCACCTCCTCCGCTCCCACCTCCTCCGCTCCCACCTCCTCC C |
| 12 | 6-GGGGS_For | GATCG GGAGGAGGTGGGAGCGGAGGAGGTGGGAGCGGAGGAGGTGGGAGCGGAGGAGGTGGGAGCGGAGGAGGTGGGAGCGGA G |

-continued

| SEQ. ID. No. | Name | Sequence (5'-3') |
|---|---|---|
| 13 | 6-GGGGS_Rev | GATCC TCCGCTCCCACCTCCTCCTCCGCTCCCACCTCCTCCGCTCCCACCT CCTCCGCTCCCACCTCCTCCGCTCCCACCTCCTCCGCTCCCACCTC CTCC C |
| 14 | 2-EAAAK_For | GATCG GGAGAAGCGGCAGCGAAAGAAGCGGCAGCGAAAGGA G |
| 15 | 2-EAAAK_Rev | GATCC TCCTTTCGCTGCCGCTTCTTTCGCTGCCGCTTCTCC C |
| 16 | 4-EAAAK_For | GATCG GGAGAAGCGGCAGCGAAAGAAGCGGCAGCGAAAGAAGCGGCAG CGAAAGAAGCGGCAGCGAAAGGA G |
| 17 | 4-EAAAK_Rev | GATCC TCCTTTCGCTGCCGCTTCTTTCGCTGCCGCTTCTTTCGCTGCCGCT TCTTTCGCTGCCGCTTCTCC C |
| 18 | 4-EAAAK_Flex_For | GATCGGGAGAAGCGGCAGCGAAAGAAGCGGCAGCGAAAGGAGG AGAAGCGGCAGCGAAAGAAGCGGCAGCGAAAGGAG |
| 19 | 4-EAAAK_Flex_Rev | GATCCTCCTTTCGCTGCCGCTTCTTTCGCTGCCGCTTCTCCTCCTT TCGCTGCCGCTTCTTTCGCTGCCGCTTCTCCC |
| 20 | 6-EAAAK_For | GATCG GGAGAAGCGGCAGCGAAAGAAGCGGCAGCGAAAGAAGCGGCAG CGAAAGAAGCGGCAGCGAAAGAAGCGGCAGCGAAAGAAGCGGC AGCGAAAGGA G |
| 21 | 6-EAAAK_Rev | GATCC TCCTTTCGCTGCCGCTTCTTTCGCTGCCGCTTCTTTCGCTGCCGCT TCTTTCGCTGCCGCTTCTTTCGCTGCCGCTTCTTTCGCTGCCGCTT CTCC C |
| 22 | 6-EAAAK_Flex_For | GATCG GGAGAAGCGGCAGCGAAAGAAGCGGCAGCGAAAGGAGGAGAA GCGGCAGCGAAAGAAGCGGCAGCGAAAGGAGGAGAAGCGGCAG CGAAAGAAGCGGCAGCGAAAGGA G |
| 23 | 6-EAAAK_Flex_Rev | GATCC TCCTTTCGCTGCCGCTTCTTTCGCTGCCGCTTCTCCTCCTTTCGCT GCCGCTTCTTTCGCTGCCGCTTCTCCTCCTTTCGCTGCCGCTTCTT TCGCTGCCGCTTCTCC C |
| 24 | 8-EAAAK_For | GATCG GGAGAAGCGGCAGCGAAAGAAGCGGCAGCGAAAGAAGCGGCAG CGAAAGAAGCGGCAGCGAAAGAAGCGGCAGCGAAAGAAGCGGC AGCGAAAGAAGCGGCAGCGAAAGAAGCGGCAGCGAAAGGA G |
| 25 | 8-EAAAK_Rev | GATCC TCCTTTCGCTGCCGCTTCTTTCGCTGCCGCTTCTTTCGCTGCCGCT TCTTTCGCTGCCGCTTCTTTCGCTGCCGCTTCTTTCGCTGCCGCTT CTTTCGCTGCCGCTTCTTTCGCTGCCGCTTCTCC C |
| 26 | 8-EAAAK_Flex_For | GATCG GGAGAAGCGGCAGCGAAAGAAGCGGCAGCGAAAGAAGCGGCAG CGAAAGAAGCGGCAGCGAAAGGAGGAGAAGCGGCAGCGAAAGA AGCGGCAGCGAAAGAAGCGGCAGCGAAAGAAGCGGCAGCGAAA GGA G |
| 27 | 8-EAAAK_Flex_Rev | GATCC TCCTTTCGCTGCCGCTTCTTTCGCTGCCGCTTCTTTCGCTGCCGCT TCTTTCGCTGCCGCTTCTCCTCCTTTCGCTGCCGCTTCTTTCGCTG CCGCTTCTTTCGCTGCCGCTTCTTTCGCTGCCGCTTCTCC C |
| 28 | 10-EAAAK_For | GATCG GGAGAAGCGGCAGCGAAAGAAGCGGCAGCGAAAGAAGCGGCAG CGAAAGAAGCGGCAGCGAAAGAAGCGGCAGCGAAAGAAGCGGC AGCGAAAGAAGCGGCAGCGAAAGAAGCGGCAGCGAAAGAAGCG GCAGCGAAAGAAGCGGCAGCGAAAGGA G |

-continued

| SEQ. ID. No. | Name | Sequence (5'-3') |
|---|---|---|
| 29 | 10-EAAAK_Rev | GATCC TCCTTTCGCTGCCGCTTCTTTCGCTGCCGCTTCTTTCGCTGCCGCT TCTTTCGCTGCCGCTTCTTTCGCTGCCGCTTCTTTCGCTGCCGCTT CTTTCGCTGCCGCTTCTTTCGCTGCCGCTTCTTTCGCTGCCGCTTC TTTCGCTGCCGCTTCTCC C |
| 30 | 10-EAAAK_Flex_For | GATCG GGAGAAGCGGCAGCGAAAGAAGCGGCAGCGAAAGGAGGAGAA GCGGCAGCGAAAGAAGCGGCAGCGAAAGAAGCGGCAGCGAAAG AAGCGGCAGCGAAAGAAGCGGCAGCGAAAGAAGCGGCAGCGAA AGGAGGAGAAGCGGCAGCGAAAGAAGCGGCAGCGAAAGGA G |
| 31 | 10-EAAAK_Flex_Rev | GATCC TCCTTTCGCTGCCGCTTCTTTCGCTGCCGCTTCTCCTCCTTTCGCT GCCGCTTCTTTCGCTGCCGCTTCTTTCGCTGCCGCTTCTTTCGCTG CCGCTTCTTTCGCTGCCGCTTCTTTCGCTGCCGCTTCTCCTCCTTTC GCTGCCGCTTCTTTCGCTGCCGCTTCTCC C |
| 32 | 12-EAAAK_For | GATCG GGAGAAGCGGCAGCGAAAGAAGCGGCAGCGAAAGAAGCGGCAG CGAAAGAAGCGGCAGCGAAAGAAGCGGCAGCGAAAGAAGCGGC AGCGAAAGAAGCGGCAGCGAAAGAAGCGGCAGCGAAAGCG GCAGCGAAAGAAGCGGCAGCGAAAGAAGCGGCAGCGAAAGAAG CGGCAGCGAAGGA G |
| 33 | 12-EAAAK_Rev | GATCC TCCTTTCGCTGCCGCTTCTTTCGCTGCCGCTTCTTTCGCTGCCGCT TCTTTCGCTGCCGCTTCTTTCGCTGCCGCTTCTTTCGCTGCCGCTT CTTTCGCTGCCGCTTCTTTCGCTGCCGCTTCTTTCGCTGCCGCTTC TTTCGCTGCCGCTTCTTTCGCTGCCGCTTCTTTCGCTGCCGCTTCT CC C |
| 34 | 12-EAAAK_Flex_For | GATCG GGAGAAGCGGCAGCGAAAGAAGCGGCAGCGAAAGAAGCGGCAG CGAAAGAAGCGGCAGCGAAAGGAGAAGCGGCAGCGAAAGAAGC GGCAGCGAAAGAAGCGGCAGCGAAAGAAGCGGCAGCGAAAGGA GAAGCGGCAGCGAAAGAAGCGGCAGCGAAAGAAGCGGCAGCGA AAGAAGCGGCAGCGAAAGGA G |
| 35 | 12-EAAAK_Flex_Rev | GATCC TCCTTTCGCTGCCGCTTCTTTCGCTGCCGCTTCTTTCGCTGCCGCT TCTTTCGCTGCCGCTTCTCCTTTCGCTGCCGCTTCTTTCGCTGCCG CTTCTTTCGCTGCCGCTTCTTTCGCTGCCGCTTCTCCTTTCGCTGC CGCTTCTTTCGCTGCCGCTTCTTTCGCTGCCGCTTCTTTCGCTGCC GCTTCTCC C |

Calibration of Applied Voltage

Molecule-specific output signals from single-molecule nanopore sensor devices can originate from the presence of an electrochemical potential difference across an ionically impermeable membrane surrounded by an electrolyte solution. This transmembrane potential difference can determine the strength of the nanopore-specific electrochemical current that can be detected by electronics within the device via either sacrificial (i.e., Faradaic) or nonsacrificial (i.e., capacitative) reactions occurring at the electrode surfaces.

For any given state of the nanopore (i.e., open channel, captured state, etc.), the time-dependent trans-membrane potential can act as an input signal that can determine the resulting current flowing through the nanopore complex as a function of time. This nanopore current can provide the specific molecular signal output by the nanopore sensor device. The open-channel nanopore current can be modulated to varying degrees by the interactions between the nanopore and the captured molecules which partially block the flow of ions through the channel.

These modulations can exhibit specificity for the type of molecule that has been captured, allowing some molecules to be identified directly from their nanopore current modulations. For a given molecule type and a fixed set of device conditions, the degree of modulation of the open-channel nanopore current by a captured molecule of this type can vary depending on the trans-membrane potential applied, mapping each type of molecule to a particular current-vs.-voltage (I-V) curve.

Systematically variable offsets between the applied voltage settings and the trans-membrane potential can introduce horizontal shifts of this I-V curve along the horizontal voltage axis, potentially reducing the accuracy of molecular identification based on the measured current signals reported by the nanopore sensor device as an output signal. Therefore, uncontrolled offset between the applied and trans-membrane potentials can be problematic for accurately comparing measurements of the same molecule under the same conditions.

This so-called "potential offset" between the externally-applied potential and the actual trans-membrane potential can vary both within and between experiments. Variations in potential offset can be caused by both variations in initial conditions and by time-dependent variations (drift) in the electrochemical conditions within the nanopore sensor device.

Removing these measurement errors can be done as described here by calibrating the time-dependent offset between the applied voltage and the trans-membrane potential for each experiment. Physically, the probability of observing escape events of nanopore-captured molecules can depend on the trans-membrane potential applied and this probability distribution can be the same for identical samples of molecules under the same conditions (e.g., the sample may be a mixture of different types of molecules provided that their proportions do not vary between samples). In some cases, the distribution of voltages where escape events occur for a fixed sample type provides a measure of the offset between the applied and trans-membrane potentials. This information can be used in order to calibrate the applied voltage across the nanopore, eliminating systematic sources of error caused by potential offsets within and between experiments and improving the accuracy of molecular identification and other measurements.

For a given nanopore sensor apparatus operated with the same molecular sample and reagents, the expected value of the distribution of escape voltages can be estimated from a statistical sample of the single molecular escape events (although each individual event can be a stochastic process subject to random fluctuations). This estimate can be time-dependent to account for temporal drift of the potential offset within the experiment. This can correct for the variable difference between applied voltage settings and actual voltage felt at the pore, effectively "lining up" all the measurements horizontally when plotted in T-V space.

In some cases, potential (i.e. voltage) offset calibration does not account for current gain and current offset variations, which can also be calibrated for improved accuracy and reproducibility of nanopore current measurements. However, potential offset calibration is generally done prior to gain and offset correction to prevent errors in estimating the current gain and current offset variations, since these in turn can involve fitting current vs. voltage (I-V) curves, and the results of these fits are affected by variations in voltage offset. I.e., shifting the data left-to-right (horizontally) in I-V space can introduce errors in subsequent current gain and current offset fits.

Figure 30:
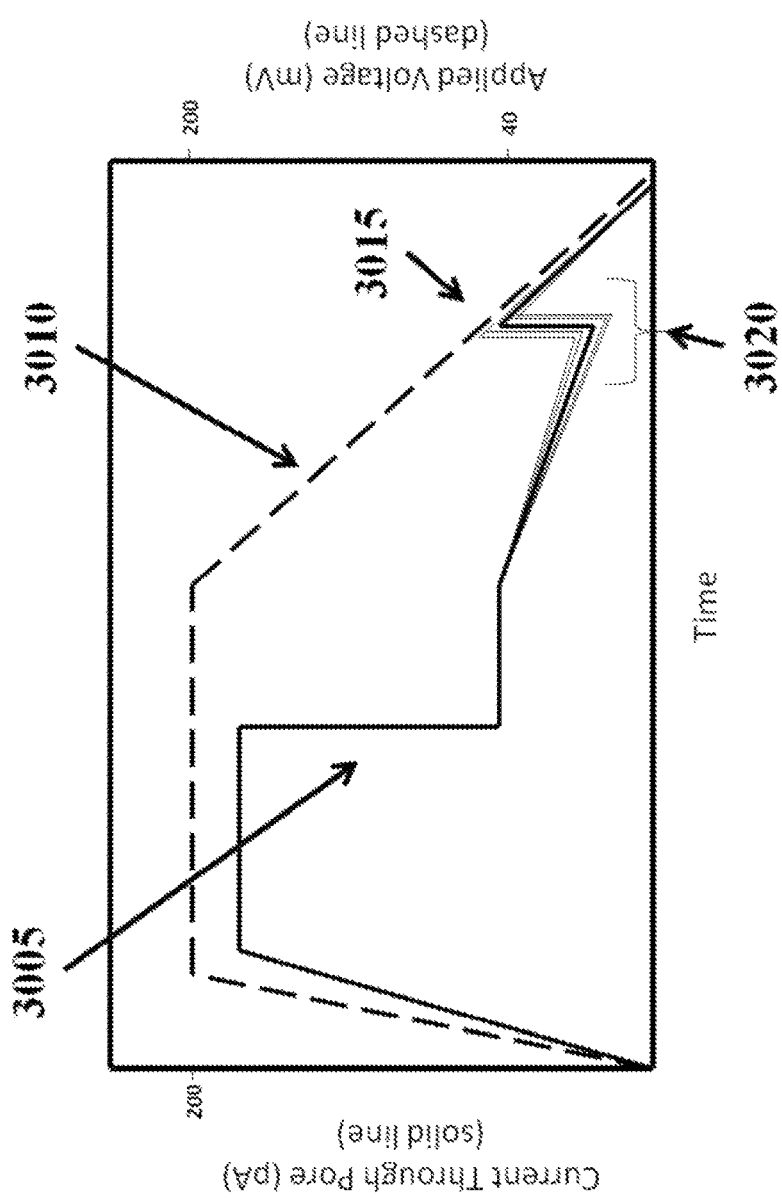
FIG. 30 shows an example of calibration of the applied voltage.

FIG. 30 shows a plot of current through the nanopore (solid lines) and applied voltage (dashed lines) versus time. The current can decrease when a molecule is captured in the nanopore 3005. As the applied voltage is decreased over time 3010, the current decreases until the molecule falls out of the nanopore 3015, at which time the current increases to the expected level at the applied voltage. The applied voltage at which the molecule falls out can depend on the length of the molecule. For example, a tag having 30 bases can fall out around 40 mV, while a tag having 50 bases can fall out around 10 mV. There can be variation 3020 in the fall-out voltage for different nanopores or for different measurements on the same nanopore over time. Adjusting this fall-out voltage to an expected value can make the data easier to interpret and/or more accurate.

In an aspect, provided herein is a method for sequencing a nucleic acid sample with the aid of a nanopore in a membrane adjacent to a sensing electrode. The method can include providing tagged nucleotides into a reaction chamber comprising a nanopore, where an individual tagged nucleotide of the tagged nucleotides contains a tag coupled to a nucleotide that is detectable with the aid of the nanopore. The method can include carrying out a polymerization reaction with the aid of a polymerase, thereby incorporating an individual tagged nucleotide of the tagged nucleotides into a growing strand complementary to a single stranded nucleic acid molecule from the nucleic acid sample. The method can then include detecting, with the aid of the nanopore, a tag associated with the individual tagged nucleotide during incorporation of the individual tagged nucleotide, where the tag is detected with the aid of the nanopore when the nucleotide is associated with the polymerase. In some cases, the detecting comprises applying an applied voltage across the nanopore and measuring a current with the sensing electrode at the applied voltage.

In some cases, the applied voltage is calibrated. The calibrating can include estimating an expected escape voltage distribution versus time for the sensing electrode. The calibration can then compute a difference between the expected escape voltage distribution and a reference point (e.g., an arbitrary reference point, such as zero). The calibration can then shift the applied voltage by the computed difference. In some cases, the applied voltage decreases over time.

In some cases, a distribution of expected escape voltages versus time is estimated. In some instances, the reference point is zero volts. The method can removes detected variations in expected escape voltage distribution. In some cases, the method is performed on a plurality of independently addressable nanopores each adjacent to a sensing electrode.

In some embodiments, the presence of the tag in the nanopore reduces the current measured with the sensing electrode at the applied voltage. In some cases, the tagged nucleotides comprise a plurality of different tags and the method detects each of the plurality of different tags.

In some instances, the calibration increases the accuracy of the method when compared to performing the method without calibration. In some cases, the calibration compensates for changes in electrochemical conditions over time. In some instances, the calibration compensates for different nanopores having different electrochemical conditions in a device having a plurality of nanopores. In some embodiments, the calibration compensates for different electrochemical conditions for each performance of the method. In some cases, the method further comprises calibrating variations in a current gain and/or variations in a current offset.

Expandamer Sequencing Methods

The present disclosure provides methods for sequencing a nucleic acid molecule using expandamer sequencing. Expandamer sequencing involves a number of steps that create an expanded polymer that is longer than the nucleic acid to be sequenced and has a sequence derived from the nucleic acid molecule to be sequence. The expanded polymer can be threaded through a nanopore to determine its sequence. As described herein, the expanded polymer can have gates on it such that the expanded polymer can thread through the nanopore in only one direction. The steps of the method are illustrated in FIGS. 33 to 36. Further information regarding nucleic acid sequencing by expansion (i.e., expandamers) can be found in U.S. Pat. No. 8,324,360, which is incorporated herein by reference in its entirety.

Figure 33:
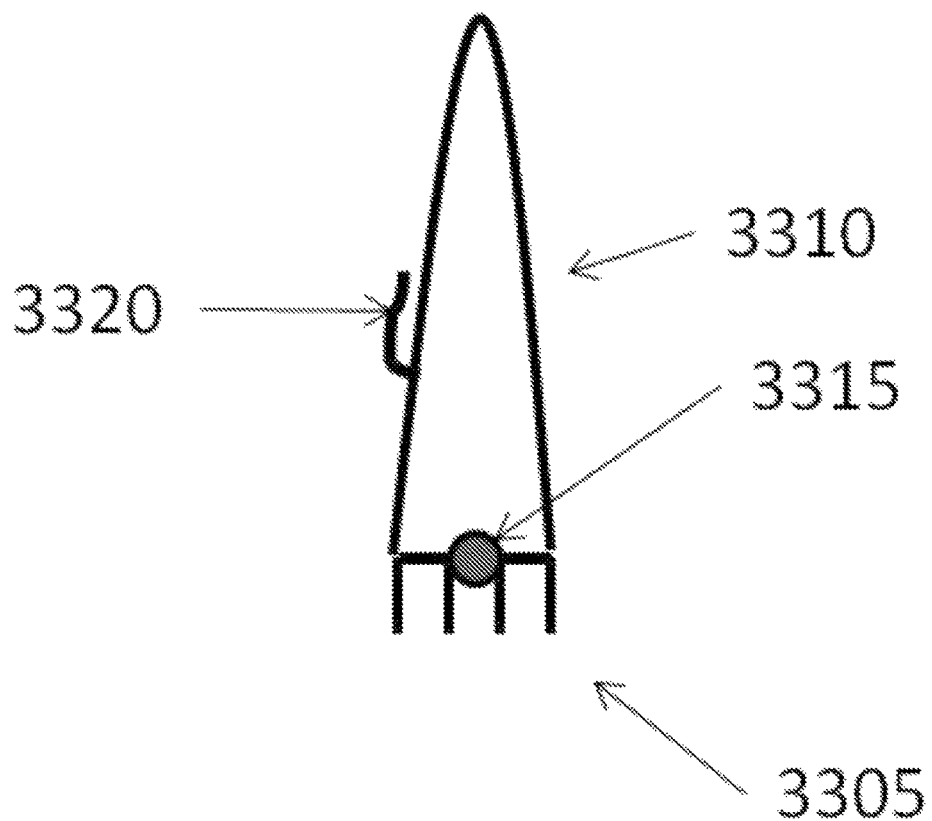
FIG. 33 shows an example of a probe for use in expandamer sequencing.

With reference to FIG. 33, in an aspect, a method for nucleic acid sequencing comprises providing a single stranded nucleic acid to be sequenced and providing a plurality of probes. The probes comprise a hybridization moiety 3305 capable of hybridizing with the single stranded nucleic acid, a loop structure 3310 having two ends, where each end is attached to the hybridization moiety, and a cleavable group 3315 located in the hybridization moiety between the ends of the loop structure. The loop structure comprises a gate 3320 that prevents the loop structure from threading through a nanopore in a reverse direction.

Figure 34:
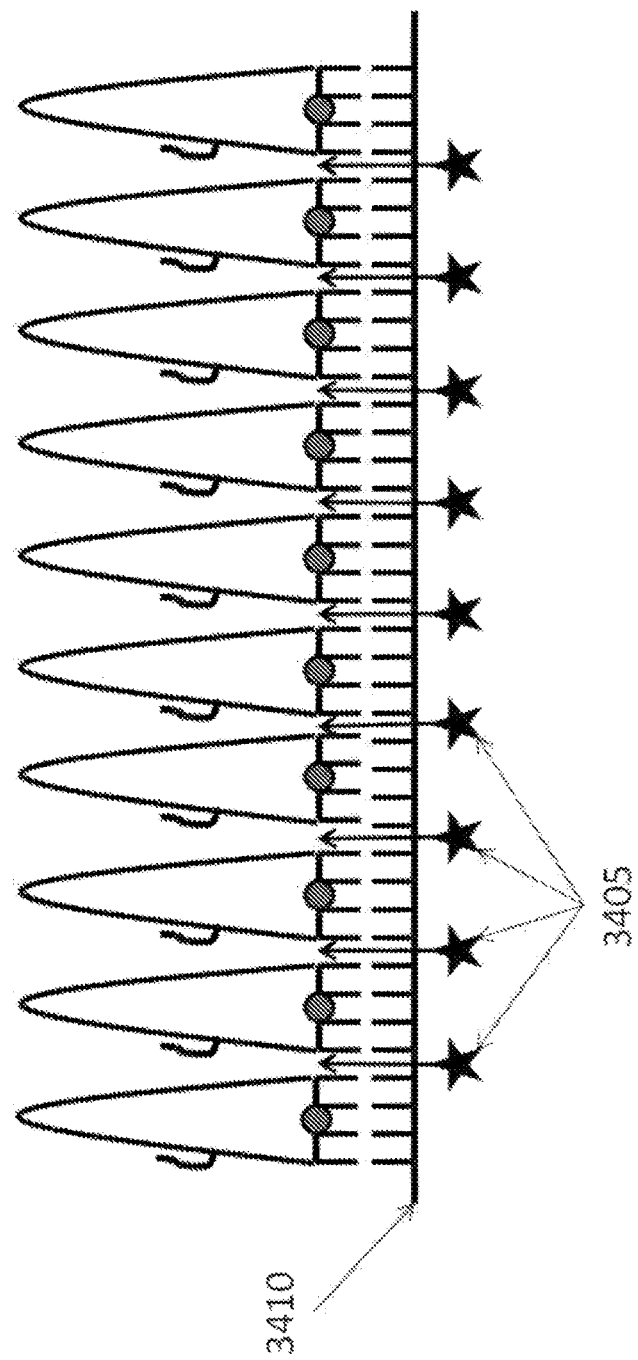
FIG. 34 shows an example of expandamer probes being polymerized.
Figure 35:
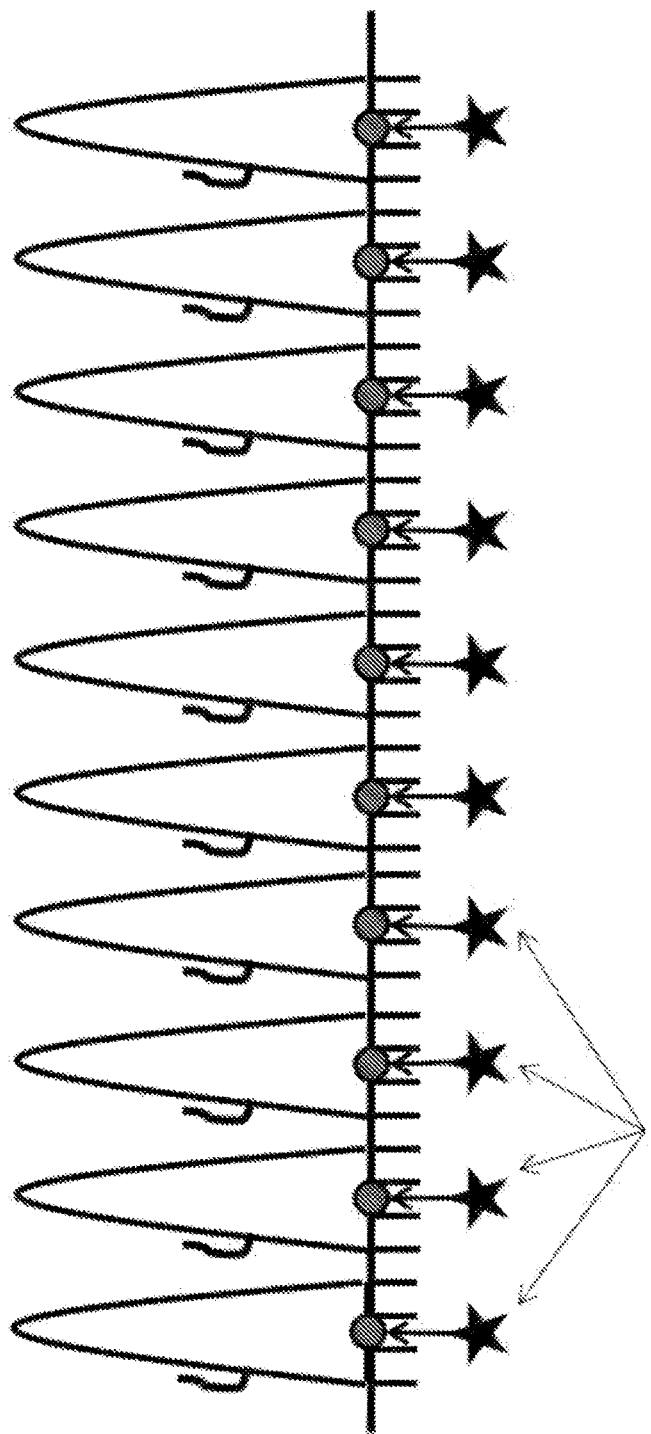
FIG. 35 shows an example of cleaving the cleavable groups to provide an expanded thread to be sequenced.

With reference to FIG. 34, the method can include polymerizing 3405 the plurality of probes in an order determined by hybridization of the hybridization moieties with the single stranded nucleic acid to be sequenced 3410. With reference to FIG. 35, the method can include cleaving 3505 the cleavable groups to provide an expanded thread to be sequenced.

Figure 36:
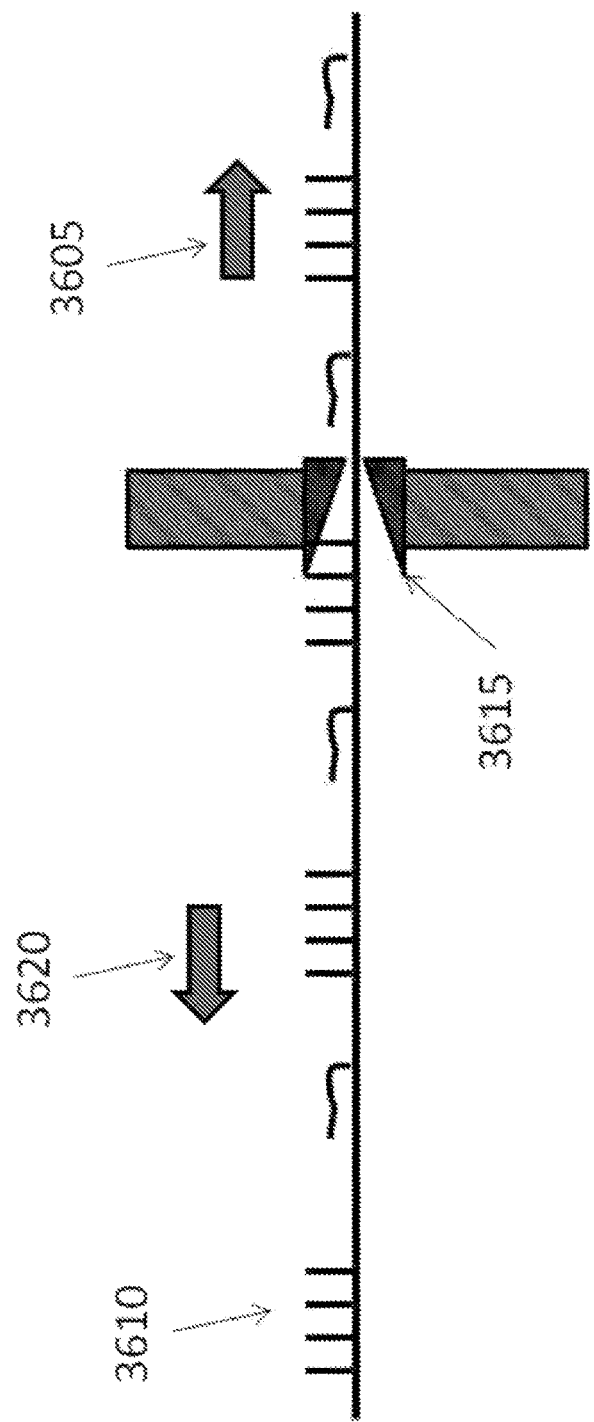
FIG. 36 shows an example of threading the expanded thread through a nanopore.

With reference to FIG. 36, the method can include threading 3605 the expanded thread 3610 through a nanopore 3615, where the gates prevent the expanded thread from threading through the nanopore in the reverse direction 3620. The method can include detecting, with the aid of the nanopore, the loop structures of the expanded thread in the order determined by hybridization of the hybridization moieties with the single stranded nucleic acid to be sequenced, thereby sequencing the single stranded nucleic acid to be sequenced.

In some cases, the loop structure comprises a narrow segment and the gate is a polymer comprising two ends, where a first end is affixed to the loop structure adjacent to the narrow segment and a second end is not affixed to the loop structure. The loop structure can be capable of being threaded through a nanopore in a first direction where the gate aligns adjacent to the narrow segment. In some embodiments, the loop structure is not capable of being threaded through the nanopore in the reverse direction where the gate does not align adjacent to the narrow segment.

In some cases, the gate comprises nucleotides. The gate can base pair with the loop structure when the gate does not align adjacent to the narrow segment.

The narrow segment can comprise any polymer or molecule that is sufficiently narrow such that the polymer can pass through a nanopore when a gate is aligned with the narrow segment. In some cases, the narrow segment comprises a-basic nucleotides (i.e., a nucleic acid side chain not having nucleotide bases attached thereto) or a carbon chain.

In some instances, an electrode is re-charged between periods of detection. The expanded thread does not generally thread through the nanopore in the reverse direction when the electrode is re-charged.

Non-Sequencing Methods and Applications

The devices and methods described herein can be used to measure certain properties of nucleic acid samples and/or nucleic acid molecules other than their nucleic acid sequence (e.g., the length of the sequence or any measure of the quality of the nucleic acid sample including but not limited to the degree of cross-linking of the nucleic acids in the sample). In some cases, it can be desirable to not determine the sequence of a nucleic acid molecule. For instance, individual humans (or other organisms such as horses and the like) can be identified by determining the lengths of certain repeating sequences in the genome (e.g., known as microsatellites, Simple Sequence Repeats (SSRs), or Short Tandem Repeats (STRs)). One may wish to know the length of one or more STRs (e.g., to identify parentage or the perpetrator of a crime) without knowing the sequence of the STR and/or the sequence of DNA found before (5') or after (3') the STR (e.g., so as to not identify the person's race, likelihood of contracting a disease, and the like).

In an aspect, a method identifies one or more STRs present in a genome. Any number of STRs can be identified (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more). The STR can comprise a repeat segment (e.g., 'AGGTCT' of the sequence SEQ. ID. No. 1-AGGTCT AGGTCT AGGTCT AGGTCT AGGTCT AGGTCT) having any number of nucleic acid bases (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more bases). The STR can comprise any number of repeated repeat segments, generally repeated consecutively (e.g., repeated 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more times).

The number of nucleotide incorporation events and/or the length of a nucleic acid or segment thereof can be determined by using nucleotides that have the same tag attached to some, most or all of the tagged nucleotides. Detection of a tag (either pre-loaded into a nanopore prior to release or directed into the nanopore subsequent to release from the tagged nucleotide) indicates that a nucleotide incorporation event has taken place, but in this instance does not identify which nucleotide has been incorporated (e.g., no sequence information is determined).

In some embodiments, all nucleotides (e.g., all adenine (A), cytosine (C), guanine (G), thymine (T) and/or uracil (U) nucleotides) have the same tag coupled to the nucleotide. In some cases, however, this may not be required. At least some of the nucleotides can have tags that identify the nucleotide (e.g., such that some sequence information will be determined). In some cases, about 5%, about 10%, about 15%, about 20%, about 25%, about 30%, about 40%, or about 50% of the nucleotides have tags that identify the nucleotide (e.g., such that some nucleic acid positions are sequenced). The sequenced nucleic acid positions can be distributed randomly along the nucleic acid chain. In some cases, all of a single type of nucleotide have an identifying tag (e.g., such that all adenines are sequenced for example). In some cases, at least 5%, at least 10%, at least 15%, at least 20%, at least 25%, at least 30%, at least 40%, or at least 50% of the nucleotides have tags that identify the nucleotide. In some embodiments, at most 5%, at most 10%, at most 15%, at most 20%, at most 25%, at most 30%, at most 40%, or at most 50% of the nucleotides have tags that identify the nucleotide. In some embodiments, all the nucleic acid or segment thereof is a Short Tandem Repeat (STR).

In an aspect, a method for determining the length of a nucleic acid or segment thereof with the aid of a nanopore in a membrane adjacent to a sensing electrode comprises providing tagged nucleotides into a reaction chamber comprising the nanopore. The nucleotides can have different bases, such as at least two different bases, containing the same tag coupled to a nucleotide, which tag is detectable with the aid of the nanopore. The method can further include carrying out a polymerization reaction with the aid of a polymerase, thereby incorporating an individual tagged nucleotide of the tagged nucleotides into a growing strand complementary to a single stranded nucleic acid molecule from the nucleic acid sample. The method can further include detecting, with the aid of the nanopore, a tag associated with the individual tagged nucleotide during or subsequent to incorporation of the individual tagged nucleotide.

In an aspect, a method for determining the length of a nucleic acid or segment thereof with the aid of a nanopore in a membrane adjacent to a sensing electrode comprises providing tagged nucleotides into a reaction chamber comprising the nanopore. An individual tagged nucleotide of the tagged nucleotides can contain a tag coupled to a nucleotide, which tag is capable of reducing the magnitude of current flowing through the nanopore relative to the current when the tag is not present.

In some embodiments, the method further comprises carrying out a polymerization reaction with the aid of a polymerase, thereby incorporating an individual tagged nucleotide of the tagged nucleotides into a growing strand complementary to a single stranded nucleic acid molecule from the nucleic acid sample and reducing the magnitude of current flowing through the nanopore. The magnitude of the current can be reduced by any suitable amount, including about 5%, about 10%, about 15%, about 20%, about 25%, about 30%, about 40%, about 50%, about 60%, about 70%, about 80%, about 90%, about 95%, or about 99%. In some embodiments, the magnitude of the current is reduced by at least 5%, at least 10%, at least 15%, at least 20%, at least 25%, at least 30%, at least 40%, at least 50%, at least 60%, at least 70%, at least 80%, at least 90%, at least 95%, or at least 99%. In some embodiments, the magnitude of the current is reduced by at most 5%, at most 10%, at most 15%, at most 20%, at most 25%, at most 30%, at most 40%, at most 50%, at most 60%, at most 70%, at most 80%, at most 90%, at most 95%, or at most 99%.

The method can further comprise detecting, with the aid of the nanopore, periods of time between incorporation of the individual tagged nucleotides (e.g., periods 605 in FIG. 6). The periods of time between incorporation of the individual tagged nucleotides can have a high magnitude of current. In some embodiments, the magnitude of current flowing through the nanopore between nucleotide incorporation events is (e.g., returns to) about 50%, about 60%, about 70%, about 80%, about 90%, about 95%, or about 99% of the maximum current (e.g., when no tag is present). In some embodiments, the magnitude of current flowing through the nanopore between nucleotide incorporation events is at least 50%, at least 60%, at least 70%, at least 80%, at least 90%, at least 95%, or at least 99% of the maximum current.

In some instances, a section of nucleic acid is sequenced before (5') or after (3') the STR to identify which STR is having its length determined in a nanopore (e.g., in a multiplexed context where a plurality of primers are directed toward a plurality of STRs). In some cases, about 2, 3, 4, 5, 6, 7, 8, 9, 10, 11, 12, 13, 14, 15, or more nucleic acids are sequenced before (5') or after (3') the STR.

Pattern Matching

This disclosure also provides electronic readers for matching patterns of signals detected by a nanopore device with known (or reference) signals. The nanopore device can include a nanopore in a membrane, as described elsewhere herein. The known signals may be maintained in a memory location, such as a remote database or memory location located on a chip comprising the nanopore device. An electronic reader can match patterns with the aid of a pattern matching algorithm, which can be implemented with the aid of a computer processor of the electronic reader. The electronic reader may be located on the chip.

Pattern matching may be implemented in real time, such as while data is being gathered by the nanopore device. As an alternative, pattern matching can be implemented by first collecting data and subsequently processing the data to match patterns.

In some cases, the reader contains a list of one or more nucleic acid sequences that are of interest to a user (also "white list" herein), and a list (or a plurality of lists) of one or more other nucleic acid sequences that are not of interest to a user (also "black list" herein). During nucleic acid detection, including nucleic acid incorporation events, the reader may detect and record nucleic acid sequences that are in the white list, and not detect or record nucleic acid sequences that are in the black list.

EXAMPLES

Example 1—Non-Faradaic Conduction

Figure 37:
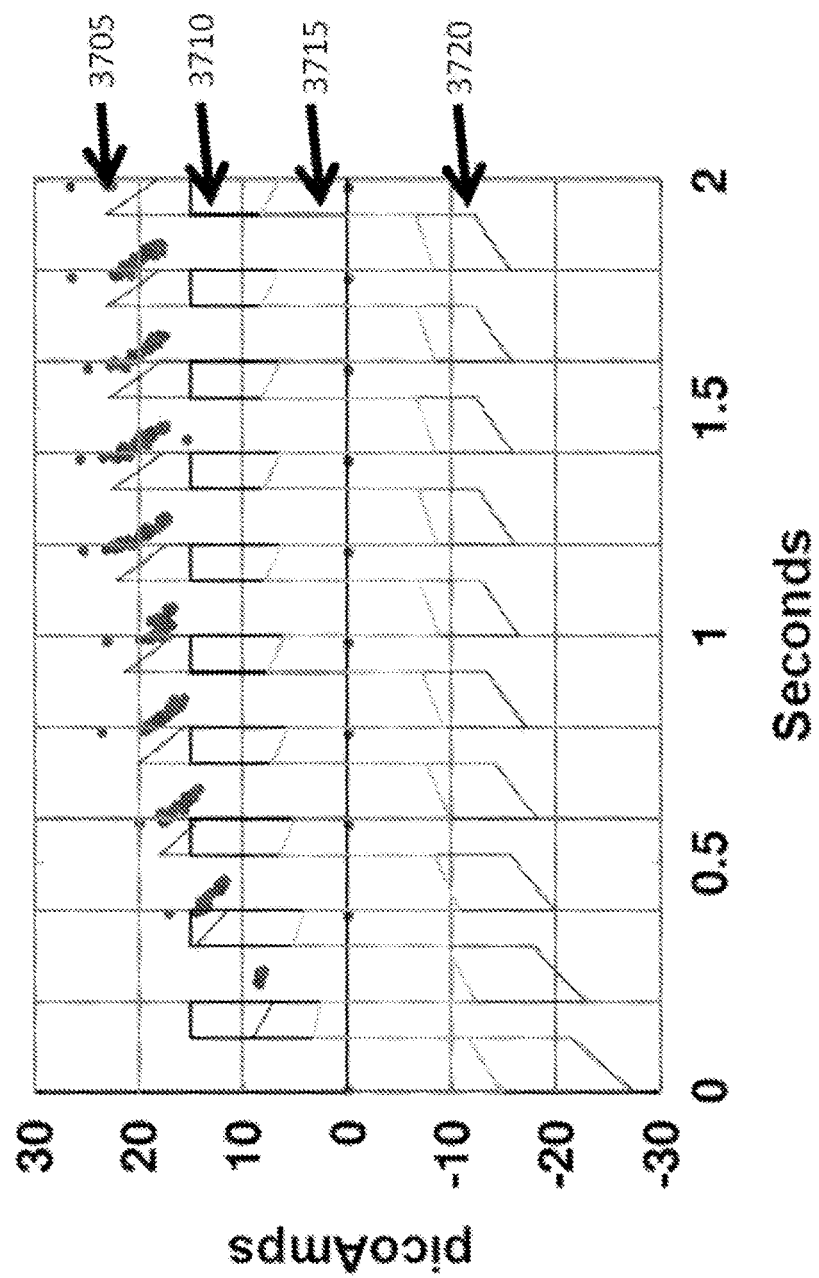
FIG. 37 shows an example of non-Faradaic conduction.

FIG. 37 shows that non-Faradaic conduction can decouple the nanopore from modulation. The vertical axis of the figure is current measured in picoamps (pA) ranging from −30 to 30. The horizontal axis is time measured in seconds (s) ranging from 0 to 2. The waveform has a 40% duty cycle. The data points 3705 are measured current with a spongy platinum working electrode in the presence of 150 mM KCl, pH 7.5 with 20 mM HEPES buffer and 3 mM $SrCl_2$ above and below the bilayer. There is 240 nM of sticky polymerase and a 5GS sandwich with 0.0464 O.D. The lipid is 75% phosphatidylethanolamine (PE) and 25% phosphatidylcholine (PC). The simulated voltage 3710 across the working electrode and counter electrode (AgCl pellet) is shown multiplied by 100 to fit onto the plot. The simulated electrochemical potential across the nanopore-polymerase complex 3715 is shown multiplied by 100 to fit onto the plot. The current 3720 is simulated using a simulation program with integrated circuit emphasis (SPICE) model.

Example 2—Tag Capture

Figure 38:
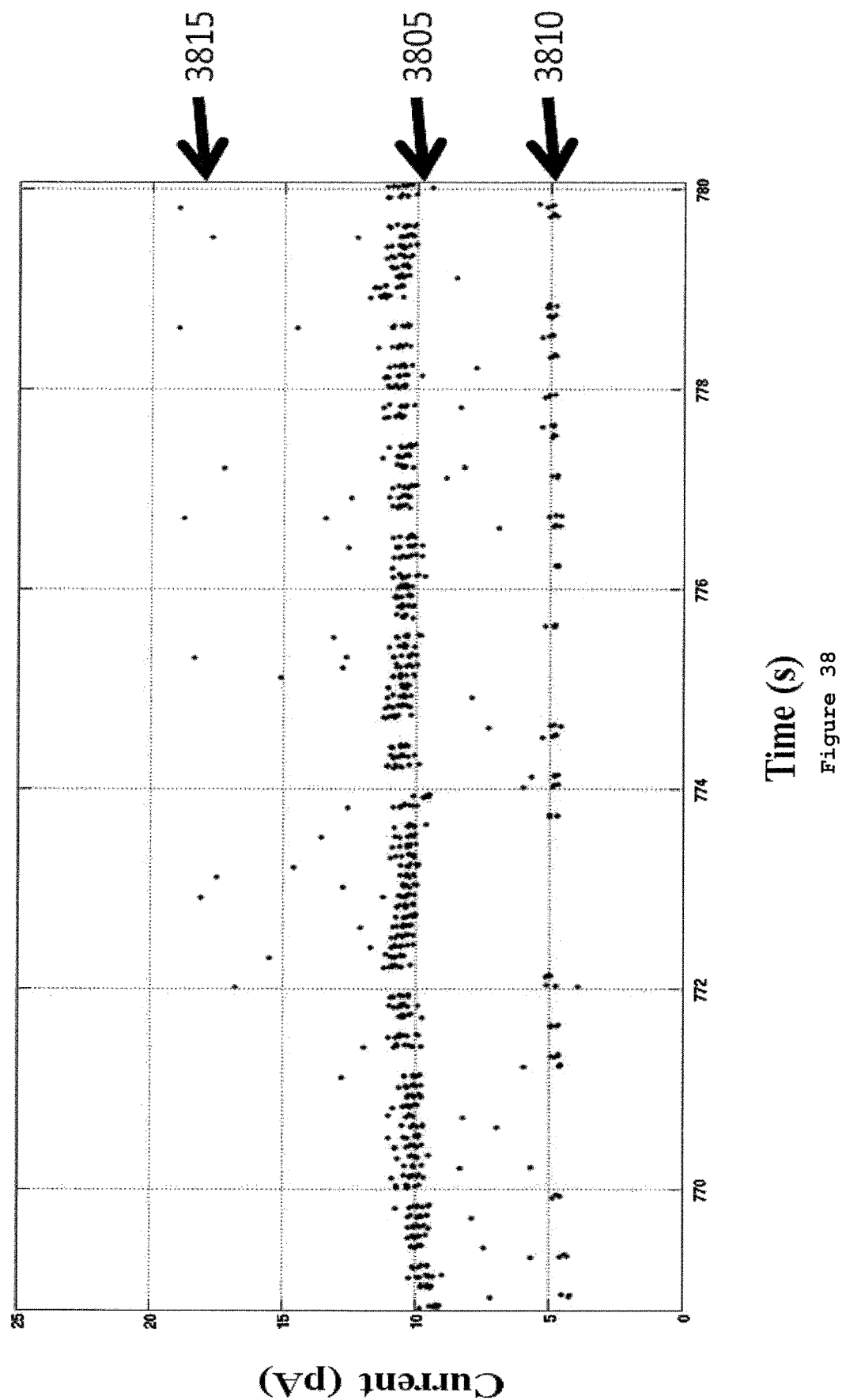
FIG. 38 shows an example of the capture of two tag molecules.

FIG. 38 shows two tags being captured in a nanopore in an alternating current (AC) system. The vertical axis of the figure is current measured in picoamps (pA) ranging from 0 to 25. The horizontal axis is time measured in seconds (s) ranging from about 769 to 780. A first tag 3805 is captured at about 10 pA. A second tag 3810 is captured at about 5 pA. The open channel current 3815 is about 18 pA. Few data points are seen at the open channel current due to the rapid capture of the tags. The wave form is from 0 to 150 mV at 10 Hz and a 40% duty cycle. The solution contains 150 mM KCl.

Example 3—Tag Sequencing

Figure 39:
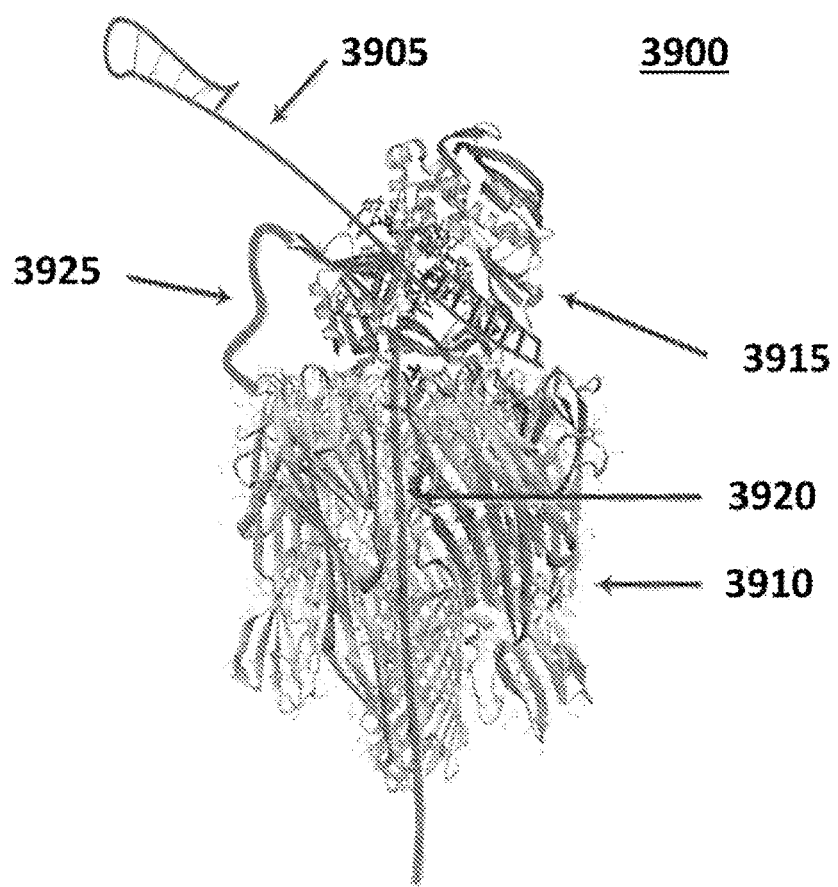
FIG. 39 shows an example of a ternary complex formed between a nucleic acid to be sequenced, a tagged nucleotide and a fusion between a nanopore and a polymerase.

FIG. 39 shows an example of a ternary complex 3900 formed between a template DNA molecule to be sequenced 3905, a fusion of a hemolysin nanopore 3910 and a DNA polymerase 3915, and a tagged nucleotide 3920. The polymerase 3915 is attached to the nanopore 3910 with a protein linker 3925. The nanopore/polymerase construct is formed such that only one of the seven polypeptide monomers of the nanopore have a polymerase attached. Part of the tagged nucleotide threads into 3920 the nanopore and affects the current passing through the nanopore.

Figure 40:
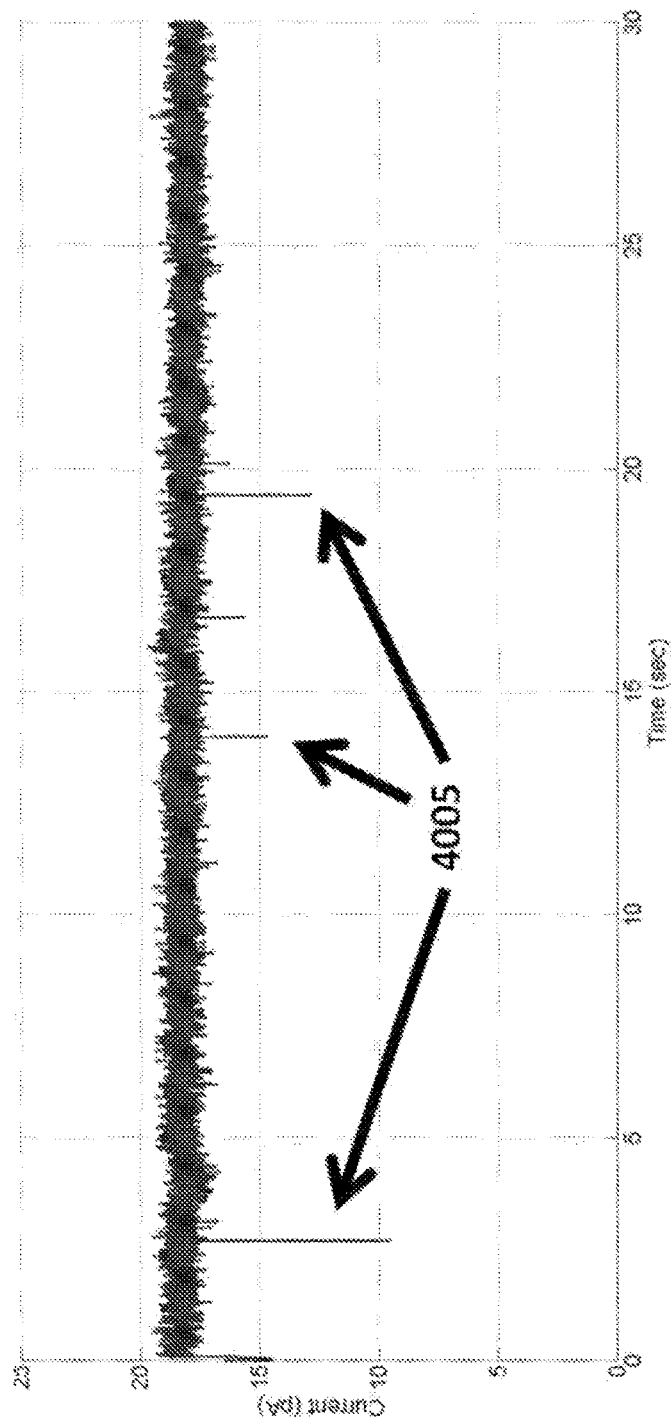
FIG. 40 shows an example of the current flowing through a nanopore without a tagged nucleotide present.

FIG. 40 shows the current flowing through the nanopore in the presence of template DNA to be sequenced, but without tagged nucleotides. The solution in contact with the nanopore has 150 mM KCl, 0.7 mM $SrCl_2$, 3 mM $MgCl_2$ and 20 mM HEPES buffer pH 7.5, at 100 mV applied voltage. The current remains near 18 picoamps (pA) with a few exceptions 4005. The exceptions can be electronic noise and can be only one data point on the horizontal time axis. The electronic noise may be mitigated using an algorithm that distinguishes noise from signal, such as, for example, an adaptive signal processing algorithm.

Figure 41:
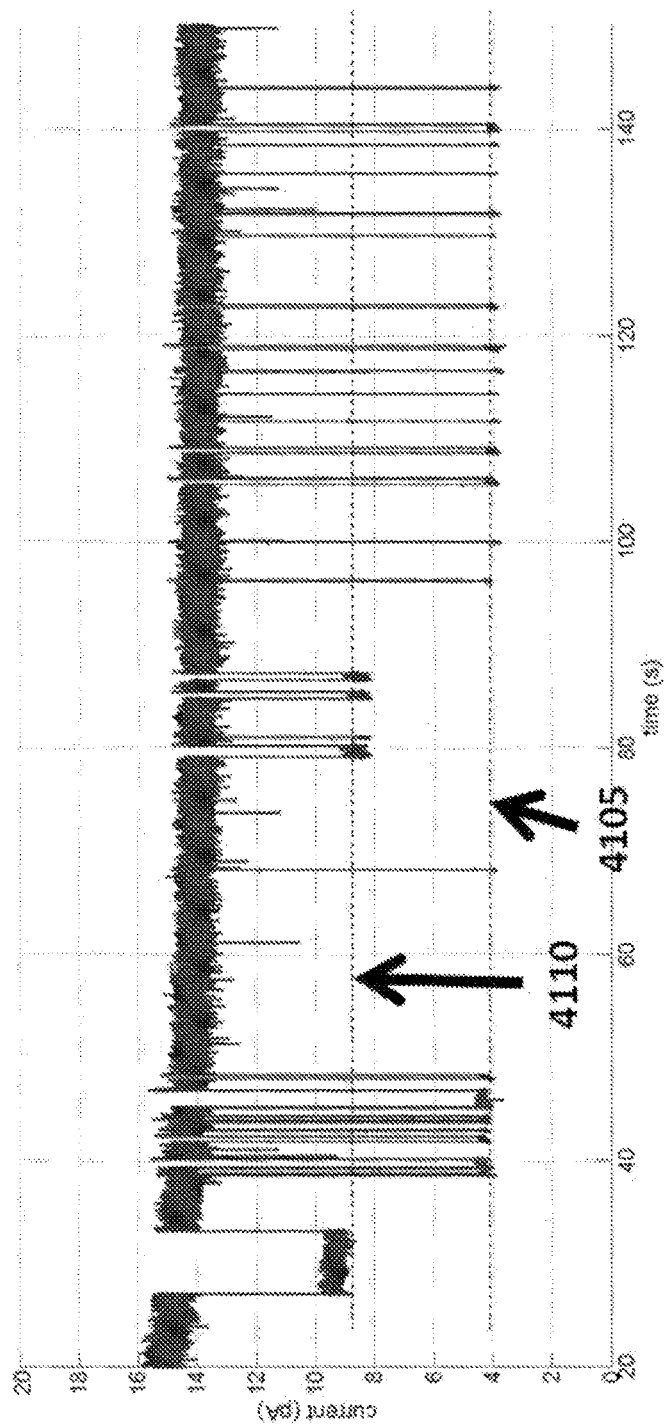
FIG. 41 shows an example of using current levels to distinguish between different tagged nucleotides.
Figure 42:
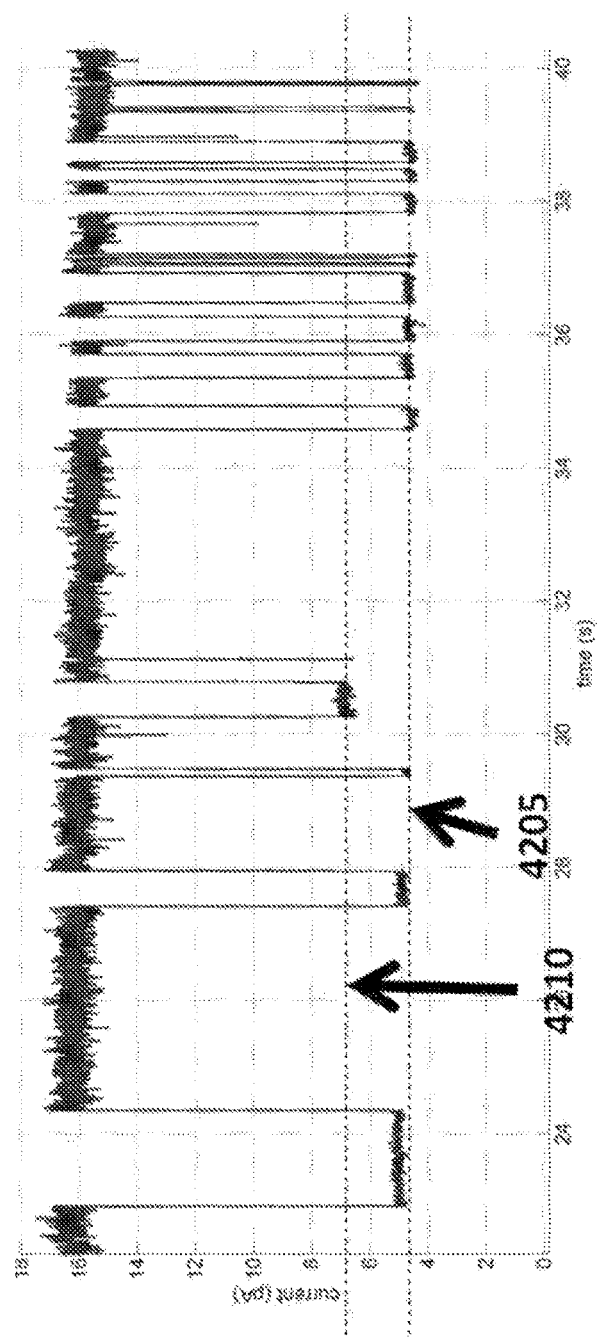
FIG. 42 shows an example of using current levels to distinguish between different tagged nucleotides.
Figure 43:
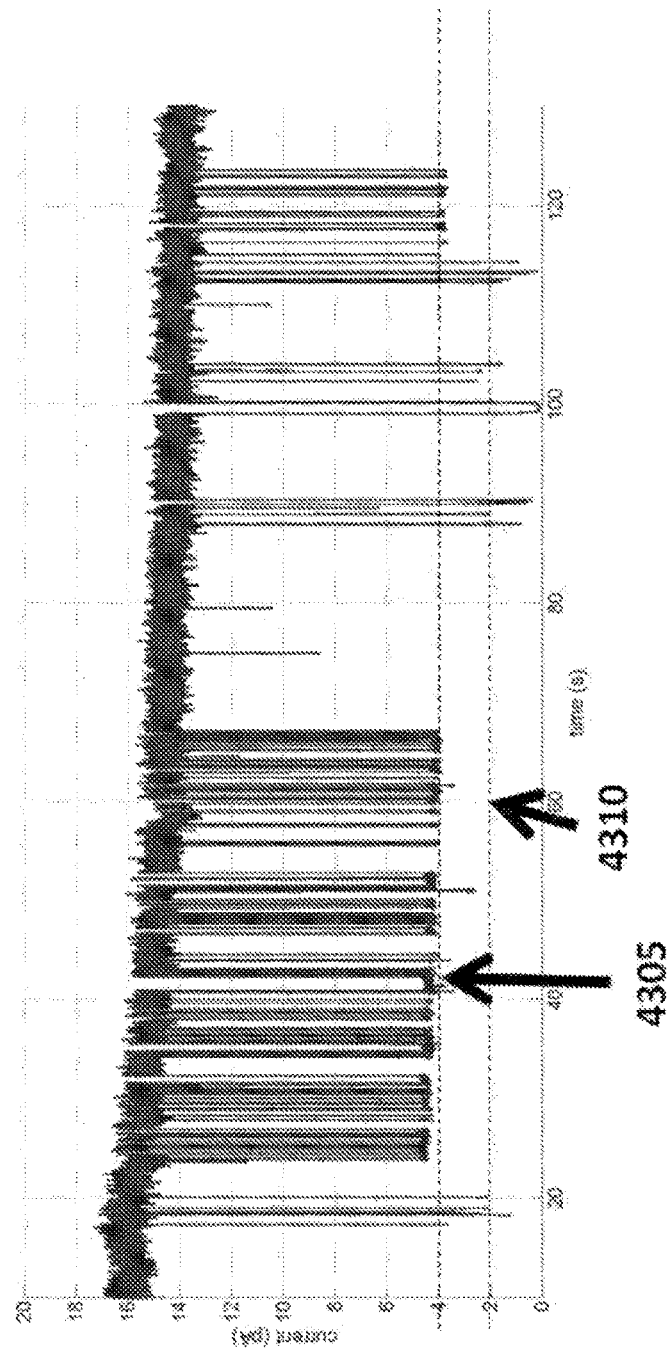
FIG. 43 shows an example of using current levels to distinguish between different tagged nucleotides.

FIG. 41, FIG. 42 and FIG. 43 show that different tags provide different current levels. In all examples, the solution in contact with the nanopore has 150 mM KCl, 0.7 mM $SrCl_2$, 3 mM $MgCl_2$ and 20 mM HEPES buffer pH 7.5, at 100 mV applied voltage. FIG. 41 shows a guanine (G) 4105 being distinguished from a thymine (T) 4110. The tags are dT6P-T6-dSp8-T16-C3 (for T) having a current level of about 8 to 10 pA and dG6P-Cy3-30T-C6 (for G) and having a current level of about 4 or 5 pA. FIG. 42 shows a guanine (G) 4205 being distinguished from an adenine (A) 4210. The tags are dA6P-T4-(Sp18)-T22-C3 (for A) having a current level of about 6 to 7 pA and dG6P-Cy3-30T-C6 (for G) and having a current level of about 4 or 5 pA. FIG. 43 shows a guanine (G) 4305 being distinguished from a cytosine (C) 4310. The tags are dC6P-T4-(Sp18)-T22-C3 (for C) having a current level of about 1 to 3 pA and dG6P-Cy3-30T-C6 (for G) and having a current level of about 4 or 5 pA.

Figure 44:
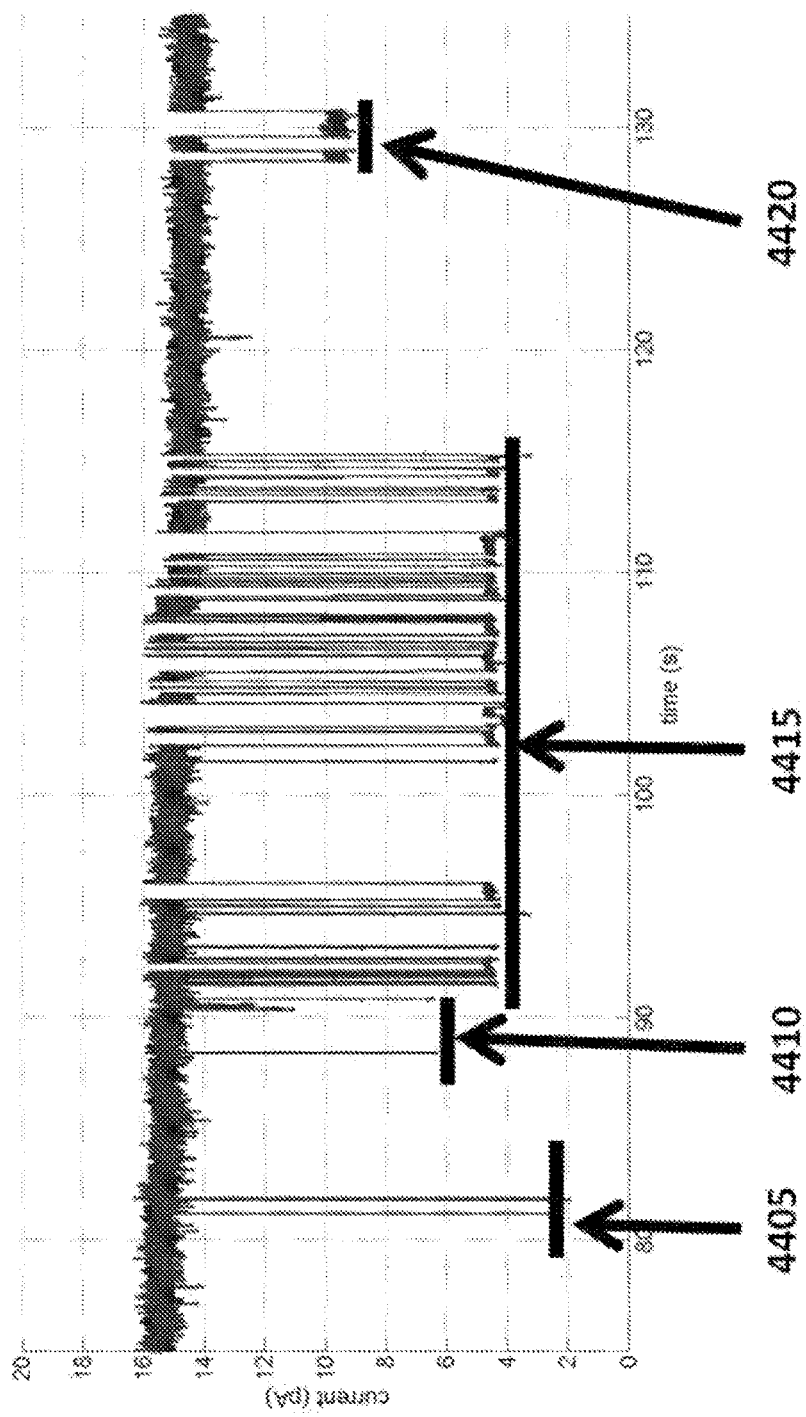
FIG. 44 shows an example of using current levels to sequence a nucleic acid molecule using tagged nucleotides.

FIG. 44, FIG. 45, FIG. 46, and FIG. 47 show examples of sequencing using tagged nucleotides. The DNA molecule to be sequenced is single stranded and has the sequence AGTCAGTC (SEQ. ID. No: 36) and is stabilized by two flanking hairpin structures. In all examples, the solution in contact with the nanopore has 150 mM KCl, 0.7 mM $SrCl_2$, 3 mM $MgCl_2$ and 20 mM HEPES buffer pH 7.5, at 100 mV applied voltage. Four tags corresponding to guanine (dG6P-Cy3-30T-C6), adenine (dA6P-T4-(Sp18)-T22-C3), cytosine (dC6P-T4-(Sp18)-T22-C3) and thymine (dT6P-T6-dSp8-T16-C3) are included in the solution. FIG. 44 shows an example where four consecutive tagged nucleotides are identified (i.e., C 4405, A 4410, G 4415 and T 4420) corresponding to the sequence GTCA in SEQ. ID. No: 36. The tag can pass into and out of the nanopore several times before being incorporated into the growing strand (e.g., so for each incorporation event, the current level can switch several times between the open channel current and the reduced current level that distinguishes the tag).

Figure 45:
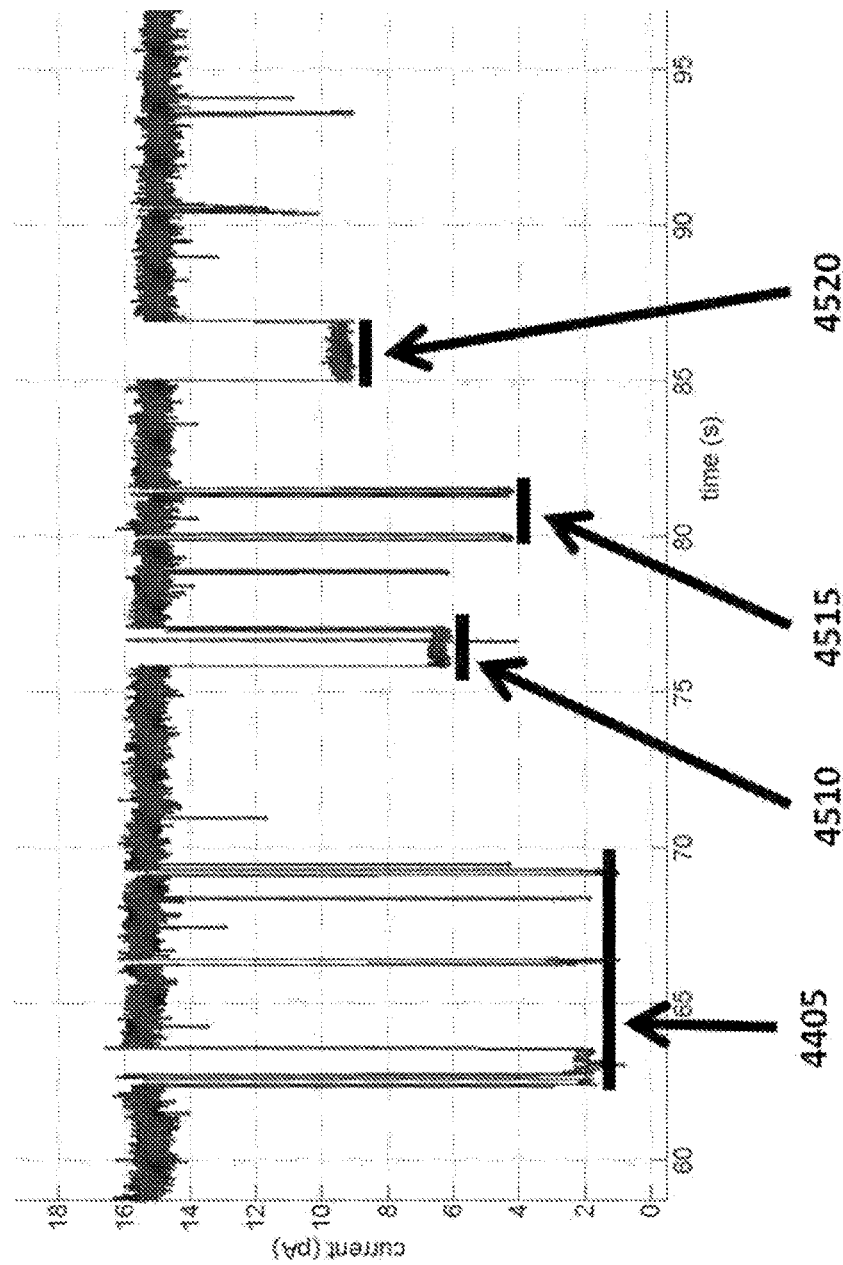
FIG. 45 shows an example of using current levels to sequence a nucleic acid molecule using tagged nucleotides.

The duration of current reduction can be different between trials, for any reason, including but not limited to the number of times that the tag goes into and out of the nanopore being different and/or the tag being briefly held by the polymerase but not fully incorporated into a growing nucleic acid strand. In some embodiments, the duration of current reduction is approximately consistent between trials (e.g., varies by no more than about 200%, 100%, 50%, or 20%). In some cases, the enzyme, applied voltage waveform, concentration of divalent and/or mono-valent ions, temperature, and/or pH are chosen such that the duration of current reduction is approximately consistent between trials. FIG. 45 shows the same sequence GTCA in SEQ. ID. No: 36 being identified as was shown in FIG. 44 (i.e., in this case the identified tagged nucleotides are C 4505, A 4510, G 4515 and T 4520). In some cases, the current remains reduced for an extended period of time (e.g., about 2 seconds as shown at 4520).

Figure 46:
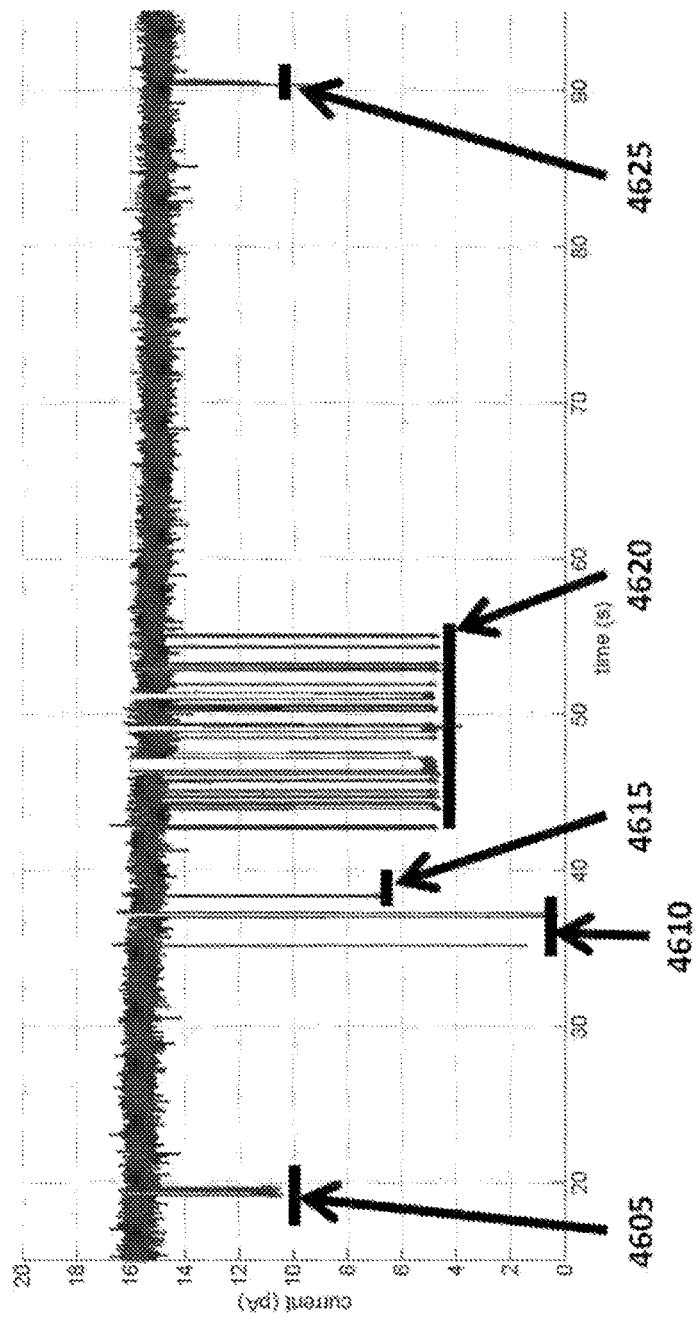
FIG. 46 shows an example of using current levels to sequence a nucleic acid molecule using tagged nucleotides.
Figure 47:
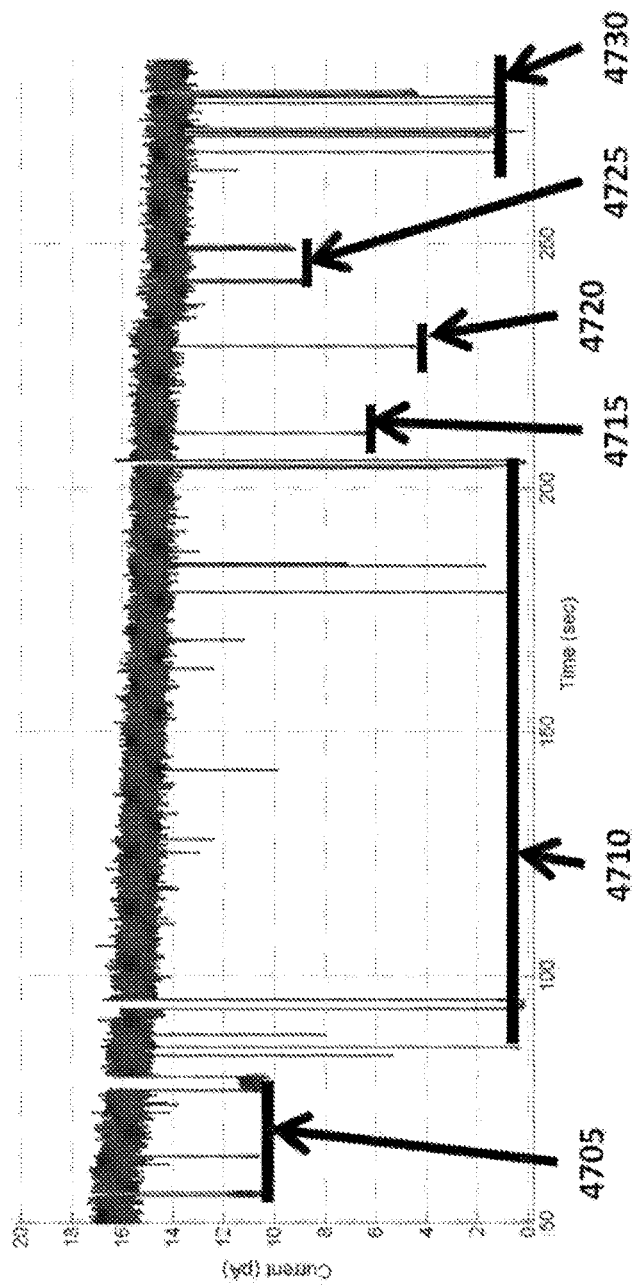
FIG. 47 shows an example of using current levels to sequence a nucleic acid molecule using tagged nucleotides.

FIG. 46 shows five consecutive tagged nucleotides being identified (i.e., T 4605, C 4610, A 4615, G 4620, T 4625) corresponding to the sequence AGTCA in SEQ. ID. No: 36. FIG. 47 shows five consecutive tagged nucleotides being identified (i.e., T 4705, C 4710, A 4715, G 4720, T 4725, C 4730) corresponding to the sequence AGTCAG in SEQ. ID. No: 36.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for assembling a protein having a plurality of subunits, the method comprising:
   a) providing a plurality of first subunits;
   b) providing a plurality of second subunits, wherein the second subunits are modified with respect to the first subunits;
   c) contacting the first subunits with the second subunits in a first ratio to form a plurality of proteins having the first subunits and the second subunits, wherein the plurality of proteins have a plurality of ratios of the first subunits to the second subunits; and
   d) fractionating the plurality of proteins using ion-exchange chromatography to enrich proteins that have a second ratio of the first subunits to the second subunits, wherein the second ratio is one second subunit per (n−1) first subunits, wherein 'n' is the number of subunits comprising the protein.

2. The method of claim 1, wherein the protein is a nanopore.

3. The method of claim 2, wherein the nanopore is at least 80% homologous to alpha-hemolysin.

4. The method of claim 1, wherein the first subunits or the second subunits comprise a purification tag.

5. The method of claim 4, wherein the purification tag is a poly-histidine tag.

6. The method of claim 1, wherein the second ratio is 1 second subunit per 6 first subunits.

7. The method of claim 1, wherein the second subunits comprise a chemically reactive moiety.

8. The method of claim 7, wherein the method further comprises (e) performing a reaction to attach an entity to the chemically reactive moiety.

9. The method of claim 8, wherein the protein is a nanopore and the entity is a polymerase.

10. The method of claim 1, wherein the first subunits are wild-type.

11. The method of claim 1, wherein the first subunits and/or second subunits are recombinant.

12. The method of claim 1, wherein the first ratio is approximately equal to the second ratio.

13. The method of claim 1, wherein the first ratio is greater than the second ratio.

14. The method of claim 1, further comprising inserting the proteins having the second ratio of subunits into a bilayer.

15. The method of claim 1, further comprising sequencing a nucleic acid molecule with the aid of the proteins having the second ratio subunits.

16. A nanopore comprising a plurality of subunits, wherein a polymerase is attached to one of the subunits and at least one and less than all of the subunits comprise a first purification tag, and wherein the first purification tag is on the subunits not having the polymerase attached.

17. The nanopore of claim 16, wherein the nanopore is at least 80% homologous to alpha-hemolysin.

18. The nanopore of claim 16, wherein at least one of the subunits comprises a first purification tag, and wherein all of the remaining subunits comprise a first purification tag or a second purification tag.

19. The nanopore of claim 16, wherein the first purification tag is a poly-histidine tag.

* * * * *